(12) United States Patent
Leonhardt

(10) Patent No.: US 7,090,392 B2
(45) Date of Patent: Aug. 15, 2006

(54) ROADWAY FREEZING POINT MONITORING SYSTEM AND METHOD

(75) Inventor: Patrick A. Leonhardt, Rocklin, CA (US)

(73) Assignee: Energy Absorption Systems, Inc., Chicago, IL (US)

( * ) Notice: Subject to any disclaimer, the term of this patent is extended or adjusted under 35 U.S.C. 154(b) by 139 days.

(21) Appl. No.: 10/701,906

(22) Filed: Nov. 5, 2003

(65) Prior Publication Data

US 2005/0058177 A1 Mar. 17, 2005

Related U.S. Application Data

(62) Division of application No. 09/989,790, filed on Nov. 19, 2001, now Pat. No. 6,695,469.

(51) Int. Cl.
*G01N 25/02* (2006.01)

(52) U.S. Cl. .......................... 374/25; 374/21; 374/163; 374/16

(58) Field of Classification Search .............. 374/16, 374/25, 21, 166; 73/170.26; 340/580, 581, 340/589, 962, 584, 588, 870.17; 324/441, 324/446, 450, 670, 689; 702/130, 136
See application file for complete search history.

(56) References Cited

U.S. PATENT DOCUMENTS

| | | | |
|---|---|---|---|
| 2,849,701 A | 8/1958 | Clark | |
| 3,203,226 A | 8/1965 | Fiske, Jr. | |
| 3,243,793 A | 3/1966 | Goldman | |
| 3,255,412 A | 6/1966 | Liu | |
| 3,320,946 A | 5/1967 | Dethloff et al. | |
| 3,478,311 A | 11/1969 | Czingula | |
| 3,582,728 A | 6/1971 | Thoma | |
| 3,613,063 A | 10/1971 | Ciemochowski | |
| 3,634,841 A | 1/1972 | Irvine | |
| 3,636,444 A | 1/1972 | Strawn et al. | |
| 3,667,280 A | 6/1972 | Simpson | |
| 3,677,064 A | 7/1972 | Simpson | |
| 3,807,699 A | 4/1974 | France | |
| 3,855,861 A | 12/1974 | Zimmerman et al. | |
| 3,873,927 A | 3/1975 | Overall | |
| 3,882,381 A | 5/1975 | Gregory | |
| 3,891,979 A | 6/1975 | Braun et al. | |
| 3,946,594 A | 3/1976 | Surinx | |
| 3,974,993 A | 8/1976 | Hammecke | |

(Continued)

FOREIGN PATENT DOCUMENTS

CA 1 163 461 3/1984

(Continued)

OTHER PUBLICATIONS

"Aquaplaning Risk on Runways is Measured," *Airport Services Management*, Nov. 1970, 31.

(Continued)

*Primary Examiner*—Diego Gutierrez
*Assistant Examiner*—Mirellys Jagan
(74) *Attorney, Agent, or Firm*—Brinks Hofer Gilson & Lione

(57) ABSTRACT

Improved roadway freezing point monitoring systems and methods include improved sample wells for the accurate measurement of the freezing point of liquid on a roadway, the use of temperature sensors that require only two conductors to receive power and to send and receive digital address and temperature information, improved algorithms for detecting the freeze point of liquid on the roadway, the use of conductivity measurements to verify detected freeze points, and the transmission of temperature information via the Internet to remote computers.

12 Claims, 14 Drawing Sheets

U.S. PATENT DOCUMENTS

| | | | |
|---|---|---|---|
| 3,986,110 A | | 10/1976 | Overall et al. |
| 4,119,909 A | | 10/1978 | DeBerry |
| 4,135,151 A | | 1/1979 | Rogers et al. |
| 4,164,868 A | | 8/1979 | Suntola |
| 4,210,021 A | | 7/1980 | Vykhodtsev et al. |
| 4,222,044 A | | 9/1980 | Boschung |
| 4,227,411 A | * | 10/1980 | Abramovich ............ 73/335.02 |
| 4,281,286 A | | 7/1981 | Briggs |
| 4,333,004 A | | 6/1982 | Forgue et al. |
| 4,335,613 A | | 6/1982 | Luukkala |
| 4,378,168 A | | 3/1983 | Kuisma et al. |
| 4,383,770 A | | 5/1983 | Boschung et al. |
| 4,500,940 A | | 2/1985 | Kuisma et al. |
| 4,523,142 A | | 6/1985 | Murata et al. |
| 4,557,420 A | | 12/1985 | Boschung et al. |
| 4,579,462 A | | 4/1986 | Rall et al. |
| 4,601,587 A | | 7/1986 | Mathiprakasam |
| 4,639,883 A | | 1/1987 | Michaelis |
| 4,657,409 A | | 4/1987 | Wiggin et al. |
| 4,679,160 A | | 7/1987 | Whitener |
| 4,745,803 A | | 5/1988 | Haavasoja |
| 4,765,187 A | | 8/1988 | Weinstein |
| 4,766,369 A | | 8/1988 | Weinstein |
| 4,801,865 A | | 1/1989 | Miller et al. |
| 4,808,009 A | | 2/1989 | Sittler et al. |
| 4,897,597 A | | 1/1990 | Whitener |
| 4,942,364 A | | 7/1990 | Nishijima et al. |
| 4,996,493 A | | 2/1991 | Monat et al. |
| 5,064,294 A | | 11/1991 | Cerf et al. |
| 5,090,817 A | | 2/1992 | Ker et al. |
| 5,141,329 A | | 8/1992 | Orlando et al. |
| 5,143,451 A | | 9/1992 | Millgard |
| 5,282,682 A | | 2/1994 | Orlando et al. |
| 5,345,223 A | | 9/1994 | Rutkiewicz |
| 5,418,522 A | | 5/1995 | Freundlieb et al. |
| 5,523,959 A | * | 6/1996 | Seegmiller .................. 702/130 |
| 5,619,144 A | | 4/1997 | Stormbom |
| 5,644,080 A | | 7/1997 | Stormbom et al. |
| 5,686,841 A | * | 11/1997 | Stolarczyk et al. ......... 324/635 |
| 5,801,647 A | | 9/1998 | Survo et al. |
| 5,833,366 A | | 11/1998 | Ma |
| 5,852,243 A | | 12/1998 | Chang et al. |
| 5,874,667 A | | 2/1999 | Kasman |
| 6,239,601 B1 | * | 5/2001 | Weinstein ................... 324/662 |
| 6,301,631 B1 | | 10/2001 | Chambers et al. |
| 6,511,220 B1 | | 1/2003 | Boschung, Jr. et al. |
| 6,692,144 B1 | * | 2/2004 | Kober et al. .................. 374/16 |
| 2002/0177942 A1 | | 11/2002 | Knaian et al. |

FOREIGN PATENT DOCUMENTS

| | | |
|---|---|---|
| DE | 31 18 997 A1 | 1/1983 |
| DE | 3924634 | 1/1991 |
| EP | 45106 | 2/1982 |
| EP | 0 241 676 | 10/1987 |
| EP | 248691 | 12/1987 |
| EP | 0 376 721 | 7/1990 |
| FI | 60079 | 7/1981 |
| FI | 61249 | 2/1982 |
| FI | 92440 | 7/1994 |
| FR | 2078982 | 10/1971 |
| GB | 2180350 A | 9/1986 |
| JP | 56148024 | 11/1981 |
| JP | 01054222 | 3/1989 |
| JP | 09143948 | 6/1997 |
| JP | 2001059205 | 3/2001 |
| JP | 2001228265 | 8/2001 |
| WO | WO 99/13295 | 9/1997 |
| WO | WO 99/31492 | 3/1999 |

OTHER PUBLICATIONS

Forbat, "An Operational Aid for Warning of Aquaplaning Conditions," *Interavia Aviation, Astronautics, Electronics*, 1971.

"Winter Beware: Scan® System 16™ is Watching You!" *Surface Systems, Inc.*, 1980.

Matthews et al., "The Development of Ice Detectin Techniques," *Cransfield Institute of Technology*.

"Winter Beware: Scan® System 16™ is Watching You!" *Surface Systems, Inc.*

"Road Weather System," *Vaisala*, Nov. 1986.

Kelley et al. "Scan Provides Data for Ice/Snow Control and Forecasting," *ICAO Bulletin*, Apr. 1987.

Mechler et al., "IRS-20/21 (Intelligent Road Sensor)," Jun. 2000 1-32.

"GMA Operating Manual," Mar. 2001, 1-39.

"Mini Thawing Agent Spray System", *Boschung Mecatronic Brochure*, date unknown.

"TMS 2000 Thawspray", *Boschung Mecatronic Brochure*, date unknown.

Awtrey, D. "The 1-Wire Weather Station." *Sensors*, Jun. 1998, 34-50.

Awtrey, D. "Transmitting Data and Power over a One-Wire bus." *Sensors*, Feb. 1997, 48-51.

Bornard, E. "Physical Bases of Freezing Point Measurements using Active and Passive Probes." *Proceedings of the 9th SIRWEC Conference*, Lulea, Sweden, Mar. 1998.

Dallas Semiconductor Corp. "DS18B20 Programmable Resolution 1-Wire Digital Thermometer." Dallas, Texas, *Dallas Semiconductor Corp.*, Apr. 2001.

Donau, P. "Water Film Thickness Measurement on Road Surfaces by means of an Early Ice Warning Sensor." *Proceedings of the 10th SIRWEC Conference*, Davos, Switzerland, Mar. 2000.

O'Grady, Albert. Building a More Perfect Union: Combining Thermistors and High Resolution ΣΔ A/D Converters>' *Sensors*, Jan. 2000, 42-47.

Prager, Denis J. and Bowman, Robert L. "Freezing-Point Depression: New Method for Measuring Ultramicro Quantities of Fluids." *Science*, Oct. 1963, 237-239.

Katz, David I. "Frensor: A New Smart Pavement Sensor." *Transportation Research Record*, 1387, 147-150.

Enator Telub AB. "Frensor: A unique freezing point sensor." www.boschungamerica.com/RWIS%20page.htm.

Boschung's "ARCTIS" Active Pavement Sensor. www.enator.se/telub/LV/systems/frensor.htm.

Dallas Semiconductor Corp. "Network for the Future: 1-Wire, Jini and Weather Stations." www.ibutton.com/weather/networking.html.

* cited by examiner

—TO FIG. 13(B)—

ROADWAY FREEZING POINT MONITORING SYSTEM AND METHOD

This application is a divisional of U.S. application Ser. No. 09/989,790 filed Nov. 19, 2001, which is now U.S. Pat. No. 6,695,469, which is incorporated herein by reference.

BACKGROUND

The application of freeze point depressants on roadways has long been a method of combating the formation of ice. Traditionally, dedicated maintenance vehicles have applied anti-icing solid or liquid chemicals to areas that have a high risk for developing ice. It is important to apply these anti-icing chemicals to the roadway before freezing occurs, as this prevents a bond from forming between ice and the roadway. Freeze-point depressants do this by depressing the freezing point of the liquid on the roadway, much as the anti-freeze in a car radiator prevents it from freezing.

To do this well, a highway agency needs to know whether the current road conditions warrant the application of chemicals. If the road surface has an adequate concentration of chemicals for the current conditions, the application of additional freeze-point depressant is unnecessary, costly, and has an impact on the environment. Road Weather Information Systems (RWIS) and their associated pavement sensors are one cost-effective way for highway agencies to monitor current road conditions, without sending personnel into the field. Many RWIS systems can send information on the current road conditions to a centralized traffic management center, where decisions on the application of additional freeze-point depressant can be made.

There are also some highway sites, such as bridges and overpasses, which typically freeze long before the rest of the roadway. Since the expense of sending a truck with anti-icing chemicals to such a site is high, many highway agencies are installing fixed anti-icing systems. These systems automatically determine the most opportune time to spray, based on the current local conditions as reported by pavement and other RWIS sensors. One of the most important parts of the RWIS system is the pavement sensor, as it allows the determination of the current conditions of the roadway.

In its simplest form, the pavement sensor can consist of a thermometer that measures the temperature of the road surface. Measuring the temperature alone does not give enough information to determine if ice will form, however. This is because the exact concentration of the liquid present on the roadway is not known. For instance, the road temperature may be near 0° C., the freezing point of water. This may mean that the formation of ice is probable; however, previous applications of anti-icing chemicals may have depressed the freezing point of the liquid on the roadway. Precipitation and its runoff may also have diluted the anti-icing chemicals previously applied to the road. To most accurately gauge the current freeze point of the roadway, a sample of the actual liquid on the roadway needs to be analyzed. One method of doing this is to freeze a small sample of solution on the roadway and determine its freezing point. Such a sensor is known as an active sensor, because it actively changes the state of the liquid that is on the road surface.

SUMMARY

The following sections describe a new active pavement sensor that includes unique features that increase the sensor's ability to accurately predict the current state of the road.

By way of general introduction, the illustrated pavement sensors include one or more of the following features, that can be used alone or in combination:

The illustrated freezing point sensor includes a sample well that has a surface in good thermal contact with a thermal link situated between the sample well and an active cooler. A temperature sensor is disposed in good thermal contact with the sample in this sample well.

The disclosed freezing point sensor confirms the freezing point as measured with an active cooler and a temperature sensor by additionally assessing the conductivity of the sample being cooled.

The illustrated sensor module determines the freezing temperature of a sample by measuring a freezing curve (a plot of temperature. versus time, begun with the sample at a temperature above its freezing temperature and continuing until the temperature of the sample is below the freezing temperature), and then assessing the shape of the freezing curve. One disclosed algorithm locates a region of the freezing curve having a slope that is level or slightly downwardly trending and that occurs (1) after a second time derivative of the freezing curve exceeds a threshold value or (2) after the first time derivative of the curve exceeds a positive threshold value. The disclosed system fits lines to multiple temperature measurements in order to improve system performance.

The disclosed system uses two-conductor temperature sensors having globally unique addresses. Power for the temperature sensor and digital signals to and from the temperature sensor are carried by a set of cables including no more than two conductors.

Temperature information is transmitted from temperature sensors having globally unique addresses to a base station, which transmits temperature information via a network such as the Internet to a remote computer.

This section has been provided only by way of general introduction, and it is not intended to narrow the scope of the following claims.

DETAILED DESCRIPTION OF THE DRAWINGS

Figure 1:
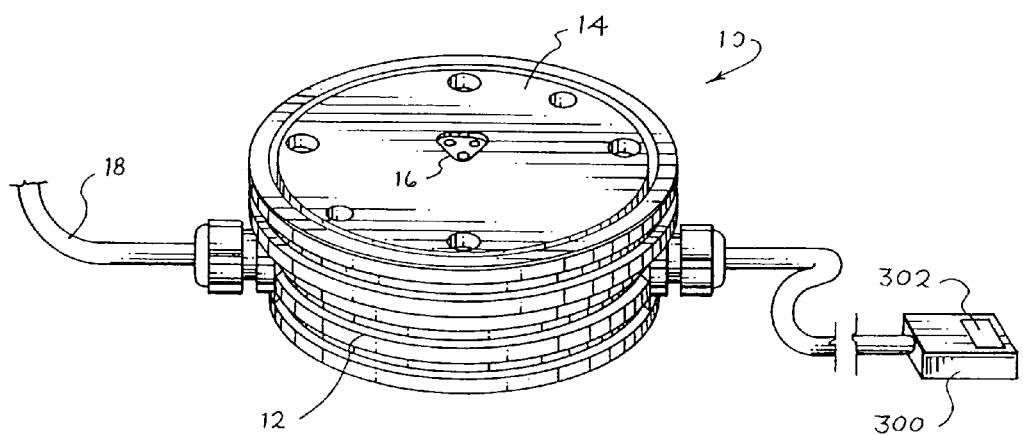
FIG. 1 is a FIG. 1 is a perspective view of a pavement sensor module that incorporates a preferred embodiment of the invention.

Turning now to the drawings, FIG. 1 shows an isometric view of an active pavement sensor module 10. The following sections will first describe the mechanical structure and electronics of the module 10, before turning to its measurement capabilities.

Description of Mechanical Structure of the Module 10

The exterior of the module 10 is formed by a lower housing 12 and a cover 14. The lower housing 12 is connected via a cable 18 with a remote station (not shown in FIG. 1), and the lower housing 12 is adapted to be mounted in a recess of a roadway such that the upper surface of the module is substantially flush with the surface of the roadway. Simply by way of example, in one embodiment the lower housing 12 is about 5 inches diameter and 2 inches in height. In this example, the cover 14 is removably mounted to the lower housing 12 to provide access to internal electronics, and to facilitate service, calibration, and upgrades to the internal electronics and software.

In this non-limiting example, the cover 14 is formed of a thermally insulative material having thermal properties and a color which are similar to that of the adjacent road surface (e.g. thermal conductivity of about 0.24 W/m·K). The use of such an insulative material for the cover 14 helps insure that the cover tracks the temperature of the road, as well as isolating a liquid collected in the cover during freezing point detection runs. In this non-limiting example, the lower housing 12 is made of a thermally conductive material to facilitate the removal of heat generated by the sensor module 10. Preferably, a ring of the same insulative material as that used for the cover 14 is secured to the top of the lower housing 12. This prevents the top cover 14 from becoming bonded to the grout material that is used to fix the module 10 in the roadway.

Figure 2:
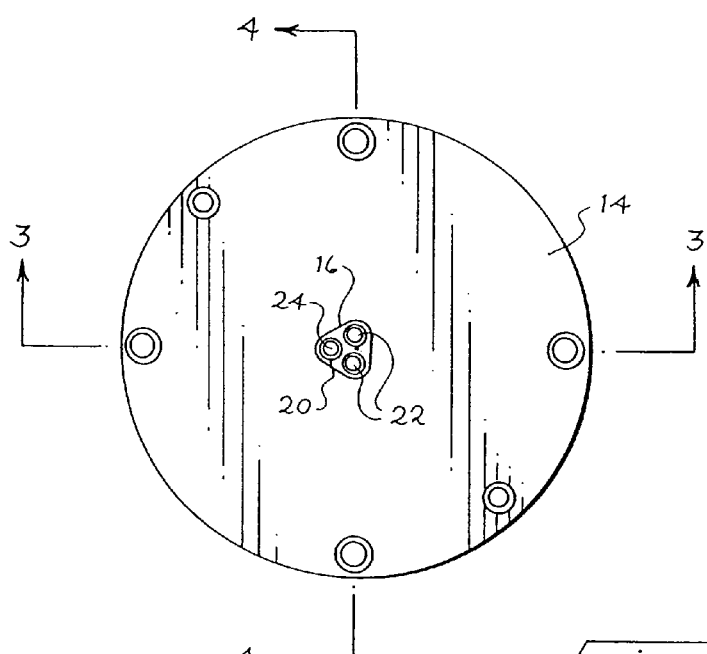
FIG. 2 is a top view of a portion of the sensor module of FIG. 1.

As shown in FIG. 2, the top cover 14 forms a sample cup 16 for collecting a small amount of liquid from the road surface. The module 10 includes a temperature sensor such as a thermistor 24 that is positioned adjacent to the sample cup 16 to measure the temperature of liquid contained in the sample cup 16. In this example, two electrical conductivity probes 22 are mounted adjacent to the sample cup 16.

Also shown in FIG. 1 is an external temperature probe 300. Although the temperature of the road can be measured via a thermometer that is embedded in the lower housing 12 of sensor module 10, a more accurate measurement can be made via a temperature sensor 302, inside of external probe 300. In this application, external probe 300 may be embedded within an inch or so of the surface of the roadway being monitored, some distance from the sensor itself. Alternatively, external probe 300 can be embedded several inches or even several feet below the surface of the roadway to monitor the subsurface temperature of the roadway. This information is useful in algorithms that use the temperature profile of the roadway to estimate what the future surface temperature will be.

Using the digital two-conductor temperature sensors described below, the temperature probe 300 can be reconfigured to include several temperature sensors 302. These sensors would communicate and receive power over the same two-conductor bus. In this configuration, the temperature probe 300 can be lengthened so that it measures the temperature at a number of different locations in the roadway. Likewise, the temperature sensor 300 can be located vertically, so that its internal sensors measure the temperature profile of the road. In this way, the temperature probe 300 can be configured so that the three dimensional temperature profile of the roadway is gathered, with all of the data and power for this network being transferred over the same two-conductor bus.

FIG. 2 shows the relative size and location of the sample cup 16 as well as the locations of a sample well 20 positioned over the thermistor 24 and the two conductivity probes 22. The cross-sectional area A1 of the sample well 20 is substantially smaller than the cross-section area A2 of the sample cup 16 in the view of FIG. 2. Though not required, in this example the sample cup 16 has a generally triangular shape in plan view. This shape provides the space needed for the conductivity probes 22 and the thermistor 24 while minimizing the heat capacity of the sample cup 16 and the contained sample that must be cooled during an active cooling operation.

Figure 3:
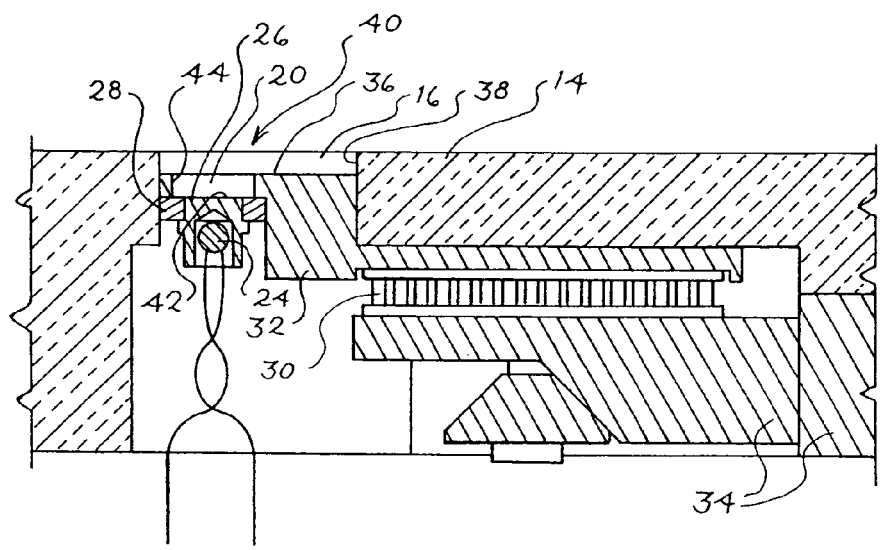
FIG. 3 is a fragmentary cross-sectional view taken along line 3—3 of FIG. 2.

FIG. 3 is a cross section through the center of the sample well 20. As shown in FIG. 3, the lower surface 36 of the sample cup 16 is formed by an aluminum plate that functions as a cold thermal link 32 with an active cooler 30, e.g., a Peltier cooler. The cold thermal link 32 is preferably formed of aluminum, because aluminum has a relatively high thermal conductivity and a relatively low heat capacity. The purpose of the cold thermal link 32 is to transfer heat into or out of the solution in the sample cup 16, and a high thermal conductivity enhances the performance of the cold thermal link 32. Similarly, a low heat capacity for the cold thermal link 32 improves the response time of the link 32. The sample cup 16 also includes a surface 38 that is formed by the insulating material of the cover 14. Thus, the sample cup 16 is formed as an opening 40 in the cover 14. A hot thermal link 34 is provided on the opposite side of the active cooler 30 from the cold thermal link 32, and the hot thermal link 34 is used to transfer heat from the active cooler 30 to the environment.

As also shown in FIG. 3, the sample well 20 is positioned immediately over a housing 26 that mounts the thermistor 24. A first surface 42 of the sample well 20 is in good thermal contact with the housing 26 and, therefore, with the thermistor 24. A second surface 44 of the sample well (which preferably extends around at least one half of the circumference of the well 20, more preferably around 75% of the circumference of the well 20, and most preferably around the entire circumference of the well 20) is in good thermal contact with the cold thermal link 32. In particular, the thermal conductivity of the cold thermal link 32 closely adjacent the second surface 44 of the sample well 20 is preferably greater than 1 W/m·K, more preferably greater than 5 W/m·K, more preferably greater than 50 W/m·K, and most preferably greater than 100 W/m·K. The cold thermal link 32 may have a thin layer with a lower thermal conductivity (e.g., a corrosion layer) immediately adjacent the second surface 44 without materially adversely affecting heat flow from the sample in the well 20 to the cold thermal link 32, and the conductivity values given above are for the bulk material of the cold thermal link 32. The thermistor 24 is thermally isolated from the cold thermal link 32 by an insulating washer 28. This arrangement isolates a small portion of the liquid that is being frozen in a freeze point detection run. The liquid in the sample well 20 is in good thermal conduct with the thermistor 24, and it is also in good thermal contact via the second surface 44 with the cold thermal link 32. In this example, the second surface 44 completely surrounds the sample well 20 on all sides. The thermistor 24 is less strongly linked to the cold thermal link 32 because it is partially insulated by the washer 28.

In this example, the thermistor housing 26 is formed of aluminum having a thermal conductivity of about 200 W/m·K. The use of aluminum reduces the thermal mass of the housing 26 and decreases the response time of the thermistor.

Though not shown in FIG. 3, the leads for the thermistor 24 are preferably tightly wrapped around the outside of the thermistor housing 26, typically about three times. This provides a heat sink for the leads. Since the leads are typically made from a highly thermally conductive material such as copper, heat sinking them to the conductive housing 26 mitigates any heat flow through them. This reduces the flow of heat to the thermistor 24 via the leads and reduces erroneously high temperature measurements.

Also not shown in FIG. 3 is a potting material that is added to the area below the thermistor 24. In this example, the complete area beneath the thermistor 24 is filled with a high strength, low thermal conductivity epoxy. This fixes the location of all of the components, adds strength to the cover 14, and reduces leaks.

Figure 4:
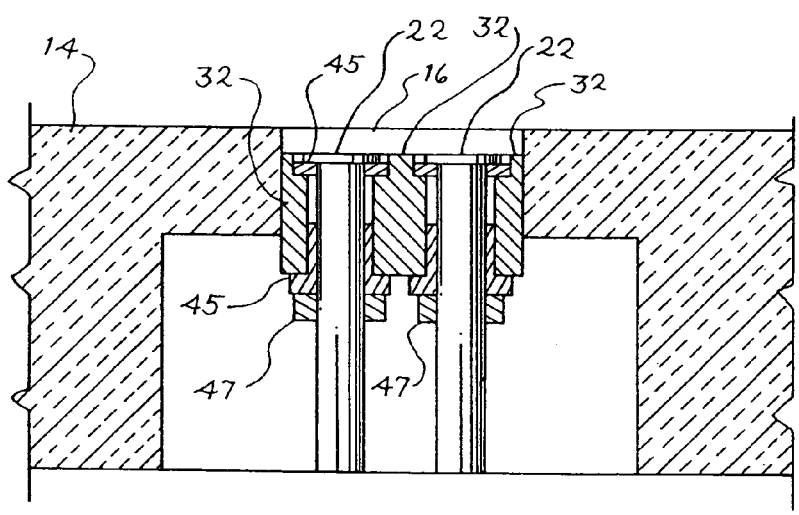
FIG. 4 is a fragmentary cross-sectional view taken along line 4—4 of FIG. 2.

FIG. 4 provides a cross section through the center of the conductivity probes 22. These probes 22 are electrically and thermally isolated from the cold thermal link 32 that forms the bottom of the sample cup 16 by a thermally and electrically insulating washer 45 at each end of each conductivity probe 22. The conductivity probes in this example are held in place by attachment nuts 47. The entire assembly is then encased by the epoxy potting material described above.

Many materials can be adapted for use in the module 10. By way of example, the materials of Table 1 have been found suitable.

TABLE 1

| Element Suitable | Material and Dimension |
|---|---|
| Cover 14 | MDS filled Nylon 6/6 |
| Probes 22 | Stainless Steel |
| Housing 26 | 6061-T6 Aluminum |
| Washer 28 | Nylon 6/6, 0.063 inch thick |
| Cold Link 32 | 6061-T6 Aluminum, 0.063 inch thick |
| Hot Link 34 | 6061-T6 Aluminum |
| Epoxy | Scotch-Weld 1838-L B/A Epoxy |

The sample well 20 captures a small amount of the liquid that is in the sample cup 16. This well 20 enhances heat flow into the water directly above the thermistor 24, by lessening the distance between the cold thermal link 32 and this sample of water.

The use of a thermistor well 20 has other benefits, in addition to better thermal conduction. The cold thermal link 32 cools much more rapidly than the water directly over the thermistor 24. This promotes freezing of the water over the link 32, which then provides seed crystals, allowing the water over the thermistor 24 to freeze with less supercooling. This pre-freezing of the water over the link 32 provides another advantage in that it protects the sample in the thermistor well 20 from splashes created by passing vehicles.

Description of the Electronics of the Module 10

In this non limiting example, the sensor module 10 includes the following major components.

Controller

Figure 13A:
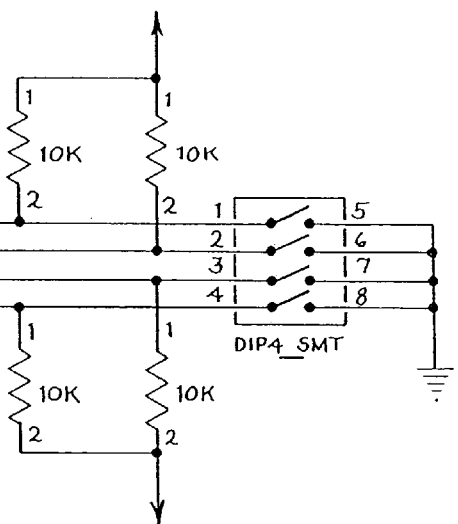
FIGS. 13–19 are schematic diagrams of electrical circuits included in the sensor module of FIG. 1.
Figure 13B:
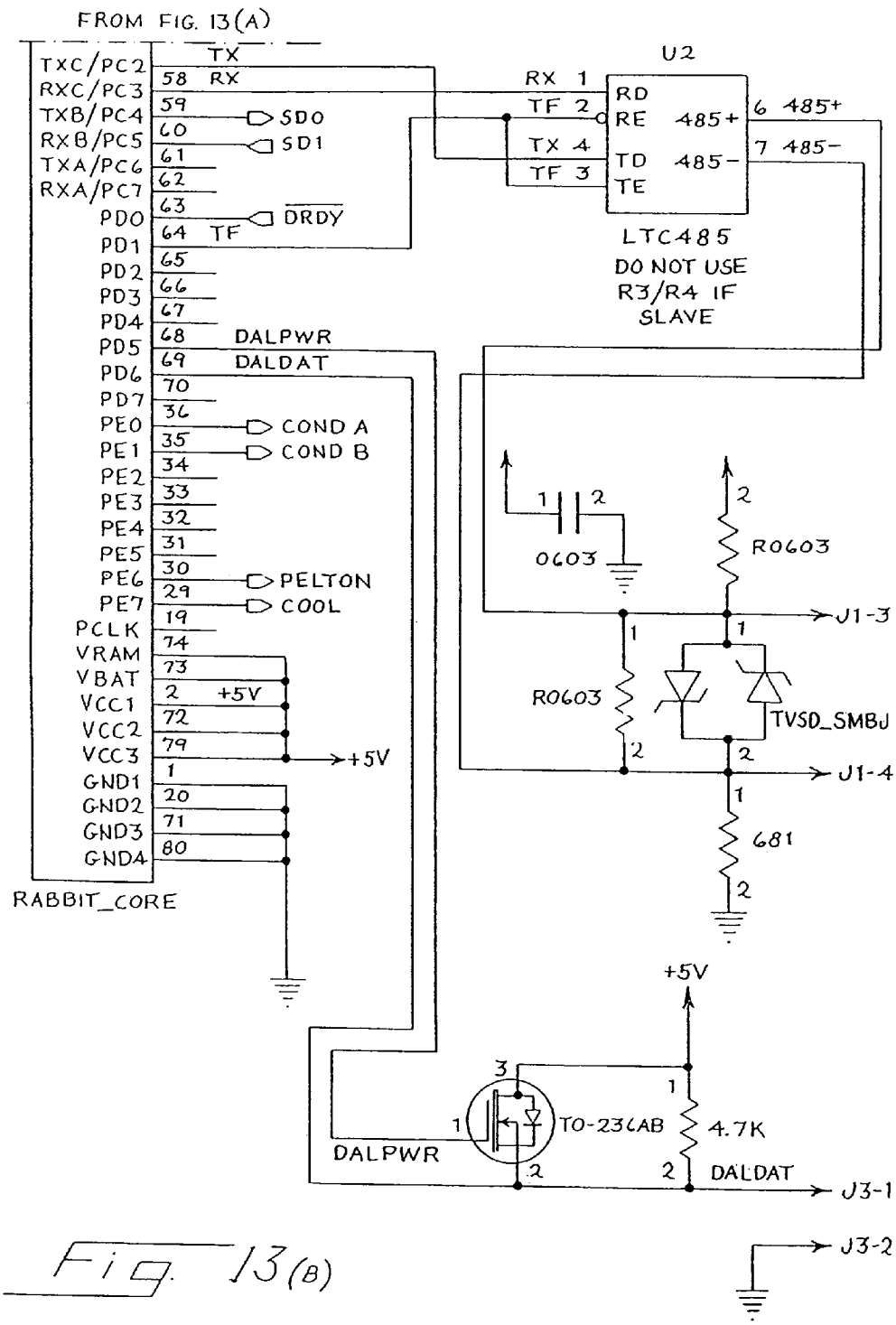

A programmable controller provides the control and analysis capability to the system. It includes an 8-bit microprocessor running at 18.432 MHz, 256K of flash memory, and 128K of RAM. The controller may be implemented as a Z-World Rabbit Core, Model RCM 2020, programmed via Dynamic C (FIG. 13). The controller is responsible for monitoring the road temperature, road moisture, and sample cup temperature. It also calculates the freeze point of liquid on the roadway and whether it is appropriate to issue a dew or frost warning. It communicates to the master controller via the daughter board's RS-485 transceiver.

The controller can execute the program of attached Appendix 1. Appendix 1 is made up of ASCII records of the following format: :NNAAAATTDD$_1$DD$_2$DD$_3$ . . . DD$_N$CC The colon starts every record. Each letter represents a hexadecimal nibble with the following meanings.

NN—Number of data bytes in record. For Dynamic C generated hex files, this is always either 02 for extended address records, 20 for data records, or 00 for EOF records.

AAAA—16 bit address. This is the offset portion off the destination address using the Intel real-mode addressing. The segment portion of the real-mode address is determined from the extended address record in the file previous to the data record. The physical offset into the memory device is computed by shifting the segment left 4 bits and adding the offset.

TT—Type of record. For Dynamic C generated hex files, this is always either 02 for extended address records, 00 for data records, or 01 for EOF records.

DD$_i$—Data byte

CC—8 bit checksum of all previous bytes in the record. The two's complement of the checksum is used.

Appendix 1 includes copyrighted material, and the copyright holder hereby reserves all rights in Appendix 1, other than the right to reproduce Appendix 1 as part of this specification.

Daughter Board Electronics

Figure 16:
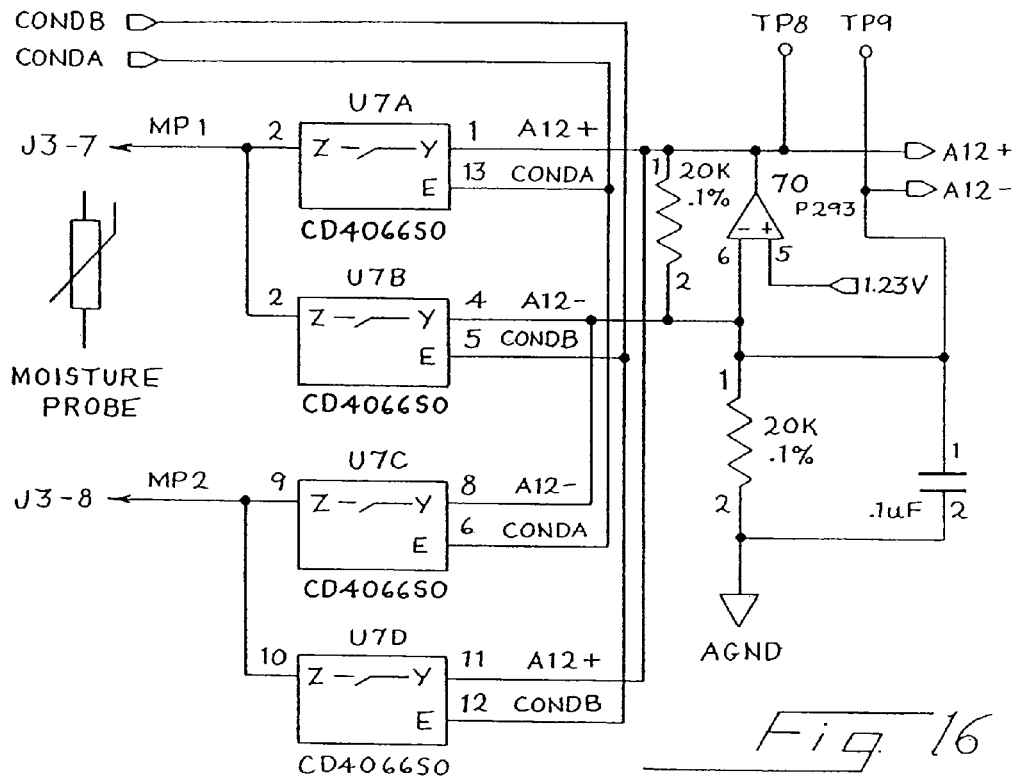
Figure 17:
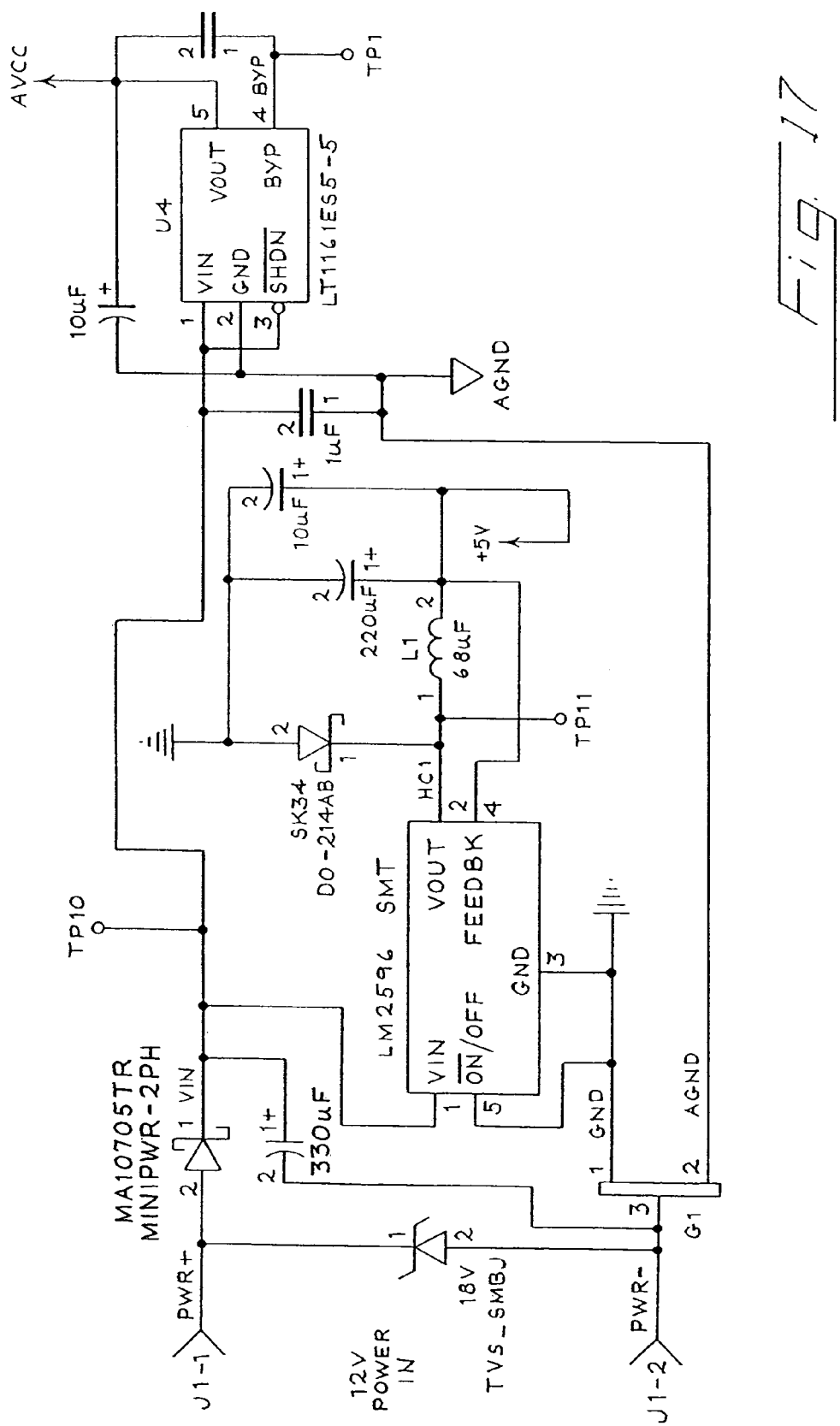

The daughter board electronics include an A/D converter, current drivers for the sensor thermistor and conductivity probes (FIGS. 14, 16, 18 and 19), an RS-485 transceiver circuit, a dip switch array to allow each sensor to have an address, a drive circuit for the Peltier cooler (FIG. 15), and power regulators to regulate the incoming voltage (FIG. 17). Also included on the daughter board is an interface circuit (FIG. 13) to external two-conductor digital temperature sensors. These temperature sensors can be used to measure the road surface temperature and if necessary other parameters, such as the subsurface temperature.

Sensor Cup Temperature Measurement

Figure 14:
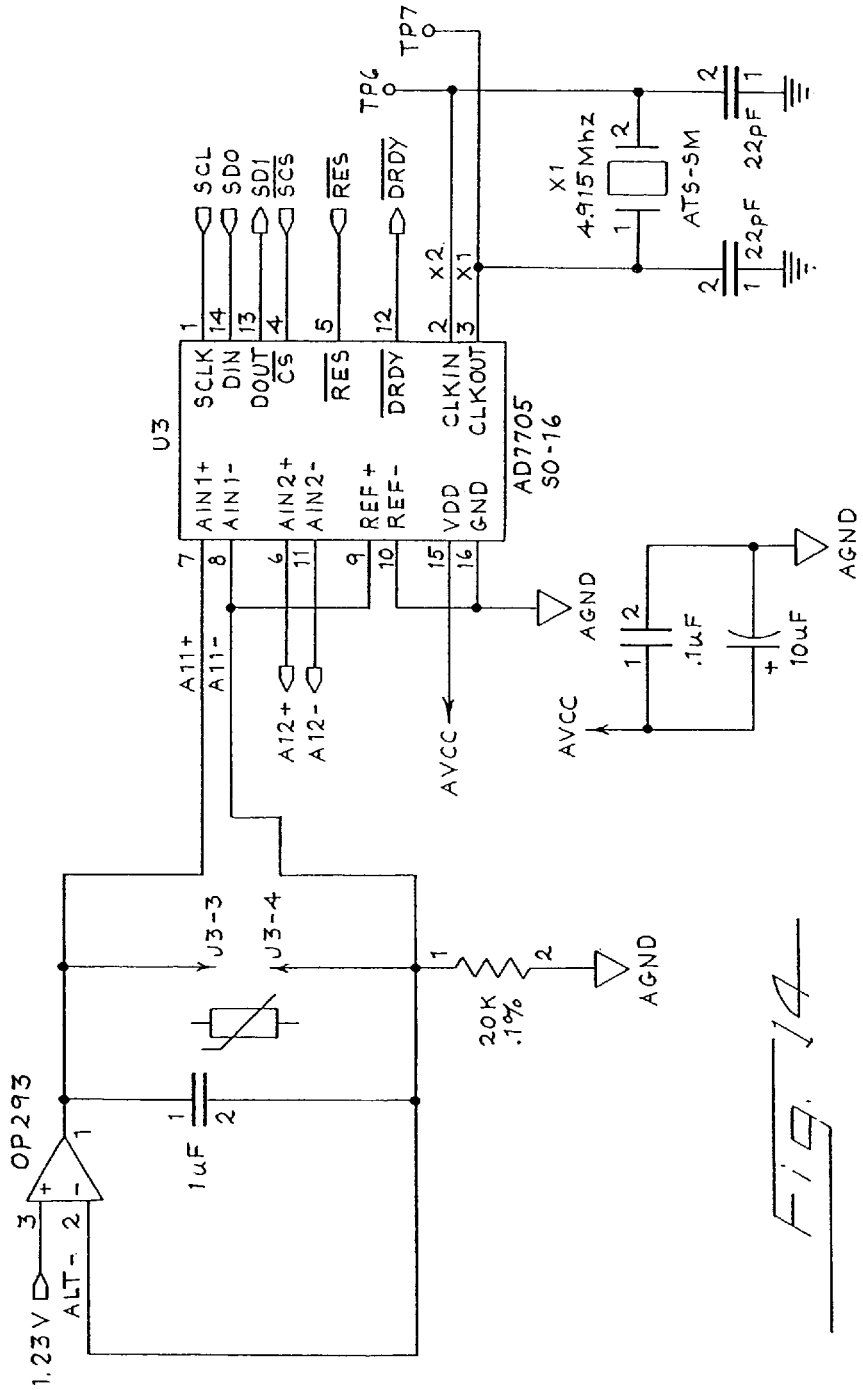
Figure 18:
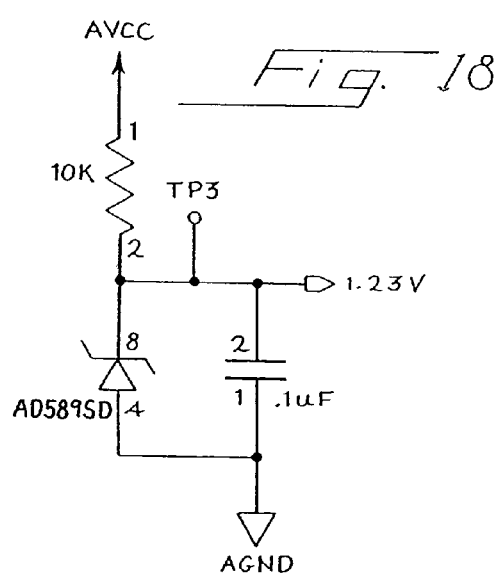
Figure 19:
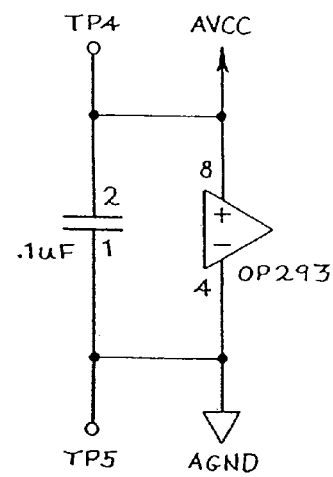

The daughter board measures the sample cup thermistor 24 via a precision current driver and a 16-bit A/D converter (FIGS. 14, 18 and 19).

External Two Conductor Temperature Measurement

In this non-limiting example, external temperatures are measured using Dallas Semiconductor Corporation's digital two conductor temperature sensors (known as "1-wire sensors"). These sensors are an example of two-conductor sensors because they only require two conductors to transmit both data and power. These sensors derive their power from the data line, whenever it is held in its high state. Additionally, each of these sensors has its own globally unique address. This means that many sensors can be placed on the same two-conductor bus. Also, since the sensors are digital, they can be located remotely (up to and even more than three hundred meters) from the host sensor.

These three features (a simple two-conductor bus, globally unique addresses, and digital communication) give these sensors an economic advantage over more traditional sensing techniques, such as individually connected sensors. For instance, a series of five of these sensors can be used to measure the temperature of the road at five different depths. Another application is the measurement of the road surface temperature at a number of locations. More traditional sensors each require their own wires and their distance from the host sensor is limited if they produce analog signals. Digital sensors exist that communicate over a bus, but a method is required (i.e., an address) to differentiate the sensors. These sensors also typically require separate power circuits. The amount of wire and the number of conductors required are a significant part of the design as the cost of wire for long runs can exceed that of the sensors that are at the end of the wire.

Electrical Conductivity Measurement

The resistance between the two conductivity probes 22 is measured via a precision current driver and the second channel in the 16-bit A/D converter (FIG. 16). This circuit measures the conductivity of any liquid that is present in the sensor cup 16. The drive current between the probes 22 is reversible via an analog switch, limiting the polarization of the conductivity probes 22 and the liquids on their top surface. This circuit has shown that it can differentiate between a dry surface, a surface lightly coated with distilled water, and a surface covered with a salt solution.

Peltier Power Circuit

Figure 15:
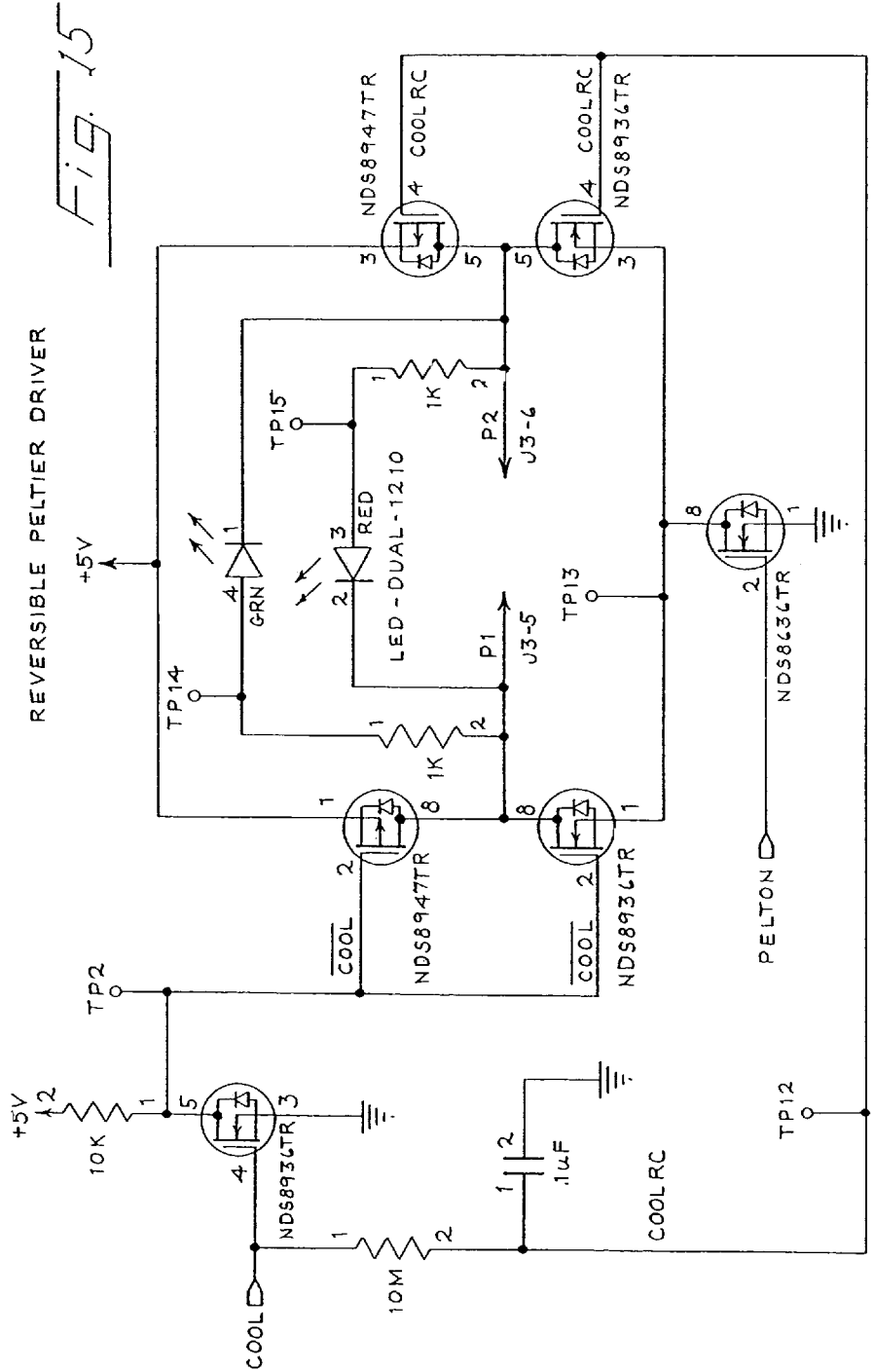

The Peltier power circuit turns on the Peltier cooler 30, as directed by the controller (FIG. 15). Included in this circuit is an H-bridge to allow the Peltier cooler 30 to be heated or cooled, as appropriate.

Sensor Measurement Capabilities

The following four parameters are measured by the sensor module 10:
  road surface temperature,
  road surface moisture conductivity,
  temperature of a sample of liquid in the sample well 20,
  subsurface temperature (optional).

These parameters are used by the controller to determine the freeze point of liquid in the sample well, as well as to provide dew and frost warnings.

Freeze Point Algorithm

During the determination of the freeze point, the onboard controller stores the temperature of the liquid in the sample cup versus time. This data is then analyzed to determine the freezing temperature of the liquid, as described below. The algorithms described below assess the shape of the resulting freezing curve, and surface conductivity is used as a verification of the freezing of the sample.

Dew Warning Algorithm

If the ambient temperature is near freezing and the road is dry, the Peltier cooler can cool the sample by several degrees. If moisture is then detected, the sensor will give a dew warning, indicating the impending formation of dew, and possibly black ice.

Frost Warning Algorithm

If the ambient temperature is below freezing and the road is dry, the Peltier cooler can cool the sample cup by several degrees. It can then be heated back to the ambient temperature. If moisture is then detected, the sensor will give a frost warning, indicating the impending formation of frost.

Description of Methods to Determine the Freeze Point

The following section describes the method used by the sensor module 10 to detect the freeze point of a liquid. This method searches for a constant temperature condition that exists during freezing. It does this by continuously fitting a series of lines to the temperature versus time data. It also continuously monitors the electrical conductivity of the water to determine if freezing has occurred.

Discussion of the Data Gathered

Figure 5:
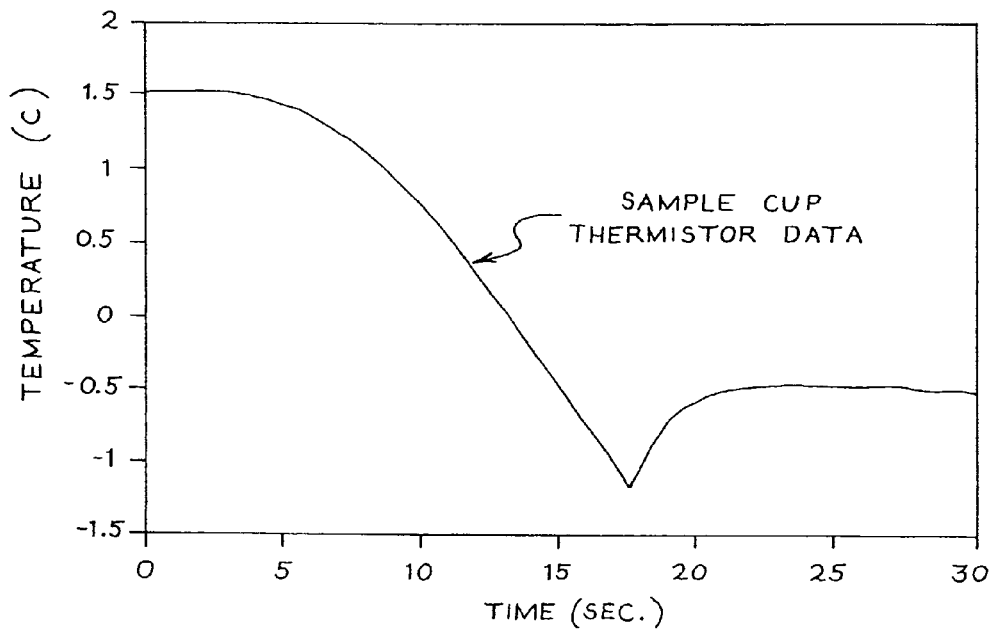
FIGS. 5, 6, 7 and 8 are graphs illustrating operation of the sensor module of FIG. 1.

As described above, this method makes use of the fact that the cooling curve of a freezing liquid is nearly level. FIG. 5 shows a cooling curve for a liquid whose freezing temperature is near −0.5° C. This data was obtained during an actual freeze point detection run with the sensor module 10. The cooling curve in FIG. 5 is nearly level between zero and five seconds as the Peltier cooler 30 works to cool the thermal mass of itself, the cold thermal link 32 and the sample of liquid in the well 20. There is also a delay in the response because the thermistor 24 is not strongly linked to the Peltier cooler 30. At about five seconds, the curve begins to trend downwards, until at about ten seconds, where it has reached a nearly constant slope. The curve continues at this constant slope until about 17.5 seconds. At this point, the liquid has been supercooled to −1.2° C., which is below its nominal freezing temperature of −0.5° C. The cooling curve then slopes upward until about 21 seconds, where it levels off around the freeze point of −0.5° C.

Figure 6:
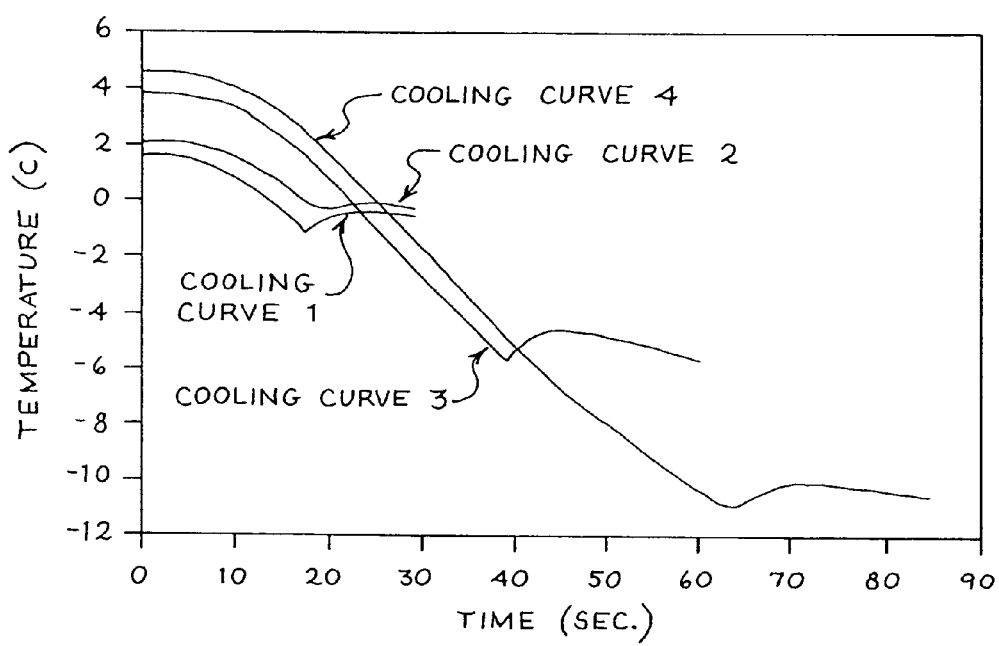

It should be noted that there are variations to the shape of the cooling curve, as described above and shown in FIG. 5. As an example of this variation, FIG. 6 shows four cooling curves, measured with the sensor module 10. The cooling curve shown in FIG. 5 is labeled "Cooling Curve 1" in FIG. 6. In three of the cases shown in FIG. 6 (cooling curves 1, 3, and 4), the cooling curves show the liquid being substantially supercooled, prior to solidification. Cooling curve 2, however, shows very little supercooling, prior to the leveling out which is indicative of freezing. Solidification without substantial supercooling has been observed under a variety of conditions with liquids having a range of freezing temperatures.

FIG. 6 also shows the different slopes the cooling curve can take, once solidification has begun. For cooling curves 1 and 2, which are nearly pure water, the curves are nearly level, once solidification has begun. For cooling curves 3 and 4, which were gathered from salt solutions that differ in both type and concentration, the cooling curves slope downwardly during solidification. This is because the water in a solution freezes first, increasing the concentration and lowering the freezing point of the remaining solution.

It should be noted that the shapes of the curves, including the slopes, the amount of supercooling, and the temperatures obtained during freezing, are highly dependant upon the design of the sensor itself. For example, changing the heat capacity, conductivity, or geometry of any of the components, or changing the Peltier cooler 30 or the characteristics of the Peltier cooler power source, will change the shape of the curves observed. There are numerous other changes that can be made to the design of the sensor that will change the shape of the cooling curves.

Figure 7:
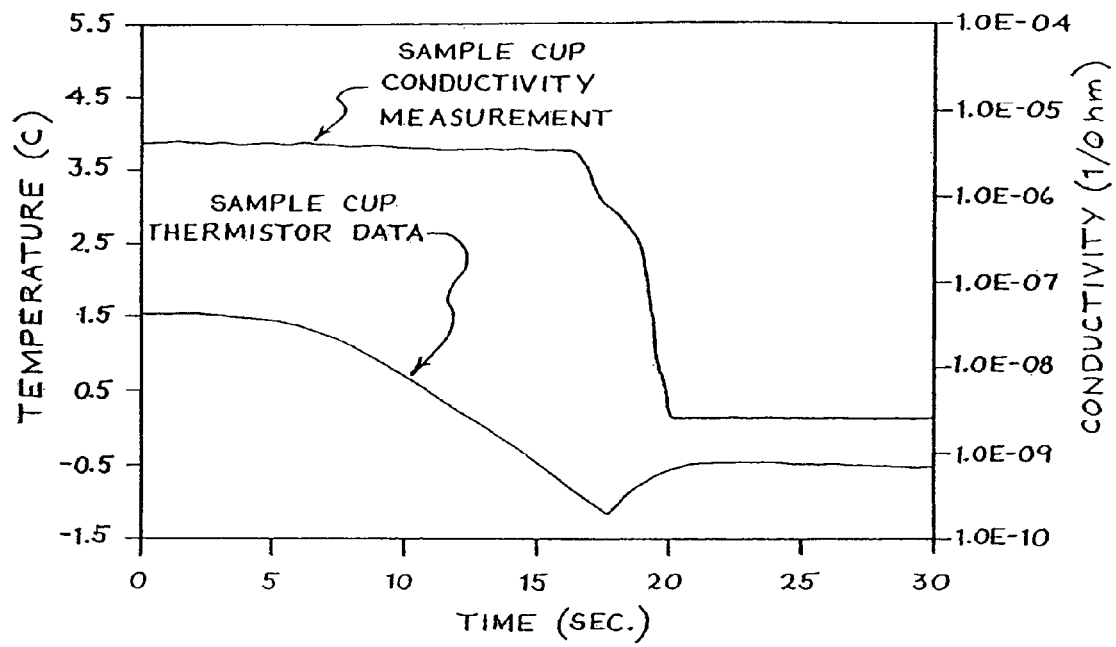

FIG. 7 compares the cooling curve of FIG. 5 with the measurements made by the pavement sensor's conductivity probes 22. The actual values of the conductivity are dependant upon many factors, including the temperature, the solution type, the geometry and construction of the conductivity probes 22 and for how long they are sampled. What is significant about the conductivity data in FIG. 7 is that the conductivity of the solution falls significantly during solidification.

Presently Preferred Algorithm

Figure 8:
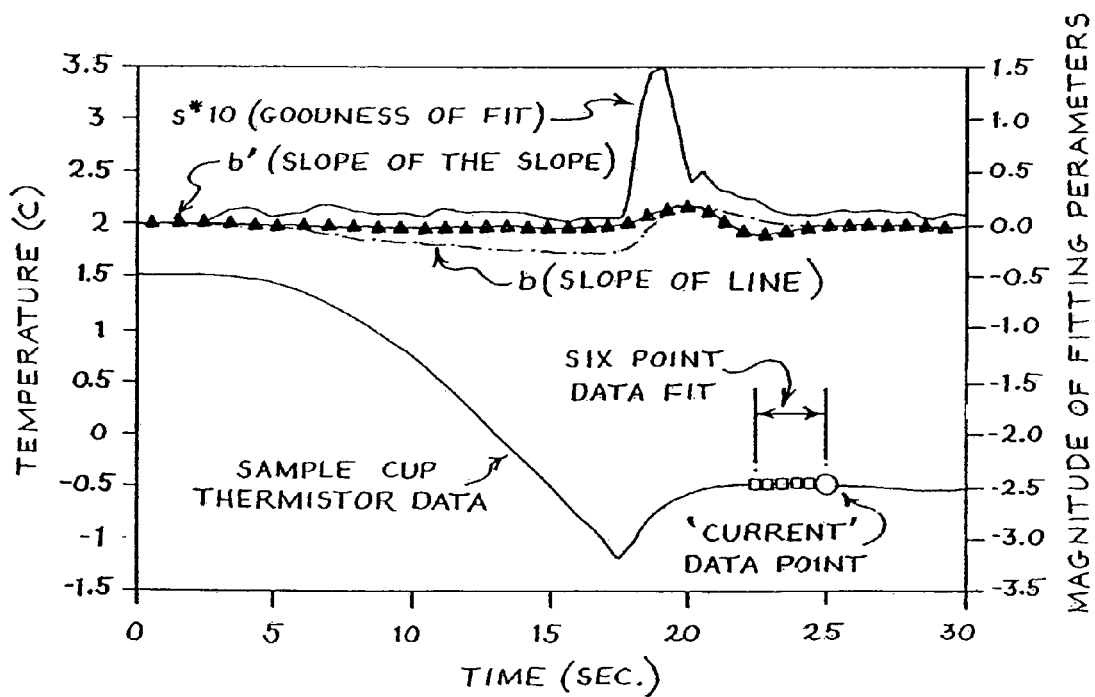

The freeze-point detection algorithm analyzes the temperature versus time data acquired from the thermistor 24 by fitting a series of lines to the preceding six data points. FIG. 8 shows the output from this curve fitting routine. The sample cup thermistor data that is shown is the same as was shown in FIGS. 5, 6, and 7. Six of the data points in this line are highlighted to represent the points that would be used for one of the line fits. The last of these points, at 25 seconds, represents the most current data point in this line fit. Once the line has been fit, a second line is formed from the slopes of the preceding six line fits. This results in a trend of the previously calculated line slopes, or a "slope of the slope."

The three upper lines in FIG. 8 represent the slope of the line, b, the scatter of the line fit, s*10, and the "slope of the slope", b'. The parameters are compared to preset values to make a determination of freezing. Two separate algorithms are run simultaneously to make this determination. The first of these looks for a positive slope in the cooling curve to indicate warming due the release of latent heat. The second of the algorithms does not require a positive slope, but instead looks for a significant change in the slope as given by b', the "slope of the slope."

The conductivity measurement is used as a verification that freezing has occurred. Use of the conductivity alone as an indicator of freezing would result in an unreliable measurement. This is because the conductivity probes are not necessarily the same temperature as the water in the thermistor well. The measured conductance can be used as verification.

The slope b can be taken as an example of a first time derivative of the temperature measurements, and the slope of the slope b' can be taken as an example of a second time derivative of the temperature measurements.

Description of the Algorithm

The following paragraphs describe the actions that are taken by the sensor algorithm to determine the freeze point of a liquid in the thermistor well.

1. Take a current sample cup temperature reading.

2. Fit a line to the last 6 sample cup temperature data points using linear regression. The line has the equation $$T = a + b \cdot t,$$

where a and b are constants, T represents temperature, and t represents time. The fitting equations for the constants a and b are as follows:

$$b = \frac{\sum (t - \bar{t}) \cdot (T - \bar{T})}{\sum (t - \bar{t})^2}$$

and $$a = \bar{T} - b \cdot \bar{t},$$

where $\bar{t}$ and $\bar{T}$ are the average values of t and T for the six data points being used.

The goodness of fit, s2, is computed by the equation $$s^2 = \frac{\sum T^2 - a \cdot \sum T - b \cdot \sum t \cdot T}{(m - 2)},$$

where m is the number of data points used in the fit. This line fit statistic is reduced to the "s*10" statistic for convenience in the algorithm by the relation, $$s \cdot 10 = 10\sqrt{s^2}.$$

3. Compute the "slope of the slope" by fitting a line to the last 6 line slopes obtained, using the following formula:

$$b' = \frac{\sum (t - \bar{t}) \cdot (b - \bar{b})}{\sum (t - \bar{t})^2},$$

where b' is the "slope of the slope" and the values of b are the slopes from the last 6 fitted lines.

4. Determine from the fitting constants whether the freezing temperature has been reached. For the sensor module 10, the following rules were applied to the fitted line constants to determine when the freezing temperature had been reached. These rules were based on the characteristics of this particular device. Other devices would most likely have different values for these criteria. Two methods are currently used simultaneously, one that looks for a transition in the curve due to a supercooled fluid and one that assumes no appreciable supercooling.

4.1. For the supercooling routine, no data is considered for the first seconds, so that only reliable fits are considered. After this, the current slope is constantly monitored. When the slope rises above 0.5, a logical variable "Freeze_Start" is set to TRUE, indicating that freezing has begun. This indicates that subsequent line fits should be considered as possible plateaus in the freeze curve. It also sets the Peltier cooler 30 at a reduced power setting, where the Peltier cooler 30 is switched on and off. In the current design, the Peltier cooler 30 is set at a duty cycle of 50 percent once freezing has begun.

4.2. For the non-supercooling routine, no data is considered for the first 10 seconds. This allows for reliable fits and also eliminates the initial level portion of the freeze curve. After this, the current slope is constantly monitored. When the slope is greater than −0.1, a logical variable "Slope- _Start" is set to TRUE. This indicates that freezing may have begun, however the Peltier cooler 30 continues at full power. Next the b' parameter, or slope of the slope, is checked. When this parameter is greater than 0.05, freezing is determined to have begun and the "Freeze_Start" variable is set to TRUE. Subsequent line fits are then considered as possible plateaus in the freeze curve and the Peltier cooler 30 is set a reduced power setting, as is described at 4.1.

4.3. Once one of the above conditions has been met (and "Freeze_Start" has been set to TRUE), the parameters of the current line fit are checked to see if they fall within preset bounds that are indicative of freezing. Currently a value of s*10 that is less than 0.5 and a value of b greater than −0.12 and less than or equal to 0.0 are used to indicate that the plateau has been reached. Testing for values of b in this range are to be understood as one way of testing whether the cooling curve T(t) has leveled off. Thus the term "leveled off" is intended to include slopes of T(t) that are somewhat negative, such as the slopes characteristic of freezing of a salt solution. However, large negative slopes, such as those associated with active cooling after a splash of water has entered the sample well, are excluded.

4.4. If the parameters of step 4.3 are met, the sensor module 10 uses the first data point in the line fit as the determined freeze point. This ensures that the highest temperature is used for concentrated solutions that have a steep freezing curve.

Referring again to FIG. 8, the decisions that the algorithm makes are shown in the timeline of Table 2. For simplification; an "x" in Table 1 has replaced data that is not relevant to a particular algorithm step.

TABLE 2

| Time (sec.) | Temp. (C.) | b | S*10 | b' | Algorithm Action |
|---|---|---|---|---|---|
| 5.0 | 1.4 | −0.04 | x | x | Initial data has been gathered. Line slopes begin to be reviewed for freezing by the "Supercooled" algorithm. The current line slope does not indicate that the latent heat from supercooling is being released. Freeze_Start remains FALSE. |
| 10.0 | 0.7 | −0.18 | x | −0.03 | Initial data has been gathered and the sensor has been given enough time for a down slope to begin. The "Non-supercooled" algorithm begins to check for leveling off which would be due to freezing. The current b' does not indicate freezing, so Slope_Start remains FALSE. The "Supercooled" algorithm continues to check for a freeze point. The current line slope does not indicate that the latent heat from supercooling is being released. Freeze_Start remains FALSE. |
| 18.5 | −0.9 | −0.06 | 1.46 | 0.07 | The slope is greater than −0.1, so the "Non-supercooled" algorithm sets Slope_Start to TRUE. The value of b' is also greater than 0.05, so the Non-Supercooled algorithm also sets Freeze_Start to TRUE, causing the Peltier to lessen its cooling. Because Freeze_Start is TRUE the detection algorithm checks for |

TABLE 2-continued

| Time (sec.) | Temp. (C.) | b | S*10 | b' | Algorithm Action |
|---|---|---|---|---|---|
| | | | | | a plateau, but ignores this data point, because the s*10 value indicates that the data has a high amount of scatter. |
| 17.0–20.0 | X | x | x | x | The conductivity of the sample above the cooling plate goes high (see FIG. 7), indicating that freezing in the thermistor well is imminent |
| 25.0 | −0.5 | 0.00 | 0.10 | x | The line slope (b) is reduced to zero and the s*10 scatter is less than 0.5, so detection algorithm logs the first data point in the line fit, −0.47° C., as the determined freeze point. |

Figure 9:
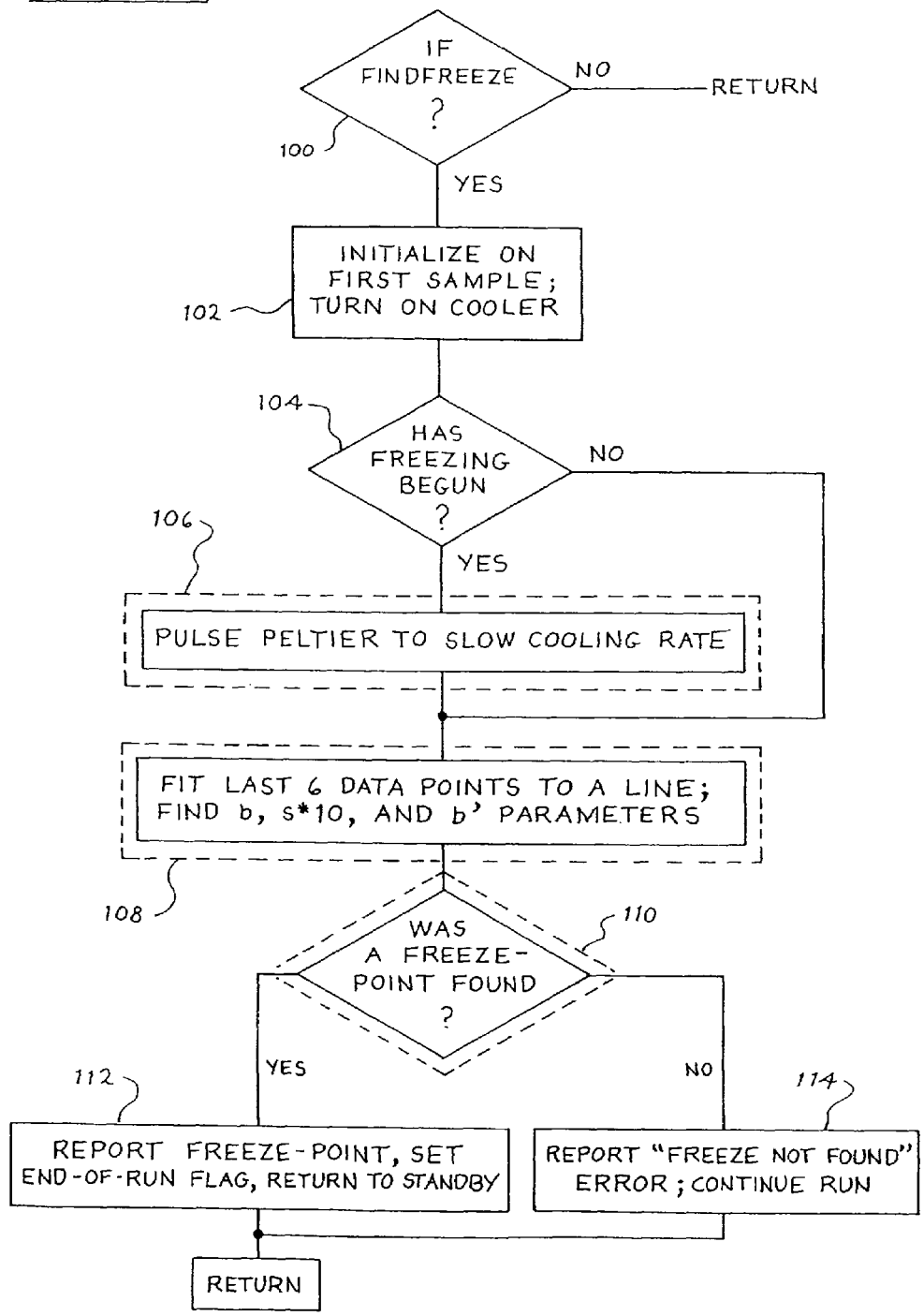
FIG. 9 is a flow chart of a software routine included in the sensor module of FIG. 1.
Figure 10:
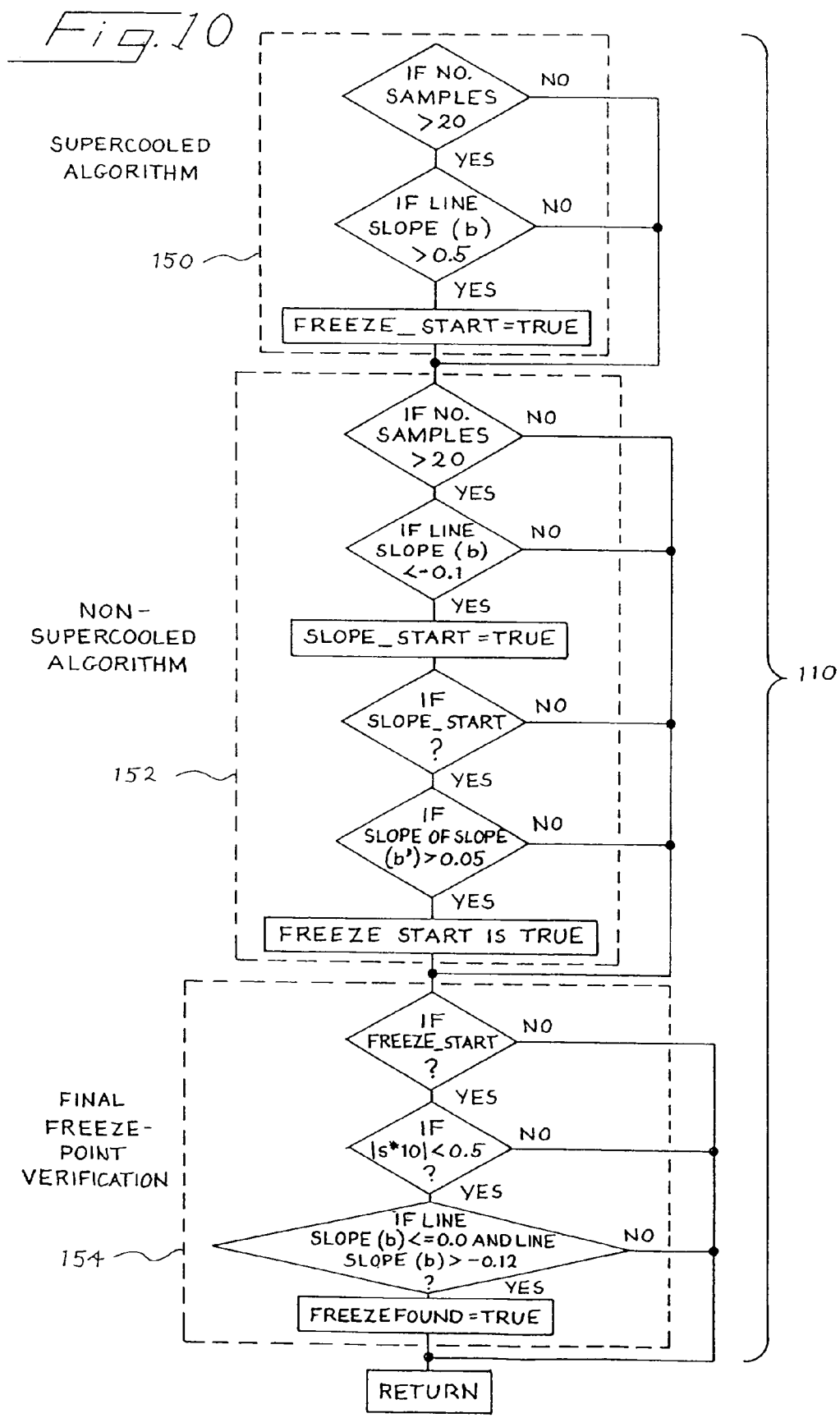
FIG. 10 is a more detailed flow chart of block 110 of FIG. 9.

FIGS. 9 and 10 provide flow charts of software routines that implement the freezing point detection algorithms discussed above. The routine of FIG. 9 first checks the logical variable FindFreeze. If the ambient road temperature is within an operational range, e.g., between +5 and −15° C., and if the surface conductivity indicates the presence of water, the parameter FindFreeze is set to TRUE. Only in this case is control transferred to block 102, in which the active cooler 30 is turned on to begin cooling liquid in the sample cup 16 and the sample well 20. The temperature indicated by the thermistor 24 is read repeatedly, and once it has been determined that freezing has begun, the active cooler 30 is operated at a slower cooling rate, e.g., at 50 percent duty cycle, in block 106. In block 108 the last six temperature measurements are fit to a line and the parameters b, s*10, and b' discussed above are calculated. These calculated parameters are then analyzed in block 110 to determine whether a freeze point was found, and the result is reported in blocks 112 and 114. If a freeze point is found, the cooler 30 is turned off. If the freeze point is substantially lower than the ambient temperature, the cooler 30 will continue to cool until it cools below the minimum cooling temperature (e.g., −15° C.). At this point, the controller will turn off the cooler 30 and discontinue the freeze-point detection run. The minimum cooling temperature is then returned as the freeze point. The controller will also stop the run if the measured temperature provided by the thermistor 24 falls more than 10 degrees below the ambient temperature. If there is substantial splashing by passing vehicles, the sensor module 10 may need extra time to complete the freeze-point detection run. If a freeze-point detection run is not completed within the time specified by a stored constant (e.g., 5 minutes), the controller will turn off the active cooler 30 and discontinue the run. The controller will continue to return the last detected freeze point until the master controller has indicated that it has received this value by returning a normal data request instead of a find freeze point request.

FIG. 10 provides further information as to operation of block 110 of FIG. 9. In block 150, variable "Freeze_Start" is set to TRUE if the number of samples is greater than 20 and if the line slope b is greater than 0.5. These conditions are typically met when a supercooled liquid begins to freeze. In block 152, the logical parameter "Freeze_Start" is set to TRUE if the number of samples is greater than 20, the line slope b falls to a value below −0.1 and then the slope of the slope b' rises to a value above 0.05. These conditions are typically met by the initiation of freezing in a non-supercooled liquid. In block 154, the parameter "Freeze_Start" is checked, and if it is in the TRUE state, the parameter s*10 is checked and the line slope b is checked to determine whether it is less than zero and greater than a negative threshold (−0.12 in this non-limiting example). If so, the logical variable FreezeFound is equal to TRUE. The parameters checked in block 154 are characteristically met when a freezing sample reaches a temperature plateau that is either level or tending downward slightly.

Though not required, the method of FIGS. 9 and 10 can be supplemented by checking the conductivity measurements around the time of freezing as indicated above. For example, if a conductivity measurement shows a sharp decrease in conductivity at about the time the freezing temperature is reached as indicated by the thermistor, this can be taken as a confirmation that in fact freezing has occurred.

As mentioned above, when the freezing point detection algorithm indicates that freezing has commenced, the earliest temperature measurement (which is typically the highest temperature) within the samples used to determine the slope b is selected as the freezing point temperature.

One method for measuring a liquid freezing point on a roadway includes a sensor module that is embedded in a roadway. The sensor module includes a measurement zone on an upper surface thereof a temperature sensor in good thermal contact with the measurement zone, and an active cooler thermally coupled to the measurement zone. The method progressively cools the measurement zone with the active cooler. The method records temperature measurements of the measurement zone with the temperature sensor repeatedly while the method progressively cools the measurement zone. The method determines a first time derivative of the temperature measurements that were recorded. The method determines when the first time derivative rises above a first, positive threshold value; and then determines when the first time derivative falls to within a range of values bounded above by zero and below by a second, negative threshold value. The method measures a liquid freezing point by associating an earliest temperature measurement included in a line associated with the first time derivative as the liquid freezing point.

Two Conductor Devices

Figure 11:
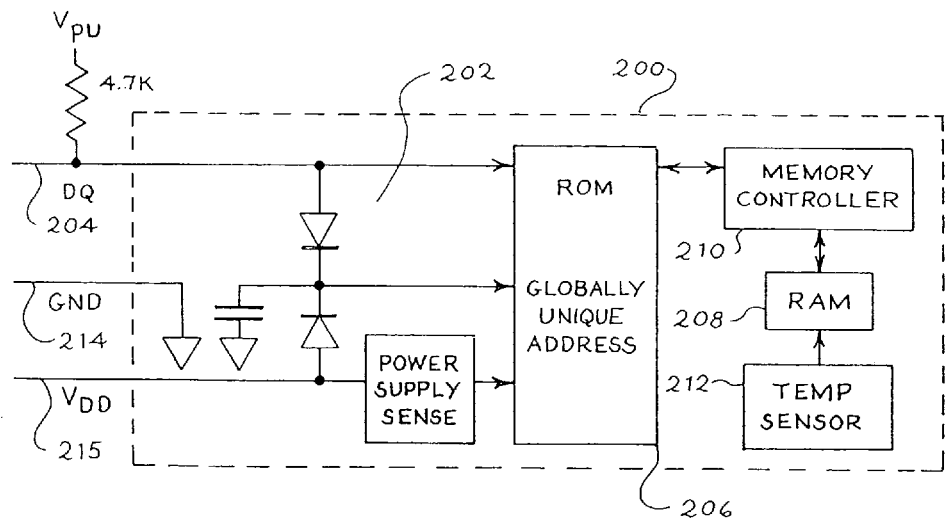
FIG. 11 is a block diagram of a two-conductor temperature sensor.

The two-conductor devices described above can be constructed as shown schematically in FIG. 11, and suitable devices can be acquired from Dallas Semiconductor Corporation, a subsidiary of Maxim Integrated Products, as Model No. DS18B20. In FIG. 11, a two-conductor device 200 includes a power circuit 202 that draws power from a conductor 204 and supplies this power to the remaining components of the device 200. The device 200 also includes a random access memory 208, a memory controller logic 210, and a temperature sensor 212. The read only memory 206 stores a globally unique address, e.g., a 64-bit address. The temperature sensor 212 operates to store a temperature measurement in the random access memory 208. The memory controller 210 transmits address information from the read-only memory 206 via the conductor 204 as well as temperature information from the random access memory 208 via the conductor 204. Both the address information and the temperature information are transmitted as serial, digital signals. Typically, a ground conductor 214 is also connected to the device 200, and the two conductors 204, 214 serve to transmit power to the device 200, digital signals to the device 200, and digital address and temperature signals from the device 200. Also shown in FIG. 11 is an alternate power conductor 215 that can also be used to power the device 200. If conductor 204 is used to power device 200, power conductor 215 is tied directly to ground conductor 214.

Figure 12:
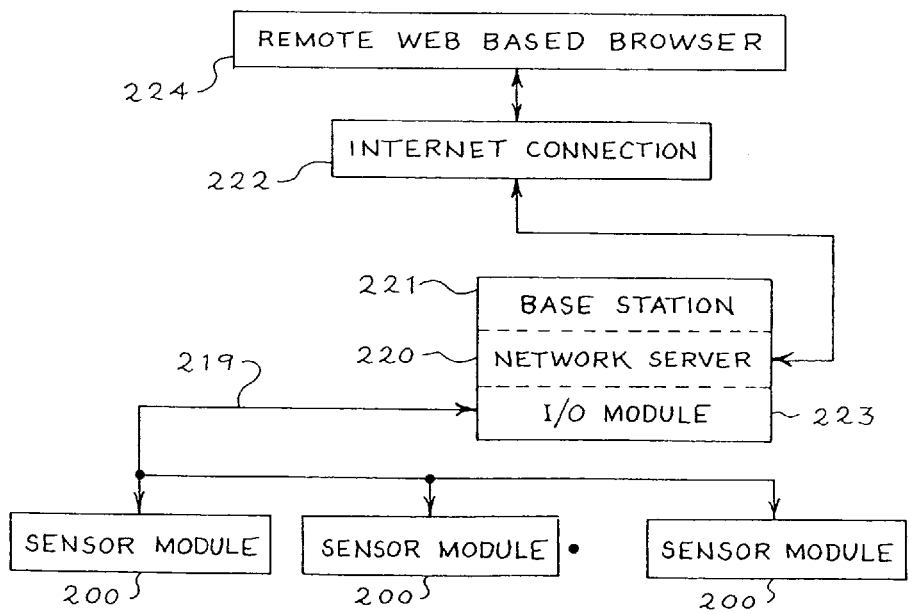
FIG. 12 is a block diagram of a temperature monitoring system including multiple sensor modules of the type shown in FIG. 11.

FIG. 12 shows one example in which many two-conductor devices 200 are connected via a two-conductor cable 219 to an I/O module 223 of a base station 221 that also includes a network server 220. The network server 220 is connected via an Internet connection 222 to a remote web-based browser 224, that will typically be implemented on a remote computer. The Internet connection 222 can take any suitable form, such as a wireless connection, a direct line connection, or a dial-up connection to an Internet service provider. The network server 220 and the devices 200 exchange both temperature information and address information as serial, digital signals on the conductors of the cable 219. As explained above, only two conductors are required to bring both power and digital signals to and from each of the devices 200.

In this example, the read-only memory 206, the random access memory 208, and the memory controller logic 210 operate as a means for transmitting temperature and address information from the device 200 to the network server 220. These components can be implemented in any desired fashion, and the present invention is not limited to any particular type of controller logic or memory. Similarly, the network server 220 operates as a means for transmitting temperature information from the base station that houses the network server 220 to the remote computer that houses the web-based browser 224. With this arrangement, the user can access via the Internet temperature information measured by any of the devices 200 of FIG. 12.

Many alternatives are possible. For example, other networks can be used in substitution for the Internet network described above. The Internet provides important advantages, in that it reduces the cost and inconvenience of remotely accessing information provided by the devices 200. The devices 200 are not limited to temperature measuring devices, and they can include other types of sensors, e.g., conductivity sensors and other sensors based on A/D converters, as well as counters of various types.

CONCLUSION

Figure 20:
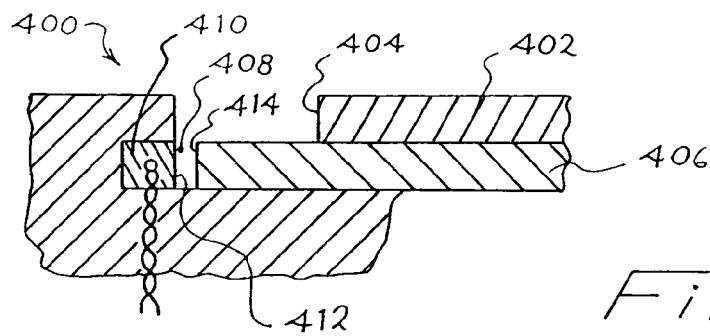
FIG. 20 is a fragmentary cross-sectional view taken along line 20—20 of FIG. 21.
Figure 21:
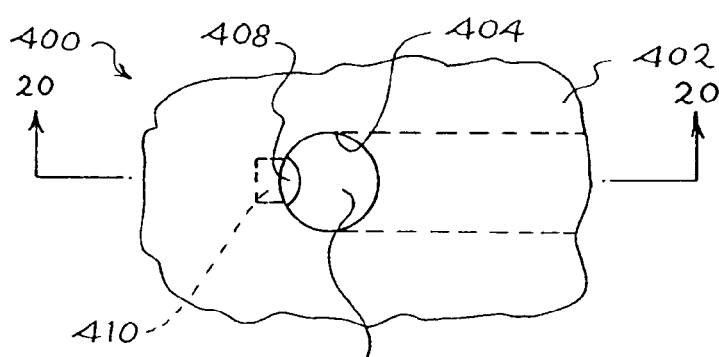
FIG. 21 is a fragmentary top view of an alternative sensor module.
Figure 22:
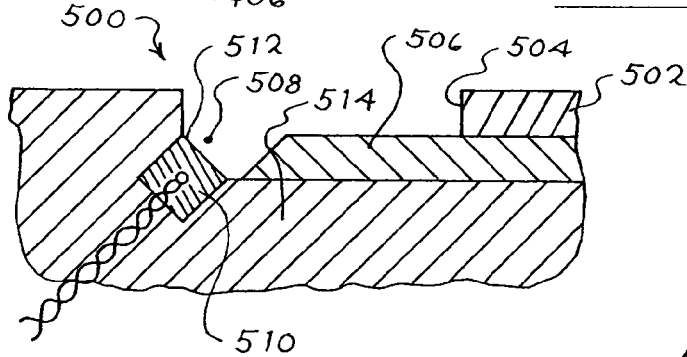
FIG. 22 is a fragmentary cross-sectional view taken along line 22—22 of FIG. 23.
Figure 23:
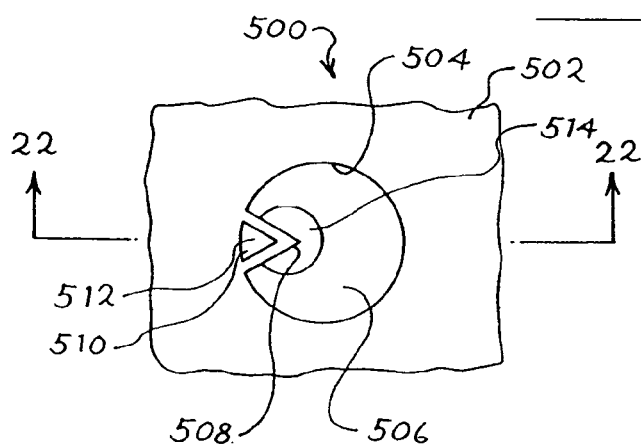
FIG. 23 is a fragmentary top view of another sensor module.

Of course, it should be understood that many changes and modifications can be made to the preferred embodiments described above. For example, many changes can be made to the shape of the sample well and adjacent elements. FIGS. 20 and 21 show cross-sectional and top views, respectively, of part of a sensor module 400 that includes a cover 402 having an opening 404 that defines a sample cup. A cold thermal link 406 forms the bottom of the sample cup, and the cold thermal link partially surrounds a sample well 408. A first surface 412 of the sample well 408 is in good thermal contact with a temperature sensor 410, and a second surface 414 of the sample well 408 is in good thermal contact with the cold thermal link 406. FIGS. 22 and 23 show corresponding views of a sensor module 500 having a cover 502 having an opening 504 that defines a sample cup. A cold thermal link 506 forms the bottom of the sample cup, and the cold thermal link 506 partially surrounds a sample well 508. A first surface 512 of the sample well 508 is in good thermal contact with a temperature sensor 510, and a second surface 514 of the sample well 508 is in good thermal contact with the cold thermal link. As should be apparent from these figures and FIGS. 1–3, the sample well can take many shapes, and the first and second surfaces can be oriented at various angles. The first and second surfaces can be planar, cylindrically shaped, or otherwise curved. For example, the first and second surfaces may be separate parts of a single hemispherically shaped recess that defines the sample well.

Also, the two-conductor device 200 and the Internet accessible system of FIG. 12 can be used with sensor modules having other types of measurement zones that do not, for example, include a sample well 20 as described above, that use other algorithms for freeze-point detection (e.g., prior art freeze-point detection algorithms or that measure temperature passively). Furthermore, this invention is not limited to the use of thermistors for temperature sensors, and if desired, other temperature sensors such as thermocouples and other temperature sensitive elements can be substituted.

As used herein, the term "time" is intended broadly to encompass absolute or relative measures of time. The term "time derivative" is intended broadly to encompass time differences, slopes, slope of slopes and other measures of the rate of change of a variable such as temperature, whether averaged or not, whether discrete or continuous, and whether numerically or analytically determined.

The term "conductivity" is intended broadly to encompass any measure that varies as a function of the resistance between two probes, whether the measured parameter is current, voltage or some combination thereof, and whether it varies directly or inversely with resistance, and whether measured with DC or AC voltages.

The term "temperature information" is intended broadly to encompass freezing point temperature as determined with an active cooler, ambient temperature, or other temperature parameters. Further, the term "freezing point temperature" refers to a chosen point in the temperature versus time curve, once solidification has begun, or is about to begin. It is not limited to points at the beginning of solidification of the sample, but can be any appropriate point in the curve.

The term "good thermal contact" is intended broadly to signify that the thermal conductivity between two elements is at least 1 W/m·K.

The foregoing detailed description has discussed only a few of the many forms that this invention can take. This detailed description is therefore intended by way of illustration, and not by way of limitation. It is only the following claims, including all equivalents, that are intended to define the scope of this invention.

Appendix 1 - HEX File (Copyright Energy Absorption Systems, Inc. 2001)

```
:020000020000FC
:20000000C3360072C40FE21398015D05000000000000000000000000000000000000B2
:200020000000000000000000000000000000000000000000000000003EA0D3320E003E08D33284
:2000400000003A0500FE163803AF18023E07D3320F003ED6D33213003E92D3321200AFD35B
:20006000321000212FC611270019F93EC0D33214003EC2D33215003EC5D33216003EC5D3B9
:20008000321700AF2115C4773EC02111C4773EC22112C4773EC52113C4773EC52114C47739
:2000A000D33A00003226C43EC0D33215003A12C4210300CDBE113EC23212C4D3321500CC41
:2000C000280A215AC60684AF772310FC210100CD310B3EA02117C4773E082118C4773A0559
:2000E00000FE163803AF18023E072116C4773EC0D33255002122C4773EA032FDCB3E88328B
:200100005DC43E00325CC4215BC43600068221ADC436002310FB3E01D332A0002106C477F4
:200120003E00D332A4002105C4773A0500473A16C4B72802CB203A18C4E6182006CB38CB09
:2001400038CB38783227C40E00115500F74D0CCB390D79D332A9002103C4773E00D332D45D
:20016000000D332E400D332F4003E01D332C40021FCC377212FC611270019F9AFED67219D1D
:2001800000072257C6CDB603CD85053EC332C0CE212F0422C1CEC38E02ED5EAF3234002101A1
:2001A00040360021360022010000D33A00003A02403205003EA0D3320E003EC8D3321300AFD1
:2001C000D3321200D33211003EC5D33214003EC5D33215003EC5D33216003EF0D332170051
:2001E0003EC53211C43EC53212C43EC53213C43EF03214C4212FC611270019F9210800CD50
:20020000BE11CC280A215AC60684AF772310FCED5BD2C62ACEC61922B113210800CD310B22
:200220002AEBC6EB21E213197AFE012818FE022812FE04280CFE102804CB241808CB3CCB85
:200240003CCB3CCB3C24FD2100003AEAC61100E0E5ED4BEBC6FDE5CDEA0900FDE1CD2D0BE4
:20026000ED4BEBC6FD0908CD250500AFBA200708C6021100E00808E12520D5CD2505003EFF
:20028000D6D33213003E92D3321200C33600AFD33230003225C4D33240003224C4D33250DD
:2002A000003223C4D3326700321DC4D33260003221C4D3326500321FC4D3326600321EC42C
:2002C000D33277003219C4D3327000321CC4D3327500321AC4D332B00032FFC3D332B10023
:2002E000D332FEC3AF32FDC33220C4321BC43210C4320FC4320EC4320DC4320CC4320BC45B
:20030000320AC43209C43208C43207C43204C432FEC332FBC332FAC332F9C33E80D3322442
:20032000032FDC3D33A2400E660FE602034CD2505002100002224DC4224FC42250C4215675
:20034000C436FFAF2158C4772377237723772377216FC411610636C923732372ED46CD6106C353
:200360002E03ED5ECDB605ED463E80325DC4CD7403C3E213110000D501000011FF07D33236
:20038000000200032A0200DC20F503C50657210800D3365A10FBC1D3320200D3320200CB54C9
:2003A00028E76079C6086FFCFCFCFC7D3DD1BB28045FD518C3C9CD8707CD9A0400CDD20574
:2003C000C9CD250500CD570428F74FCD250500CD630420F7ED77F5CD2505003AF6CBFE60DC
:2003E000300BAF32F7CBCD710AF1ED67C9FEE038202AF5CB7CCB3FCB3FCB3F21F7CB22
:2004000086E6802007CD900AF1ED67C93AF7CBED67ED76ED562AF5CBEB212FC53AFBCB066E
:200420004F7E1223130D20F9ED7EF1ED67C9F508F5ED77F5C5D5E5DDE5CD9207D33AC346
:20044000000CB572004D332C300DDE1E1D1C1F1ED67F108F1ED5DC9D33AC300CB7FC8D33A2C
:20046000C000C9D33AC300CB5FC079D332C000C90044796E616D6943556E69766572736140
:200480006C20526162626269742042494F532056657273696F6E20372E30352172C40633AF00
:2004A000772310FC2171041172C4010700EDB03E023279C43E00327AC42178041317BC401C9
:2004C0000800EDB021E3122283C42100202287C42100DA2289C4210020228BC42100D92212
:2004E0008DC4CC6F39228FC4216FC42291C43EC93293C43EC33294C421F3222299C42149BD
:200500004C4229BC4214DC436003E20329DC43EE2329EC421CC0532A1C43E8032A4C421790E
:2005200052265C4C9F53E5AD3320800F1C93A4DC4B720FAED76ED5611B1C40100003AF8D3
:20054000C33295C47EB72806122313181F6ED43ADC43E01324DC42A49C4ED7EC92A93C482
:20056000222AC4216FC43A2BC477215EC43600115FC4DFDFED5EC37305DFED5E3E53D332C6
:200580000800C382053ECEED4F3ECFED473EC33230CE3240CE3250CE212F062231CE2148DF
:2005A00062241CE216FC42251CE2161062270C43EC3326FC4C93ECEED4F3ECFED473EC9D2
:2005C0003230CE3240CE3250CEC9E1E9C37305C379052146C40615AF772310FC212CC4227E
:2005E0004BC421ADC42249C421A5C42252C4CC6C22F6C322F4C332F3C332F2C3C9E5F5ED1E
:2006000076ED76E12246C42158C47EB72804ED5E3600F1E1C9ED76F5ED563A4FC4B728046F
:20062000F1ED7EC93E01324FC4F13E01ED7EC9CD4A07F5CD1506B7280DE5C4042BD404E135
:20064000CDFD05C37506F1C9CD4A07F5CD1506B728F4E5C4042BD404E1CDFD05ED56C3752A
```

A1

```
:2006600006CD4A07E5216FC436C9E1F5CD1506B728D4CDFD05F1D908ED54D5C5F5FDE5DD7D
:20068000E5ED774FC5E521100039E5D908E5D5C5F521000039112CC4011A00EDB0211A0026
:2006A00039F93E01324EC4AF3248C43A4DC4FE012000CD400700CD2505ED76ED76E17DE619
:2006C000032803CD92073A50C4B728272151C4ED76ED567EB7F5200134F1ED7E20152A3AE2
:2006E000C4E5DDE12A54C411EC06D5E9AF3250C43251C43A4EC4B7C2AB062A34C411E6FFC6
:2007000019F9EB212CC4011A00EDB0F1C1D1E1D908ED56AF324FC43A48C4B72805216FC419
:200720036C3E1E1C179ED67DDE1FDE1F1C1D1ED54E52A46C465ED5433D908CD6D07ED4DC2
:200740003A59C4B72803C33600C9F5E52AF3C37DB528087D32F2C3AF32F3C32AF6C37CB573
:20076000280822F4C3CC6C22F6C3E1F1C9F5E52AF4C322F6C3CC6C22F4C33AF2C332F3C344
:20078000AF32F2C3E1F1C9219D072257C6AF32FECBC93A59C4B7C236002A57C6E9AF32FC9E
:2007A000CBCD5704C832F8CBFEA2200721E2072257C6C9FEA12007218A082257C6C9FEA091
:2007C000200921A0092257C6C3A009FEA520092167092257C6C36709C92257C621F8CB863A
:2007E00077C9CD5704C832F4CB21EF07C3D907CD5704C832F5CB21FC07C3D907CD5704C885
:2008000032F6CB210908C3D907CD5704C832F7CB211608C3D907CD5704C821F8CBBE3E007A
:20082000772809217D082257C6C37D082135082257C6C335080E06CD6304C0214208225756
:20084000C6C93AF6CBFEE038053AF7CBED672AF5CB4ECD6304C02322F5CB21F8CB79867718
:2008600021F4CB352801C9216E082257C6C93AF8CB4FCD6304C0219D072257C6C90E15CDD5
:200880006304C0219D072257C6C9CD5704C832F4CB32FBCBB720053C32FCCB3D21A208C3AF
:2008A000D907CD5704C832F5CB21AF08C3D907CD5704C832F6CB21BC08C3D907CD5704C8A0
:2008C00032F7CB21C908C3D907CD5704C821F8CBBE280921FC082257C6C3FC0821E5082271
:2008E00057C6C3E5080E06CD6304C02109092257C6212FC522F9CBAF32F8CBC90E15CD63F6
:20090000004C0219D072257C6C9CD5704C82AF9CB772322F9CB21F8CB86773AF4CB3D32F4AB
:20092000CB2801C9212B092257C6C9CD5704C821F8CBBE2809215A092257C6C35A0921448C
:20094000092257C6CDD403214D092257C60E06CD6304C0219D072257C6C90E15CD6304C009
:20096000219D072257C6C9216D092257C63A5CC64F32F8CBCD6304C0217E092257C63A5DC2
:20098000C64F21F8CB8677CD6304C02191092257C63AF8CB4FCD6304C0219D072257C6C966
:2009A00021A9092257C6C3A9090E003A4DC4B72802CBC13A4EC4B72802CBC93A50C4B728FC
:2009C00002CBD13A56C4B72802CBD97932F8CBCD6304C021DA092257C6C93AF8CB2F4FCDEA
:2009E0006304C0219D072257C6C9F5DDE5E5CB38CB19DD2100F03E09FDE400DD64DD23DD4C
:200A000023FD23FD230B78B720ECB920E9E1DDE1F1C9EB57CB3FCB3FCB3F5F7A1600B9
:200A2000E60FCB27CB27CB27CB278430011C67C5F5ED4BEBC64806006C7BE60F67160079FE
:200A4000FE012822FE02281AFE042812FE102806CB25CB141810CB3CCB1DCB3CCB1DCB3CB7
:200A6000CB1DCB3CCB1DED5BEDC61BDCF1C1C918FE2AF5CBE511FF0FDC1100E0ECEBE17C2D
:200A8000CB3FCB3FCB3FE6FFDE0EEBF518073AF7CBF52AF5CBED67ED5BEBC61B7A2F72
:200AA000577B2F5FDCE5E5FD2100F0DD7DED4BEBC63E09E400FD64DD23DD23FD23FD230B08
:200AC000BAFB820ECB920E9ED5BEBC6E119ED5BF5CBAFED523AFCCBFE01200501000118AE
:200AE000113AFBCB4F0600AFE5ED42E1D2F20A06004DFD2AF5CBED5BEBC61BFDDC1100F0F6
:200B0000FD19DD212FC53E09FD6C54E40062FD64DD23FD230BAFB820EDB920EAD1F1CD2D04
:200B2000BC9C304C818FE2AF0C6E918FE2AF2C6E9DDE54DCC6C22E6C622E4C622E0C622C7
:200B4000DEC6AF32EBC6CB41280C3A11C4F6083211C4D3321400CB49280C3A12C4F608326A
:200B600012C4D3321500CB51280C3A13C4F6083213C4D3321600CB59280C3A14C4F6083268
:200B800014C4D3321700CB4128103EF232EAC6CB4928403E4032EBC61839CB4928103E3221
:200BA00032EAC6CB51282C3E4032EBC61825CB5128103E7232EAC6CB5928183E4032EBC69A
:200BC0001811CB5928073EB232EAC6180621FFFFDDE1C901D0000217D0E1124CBEDB001D018
:200BE0000213F0F1154CAEDB021270B22F0C601C00021451111C4C8EDB001C00021430EEA
:200C00001104C8EDB001100021220B11F4C6EDB001800021F70D1184C7EDB0018000211E34
:200C2000E1104C7EDB0CDC00DCC281E2A5AC6CC2006DDE121FEFFC92A6BC622EFC62A6FD5
:200C4000C622EBC62A71C622EDC63AEFC6FE01280BFE02280CE1DDE121FDFFC921BE0F18E5
:200C600003217E1001D0001184C9EDB02184C922F2C62ACEC6E5CC2006E1110800180BE11B
:200C80007C2F677D2F6F2311030022E6C6ED53E8C6CD2F0A22E4C6ED5BD2C62ACEC619E5C6
:200CA000CC2006E1110800180BE17C2F677D2F6F2311030022E0C6ED53E2C6CD2F0A22DE2A
:200CC000C6CC6CDDE1C9005DBF8000000202003DBF80000002020007BF800000040200081B
:200CE000BF80000004020010BF80000008020012BF800000080200B5BF001020000100B6A0
:200D0000BF001040000100B7BF00108000010014000020001010014000020001010000290
:200D200040000200020100A24000020002010003400004000201000A34000040000201063F0
:200D40000000400020100734000040000201006040000200010100824000020002010D552
:200D60001F80000040200351F8000000402000DA1F00010004020000BA1F00010004020000A470
```

A2

```
:200D80001F000100080200C41F000100080200251F800000020200261F8000000202004565
:200DA000DA80000008020046DA000100080200C1DA80000004020000000000000000000083
:200DC000CDC4C8EBDD21C70C010800E400CC280DE400ED52280BDD7C09DD7D18EE21FFFFD9
:200DE000C9E40222EBC6E40422EDC6E4067D32EFC6210000C918FEF5E5C60E171717E6038A
:200E0000F52111C4856F3E008C677ECB9F7767F12E14856F7C2600D377E1F1C918FEF5E55E
:200E2000C60E171717E603F52111C4856F3E008C677ECBDF7767F12E14856F7C2600D37787
:200E4000E1F1C9DDE5F5D5DD2150C3210000EBDD2BDDEC28163E5AD3320800CB762806CB60
:200E60007628EC180ECB7620E61808D1F1DDE121FDFFC9D1F1DDE1210000C918FEF52AF066
:200E8000C3CC201D2A5AC6CC2817F5D5CD120AED5BDEC6AFED523807D1F1F121FCFFC9D1FC
:200EA000F108ED77F5C5D53AEFC6FE01282ADDE5DD2100F0ED4BEBC63E0921FFFFDD64DDE9
:200EC00023DD230BAFB820F0B920EDDDE108CD2D0BD1C1F1ED67F1C9ED76ED5E3AEAC6CDE6
:200EE00084C7C605ED673EAA3255E53AEAC6C602ED673E5532AAEA3AEAC6C605ED673E800E
:200F00003255E53AEAC6C605ED673EAA3255E53AEAC6C602ED673E5532AAEA3AEAC6CD04EE
:200F2000C708CD84C7ED6708626B363008CD04C708CDF4C6ED7ED1C1F1ED67F1C918FEF505
:200F4000ED77F5C5D52AEDC62B2B444D3AEAC61100E00808CD24CB082AEBC619EB7AFEE0F4
:200F60003007083C3C1100E0080B78B720E5B920E2D1C1F1ED67F1C9F508F508E5D5DDE5C0
:200F8000E3E5E3DD2100F0E32E00E378B1281C1A083E09DD6C08BD2808E32E01E3ADA52049
:200FA000060B13DD2318E4E32E02E3010000E34DE3E1E3DDE1D1E108F108F1C918FEF52AE3
:200FC000F0C3CC201D2A5AC6CC2817F5D5CD120AED5BDEC6AFED523807D1F1F121FCFFC99C
:200FE000D1F108CC6CE36069ED77F5DDE5ED76ED5EED4BEBC608ED6708CD780F79B7200A7F
:20100000ED4BEBC609EB09EB1865FE01280908ED67E5CD24CBE108ED4BEBC6DD2100F03A5B
:20102000EAC6CD84C7C605ED673EAA3255E53AEAC6C602ED673E5532AAEA3AEAC6C605ED74
:20104000673EA03255E53AEAC6CD04C708CD84C7ED67083E09DD6CEB73EBDD23E3CDF4C69E
:20106000E3130B78B720B8B920B508CD04C708ED7EDDE108F1ED67F1444DE3C918FEF52A59
:20108000F0C3CC201D2A5AC6CC2817F5D5CD120AED5BDEC6AFED523807D1F1F121FCFFC9DB
:2010A000D1F108ED77F5DDE5FDE5CC6CE36069ED76ED5EED4BEBC608ED6708CD780F79B706
:2010C000200AED4BEBC609EB09EB186AED4BEBC63AEAC6CD84C7C605ED673EAA3255E53AFB
:2010E000EAC6C602ED673E5532AAEA3AEAC6C605ED673EA03255E53AEAC6CD04C708CD849D
:20110000C7ED6708DD2100F0EBFD7DED4BEBC63E09DD6CFDF400DD23DD23FD23FD230B0B99
:20112000AFB820EBB920E8FD7CEB1BE3CDF4C6E31308CD04C708ED7EFDE1DDE1F1ED6708A1
:20114000F144DE3C9ED77F5ED76ED5E3AEAC6CD84C7C605ED673EAA3255E53AEAC6C60233
:20116000ED673E5532AAEA3AEAC6C605ED673E903255E53AEAC6ED671100E0CDF4C63A008F
:20118000E0673A01E06F3AEAC6C605ED673EAA3255E53AEAC6C602ED673E5532AAEA3AEA9E
:2011A000C6C605ED673EF03255E5E51100E0CDF4C6E13AEAC6CD04C7ED7EF1ED67C9ED7713
:2011C000F5E521CEC6EBE1CB5D28043EF01822CB5528043EB0181ACB4D28043E7018123E32
:2011E00030CB45200C210000225AC621FFFFC3AA12ED6721F0FF011000EDB021D8C60603A8
:20120000F57EFE55200B237EFEAA20052310F2180DF1210000225AC621FEFFC3AA1221CE45
:20122000C6DDE4007C472F677D4F2F6F234D017300F1ED67115AC6EDB021D6C6DDE400EB04
:2012400076EB21D6C6AF7723772̸17300EB210000E3D5E3E5E321FF00ED5238052173001865
:20126000321FF00E5215AC6E5CDB1122706444DE309E3D121FF00EBAFED52EB30D3E3E5A3
:20128000211000E521CEC6E5CDB112270676EBAFD5ED52D1200B21D6C6732372CC6CC3AA57
:2012A00012210000225AC621FDFF22F0C3F1ED67C9210200395E2356D5234E23237E2366F3
:2012C0006FD11A13D55706087CAA07300B293E10AC673E21AD6F180129AFCB1210EA0D2005
:2012E000E0D1C9E100800000494F505F52414D5F53544152D4920000494F505F444154418C
:2013000053454756A1CC200000494F505F52414D5F53495AC500CE00494F505F494E5456D4
:2013200045435F424153C5400000494F505F464C4153485F53495AC5006000494F505F4431
:20134000414F52C700D000494F505F5354441434B4F52C75DC4004F504D4F4C5CC0524
:201360002E2E65786974B2790500657869F4CF05002E657869F47905002E65786974B299
:2013800069C40052535432385357D46BC40052535432385357545F4F46C6CA05002E737411
:2013A00061727475F05D05002E2E62705F696E69F48400005F49445F424C4F434B5F534929
:2013C0005A45DF000000DDE5DD210000DD39E40AE5D1210C0039D5010A00EDB0E1DDF9DD9E
:2013E000E1C9C3FA13ED77F5F1ED67C9ED77F5F1ED67C9ED77F5F1ED67C9CDCA0521B3C30B
:201400002263C4211D3D2261C42100022267C4216FC42269C4216BC436C9210507E5CDDFA3
:201420002D210000E5CD790500000000712F000000E0F80072E6FF00FFCB920058679200B2
:20144000000E0FE0000E0FE00E3C2B3C300D0FFDFB3C3B2C300C2FFC100CCFECD3B36000092
:20146000E22F7201CF3A720100000000000000000000000000000000000007EC4B62B49
:201480002129200C104600210C114600380039000800090FFFFFFFFFF004F4646004F4E07
```

:2014A00000004F4646004F4E000046500000544F00004345000044570000435550000521E
:2014C0004F4144000500C709F0F8C7B9E0F9C7C7E5F90A456E65726779202D204672656553
:2014E0007A6520506F696E7420446574656374696F6E20416C676F726974686D2056657210
:201500000203039500000A2D2D2D2D2D2D2D2D2D2D2D2D2D2D2D2D0A0053656E736F72204F4FC
:20152000647265737373206973202564 0A000A44533313842323020492E442E203D2000303047
:201540000025780030302000257820000A0A206654656D70203D2025382E3366000A284D61
:20156000296F6E69744F7220546D7065726174757265732020284629696E64204672652B
:20158000657A6520506F696E742C206F722046696E6420284429657733A20000A0A434F3F
:2015A0004F4C45552050415241445545445552530A2D2D2D2D2D2D0A007A506172616D5265A1
:2015C000632E4D696E696D756D5F436F6F6C696E675F54656D706572617475726520202027
:2015E0002025352E31660A007A506172616D5265632E4D61786 D756D5F436F6F6C696E4E
:20160000675F54696D65202020202020202020202020202025640A007A506172616D526563BD
:201620002E4465775F466F726D6174696F6E5F4F66667365742020202020202020202028
:201640002025352E31660A007A506172616D5265632E53656E736F725F526561 64696E6773A8
:201660005F7065725F4D696E75746520202536 40A00694869676854656D702020202020CB
:2016800020202020202020202020202020202020202020202020202020 2025352E3166CB
:2016A0000A000A202054696D6520202020205431202020202020204332 20202020202020ED
:2016C00054332020202020202054462020202020625F666974202020735F74656E20208C
:2016E000625F736C6F7065202020433F200A0025362E32662025382E32662025372E316655
:20170000002025382E32662025382E32660A0025362E32662025382E32662025372E31662074
:201720002025382E32662025382E32660202020202020202020202020202020202020A3
:2017400002020202020202025730A0025362E32662025382E32662025372E31662025DD
:20176000382E32662025382E32662025382E33662025382E33662025382E336620202 5D7
:20178000730A0025362E32662025382E32662025372E31662025382E32662025382E3266A1
:2017A000202020202020202020202020202020202020202020202020202020 2573D1
:2017C0000A00F5E5CDE11F0021CB1FE5D9210000CDD529EF21D300E5CDF11827027D329C91
:2017E0006AEF2A9C6A2600EB210800DCCC2BCCCA8618EF21FF00E5210000E521D300E5CD7F
:20180000CC212706EF2A28C0CCCA10183A21C0B7CA8018EF2A26C0232226C02BEB219CFFBF
:2018200019EB3003CDC82C00EB218EC0196E2600E5CF29E7FA2702E5210000E521D000E501
:20184000CDCC212706EF218D00E5210000E521D400E5CDCC212706EF2A28C02B2228C0CC56
:201860002BCCCA7D18EF21FF00E5210000E521D300E5CDCC212706EF3E003221C0C38618B7
:20188000EF3E003221C0EF2A9C6A2600EB218000DCCCCAE818EF2A22C0232222C02BEB216C
:2018A0009CFF19EB3003CDC82C00EB212AC019E521D000E5CDF11827022600E5CF29E7FAE8
:2018C00027027DE177EF2A24C02B2224C023EF2A24C0CCCAE818EF214D00E5210000E521BD
:2018E000D400E5CDCC212706EFD9210000CDDF29C9C402D36E2600C9C721E0FAD1ED77676D
:20190000E533D5C7EEE4FABF1BC13AE4B87839C6A3E6337B14124100002040CB7A28237D54
:20192000EB1F300437FCB7C81F300637FC37FCB7C81F3008FCFCFCFC1100F0EC1FD06C26C8
:20194000FFC97DEB1F3004B7FCB7C81F3006B7FCB7FCB7C81F3008FCFCFCFC11FF0FDC1F37
:20196000D06C2600C9B76CE50D6D6173126312C71E901D555C7808B7CB10CB792802CBC011
:20198000CBF93E7F90FE083854CAEE19FE1838080100001100 00186CD608FE0830240600A9
:2019A0006069CB572808FCFBFCFBFCFBFCBCB4F2804FCFBFCFBCB472802FCFB06004DC3B3
:2019C000EE19FE10300BD6085A51010000282118CFD6105901000016002815 18C3ED44C698
:2019E000080600B7F3CB11CB103D20F81802060008CB7F280FB7210000ED52545D21000091
:201A0000ED424D44C9EBC40001FDFF09E5ED77F5CC6CE5EBE56701241AC5D9C40ED9FD2A47
:201A200065C4FDE9E1C1C1C1C978EE8047C921C70100CB300A00004A4F000085C6017BF670
:201A4000AF0795422E1601000020CD4F1AEBC9CDAA1A3CEA831AFA8C1AFE1F3026D617FA5C
:201A6000741A281647AFCB23CB12CB151710F7474DAF1809ED444FCDAE1A06004DCB7CC800
:201A8000C3061B7CE680470E005159C911000006000E00C97CEE40CB15174F37CB1DD97C66
:201AA000EE40CB15174F37CB1DC9696018F1AF47CB612807B2B35D68501808CB592809B305
:201AC0005A5568B72802F680CB51281CCB3DCB1ACB1B1FCB3DCB1ACB1B1FCB3DCB1ACB1B81
:201AE0001FCB3DCB1ACB1B1FCB49280ECB3DCB1ACB1B1FCB3DCB1ACB1B1FCB412807CB3D64
:201B0000CB1ACB1B1FC9B7210000ED52EB210000ED424D44C9C404EB21261B197EC402D321
:201B2000A6CCFC6FCCC90102040810204080CD1D1CC9C9ED5F672EE0EB212E1BED56011032
:201B400000EDB03A23C4CBD73223C4D33250003A22C4CBD73222C4D33255003E0132FAC355
:201B6000D332E400ED5DC9F5C5D5E5ED56D33AE300CB57201F3AC7C3B72807CDC11B00CC42
:201B80002009CDB41BCDC51B001809CD9B1B3E17D332E000ED5DE1D1C1F1C93A23C4CBD7BB
:201BA0003223C4D33250003A22C4CB973222C4D3325500C93A22C4CBD73222C4D3325500C6

```
:201BC000C92AC1C3E93A7969B72051217E69E5CDCA1D2702CB7C20443AC3C3B7202F3AC626
:201BE000C3B728333AC4C3B7201AE53AC5C367CD1E1DCCE128073E01327969181A7DD33265
:201C0000E10018183AC5C367CD3F1D180A3AC4C3B728E37DF6806F7DD332E000C9F5C5D5A0
:201C2000E5D33AE3004F17DA781CCB5120293A7969B720143AC7C3B72806CDC11BCC200C45
:201C4000CDB41BCDC51B1825AF327969CD9B1B3E2AD332E00018163A22C4CB57280F3AC7C3
:201C6000C3B72806CDC11BCC2003CDC51BD332E300ED5DE1D1C1F1C9D33AE000CC6F473A6F
:201C8000C4C3B728047DE67F6FC5E521066AE5CD9E1D2704C1CB6928053E013278693AC642
:201CA000C3B728373AC4C3B7202168 3AC5C367CD1E1DCC280BCB7128223E01327769181BF0
:201CC000CB7120173E013277691810683AC5C367CD6F1DCC20053E013277693AC7C3B72849
:201CE0002021066AE5CD081D2702545D424B2A7A697ABC380C7BBD380821011DE52ABFC326
:201D0000E9ED5DE1D1C1F1C9C40223234E2346235E2356DDE401EBB7ED421923DCC9D5DD80
:201D2000E5AF575D6FDD216668DD19DD7E00CC2808EE806FCCDDE1D1C96FCCDDE1D1C9D56A
:201D4000DDE57DE67F6F5FAF57DD216668DD197CB7280ADD7E00B7280EDDE1D1C9DD7E00E9
:201D6000B72004DDE1D1C97DF6806FDDE1D1C9D5DDE57DE67F5FAF57DD216668DD197CB7A3
:201D80002 80DDD7E00ADE680CC6FCCDDE1D1C9DD7E00ADEE80E680CC6FCCDDE1D1C9DDE544
:201DA000DDC404E4044D44E406EBE4022BDCED422815CC09DCEBC4067DDD7C090108000980
:201DC00077EBF404210100DDE1C9DDE5DDC404E4024D44E406EBE404B7ED4220032B181108
:201DE000CC09DCEBDD7C09010800097EEBF402CC6FDDE1C9FDE1E17AA4577BA55FE178A402
:201E00004779A54FFDE9210400CD7A1E210100E5CD3E1EE1F5CD2D1EC21F1EF1C3271EF197
:201E2000210200D2271E2DD1C1C1D52DC978B1B2B3C9210400CD7A1E210200C30F1E210602
:201E400000397E935F237E9A57237E994F237E68679847F57CADF25C1EF13FC9F1C9C9E188
:201E60003333ED54C9E5C501000421060039AF799E772305C26F1EC1E1C9397E735F237E9A
:201E80007257237E714F237E7047C9DDE5DDC404CC6CF400F402F404C406F406DDE1C93EED
:201EA0005AD3320800C9AFD9E1D9E1ED52E1200DED422009210100D9E5D9AD6FC92100006B
:201EC000D9E5D9AD6FC93E01B718DCFDE1E1AFEBED52D16960ED52210000CB15FDE9FDE166
:201EE000E1AFEBED527D694F7C6047D1ED523807200579B020013F210000CB15FDE9FDE10E
:201F0000E1AFED52E1ED42210000CB15FDE9FDE1E1AFED52EBE1ED42380720057BB22001A1
:201F20003F210000CB15FDE9C402EBC404D9C406CCEBF3F3F3C408EC1E0FDCEB010800F723
:201F40000214B1F09FD7DD9ED56FDE9CB86D3EDA8ED5DC9CB8ED3EDA8ED5DC9CB96D3EDA808
:201F6000ED5DC9CB9ED3EDA8ED5DC9CBA6D3EDA8ED5DC9CBAED3EDA8ED5DC9CBB6D3EDA8A1
:201F8000ED5DC9CBBED3EDA8ED5DC9CBC6D3EDA8ED5DC9CBCED3EDA8ED5DC9CBD6D3EDA801
:201FA000ED5DC9CBDED3EDA8ED5DC9CBE6D3EDA8ED5DC9CBEED3EDA8ED5DC9CBF6D3EDA861
:201FC000ED5DC9CBFED3EDA8ED5DC9FDE1DDE1E1D1C1D9D1C1F108F1ED67ED7EE1F1ED5D6B
:201FE000C9E1ED76ED77F508F5C5D5D9C5D5E5DDE5FDE5D9E9DDE5DD210000DD39E5E40681
:20200000D1D5AFBEEDA020FBE1DDF9DDE1C9ED76ED5EAF6F67324A68223B68223D683249A9
:2020200068223F68224168224768CF7BE7FB214368CD822D003238683E80324F68ED5F6733
:202040002E00FD7DFD3600C3FD23216820FDF4003A18C4E6FCF6013218C4D3320000AF3245
:202060004D68324E68ED7EC9F5ED76E5D5DDE5D33A0000214E6834ED5DCD4B21214F683513
:202080002008CD0D213E80324F68CDD620ED56214E6835201C3A4D68B72816C508F5D9E5C4
:2020A000D5C5FDE5CFBB2000FDE1C1D1E1D9F108C1DDE1D1E1ED7EF1ED5DC92AF6C3DD7DFA
:2020C000CC6C39F402E404F9CC6C22F6C3AF324D68324E68ED453A4A68CB7FC82AF6C37C98
:2020E000B5C85E23561B722B737AB3C03C324D68C9112368CB251923FD210400FD39FD7EED
:202100000077C9112368CB2519562372C93A5DC4E6082808214EC47EB72801C93A3768B7C3
:2021200028135721236 83E00BE28052335280A2B23231520F3CD9F1EC921F400E5CD051ADC
:20214000270221F400E5CD79052702214A687EC68077D0110100DD213B68E40019F4001B4B
:202160003005E40223F4023A4968C6FA324968E404ED5AF404133005E40619F406E400DD70
:202180007E0CACE604C8DDAE0CDD770CE40819F408D0E40A19F40AC9ED5ECFBB2100546F08
:2021A0006F206D616E7920726563757273696F6E206E74657272570747318FEAFD55D6C
:2021C00054BE28032318FAB7ED52D1C9FDC404FD7CCC200AC406FDC402D3FD7500C9C40664
:2021E000ED56FD7500C402EBFD7C3D3EDA8ED5DC978B1B2B3CA4222FDE1C5D9D1210000D982
:20220000E1C1E521000078CD25220879CD2522C1D94F0847C5D978CD25220879CD2522C13D
:202220005F0857FDE9060817ED6AD9ED6AD9B7ED52D9ED523006D919D9ED5A37D910E81700
:202240002FC921ED00E5CD051A2702CD7905D1ED7767E533D5C716E8FB0000003FCDCC4CC6
:202260003D0AD7A33B6F12033A17B75138ACC5A736BD37063595BF563377CCAB31210400AF
:2022800000395E23567AB328371B722B73210800395E2356D5210E00395E2356D5210E0039ED
:2022A0005E2356D5210800395E2356D511B922D5211000397E23666FE9C1C1C1C118BE21DF
:2022C0000000200396E26002600C90604B7CB13CB1210F9C9EB210400397E23666F7AFE103873
```

```
:2022E000040E04181DCDC9227AFE1038040E031811CDC9227AFE1038040E021805CDC9227C
:202300000E0106043E00CB13CB121710F9FE0A3804C6371802C63077230D20E63600C9216D
:202320000600397E23666FD5E5507A59B3280BCDDC22C1D10E04CD0223C9C1D1CDDC22C9D5
:20234000CD3325D5C5E5FDE12600FD6E00CD99242804FD2318F2C178B7C2FE2379FE25D249
:20236000FE23162BFD7E00FE2B2806FE2D2004162DFD2379B7C29A23FD7E00FE3028050EE4
:202380000AC39A23FD23FD7E00FE582804FE782007FD230E10C39A230E08D5C5110008D9A1
:2023A000110000D9D5D9D5D92600FD6E00E5CD8524E128067DD630C3D223E5CD8024E12842
:2023C000067DD637C3D223E5CD7B24E1CA33247DD657D9D1D9D1C1B9D22D24C50879CD595B
:2023E00024DA1024D9CB7CD9C210240816005F19D9110000ED5AEBD9EBFD23C3A423E17C3F
:20240000B52806FDE5D17323720100001100C9FD23D1E12E2BE5D57CFE2D20080100800E
:202420000110000181001FF7F11FFFF1808D9D5D9C11803C1D1E1E17CFE2D200F210000AF58
:20244000ED525D54210000ED424D44D9E17CB52806FDE5D1732372D9C9210000D9210001A
:20246000D9B7C8CB3F300619D9ED5AD9D8CB23CB12D9CB13CB12D9D8C361241E01C39E24DE
:202480001E02C39E241E04C39E241E08C39E241E10C39E241E40C39E241E80C39E24CB7D44
:2024A00028022E80260001B224097EA3210000C823C9202020202020202020A0A0A0A0A008
:2024C0002020202020202020202020202020202020C0505050505050505050505050EC
:2024E00050504C4C4C4C4C4C4C4C4C505050505050504A4A4A4A4A4A4242424242428A
:2025000042424242424242424242424242505050505050494949494949414141414104
:2025200041414141414141414141414141505050502000D9E1D1D9E1D1C1C5D5E5D9D5E505
:20254000D9C9C1E1D9E11181250E00D9E5E5C50605D91A13D95FD91A13D957B70EFF0CED14
:2025600052D25E251979D9B14FD9280779C630D97723D910DCD979B120043E307723AF7745
:20258000C91027E80364000A0001000605FD218125FD5E00FD23FD5600FD23E5B7ED52E168
:2025A000300310ED04682600C9CB7C28DEEB210000B7ED52CD8B2523C9C1D1E17AB7F2D171
:2025C00025CBBFB3CAD1257B2F5F7A2F5713362D23E5D5C5C3422500CA9A3B00E1F5058094
:2025E00096980040420F00A086010010270000E803000064000000A000000010000000262
:202600000000007B2F5F7A2F57792F4F782F47C9AF41E5772B10FCE1EBAFCB2617CB2617F5
:20262000CB26170605CB2617D60A3002C60A3FEBCB16EB10F01B2B0D060820E9C9E5CD8042
:2026400024E1C811200019C980F0FA02404B4C0020A1070050C3000088130000F4010000EC
:202660003200000005000000C71DE0FDC7C4EFFCC740E0FDC719E1FDC7EFEBFC4500789A56
:202680005440FDE178B1B2C2A5267BFE20D2A526D1E1B7CAAF2647CB3CCB1DCB1ACB1B1011
:2026A000F6444DFDE9E1E1010000110000FDE9444DFDE9CDCA26FDE1E1D9E1FDE5E5D9E5C1
:2026C000CDF0215D54D9E5D9C1C978B1B2B3C0E121EE00E5CD051A2702CD7905FDE178B1C0
:2026E000B2C2A5267BFE20D2A52647D1E1B7CAAF26AFCB13CB12CB15CB1410F5C3AF26EB65
:20270000E17BBE2320137ABE23200F5E2356EB7AFEE03804131AED67E9230B78B12323233F
:2027200020DFE5C9CBB8C97F7D7B7A7876757372706F6E6D6B6A69686766656463626160EB
:202740005F5F5E5D5C5C5B5A585756555453515D4F4F4E4D4C4B4A4A49484747464545445A
:2027600044434242414140AF474F575FDDE1C9DDE17CB72006010080CC6CC9E52100003932
:202780002323DDE400E521EA00E5CD051A2704E1C9DDE560692938D737CB1D7CB728C8E5B2
:2027A000D5656A531E00791FEE401FFE203003B7FCFBD9CC6F112727197E47570E0059F71A
:2027C0002976EBEB444DED49CB78F728011929EB2100C0ED52444D571E00CB78F728011988B
:2027E00029EB424BF7CB182976EBD9ED49D9EBCB78F7280119CB10ED6AEB2100C0ED524404
:202800004D76EBF719CB18ED6A424BF7CB11CB10ED6AD5E3D9ED59CB78F7280119AFFD210E
:20282000000000FD09D9EBED41EBDD210000CB7A2802DD09CB78F7280119EBDD19EBDD7CEBD6
:20284000FD19CE00D9E3CB78F7280119EBFD7C19CE00D9835F300114D929D9F3D9EBCC6C47
:20286000ED52D92100C0ED52444DD1ED51CB78F7280119D9444DCB78F7280119E3D9EB096E
:20288000030011329F3D9D1C17678414A7BED49D9E3CB78F7280119D9FD210000CB7A2802A5
:2028A000FD09CB78F7280119EBFD7C1976EBD9ED49470E00CB78F728011976EB19EBD9306A
:2028C0000113E30930011329F308D67FCB2F300229F3013F00093001134A535CC67FB71F52
:2028E000473802CBB9DDE1C921E400E5CD051A2702CD7905D1ED7767E533D5C7B0EEFDC453
:2029000002CB4ECBCE210000200123C9DDE5FDE5DDC406FDC408DD4E02DD4603C40ACC28AC
:2029200028E406EBE404ED42281FDD7C093E08856F3001247E036069DC444DFD7700FD2300
:20294000C40A2BD40A7DB420DBC408EBFD7CB7ED52DD7102DD7003FDE1DDE1C9C402CB8E2A
:20296000C93200C71AE0FEF5E52AB1C12322B1C13E00D332B300D332B200D33AB000E1F134
:20298000ED5DC97CB7F0EB210000ED52C9D1ED7767E533D5C71CE7FEC40223235E23562396
:2029A0004E2346DDE401EBB7ED4219DCC9D1ED7767E533D5C727E7FEC402CB86C9C402CB42
:2029C00046CBC6210000200123C9D1ED7767E533D5C764E7FEFDE139F9FDE5D9C3E929FDBC
:2029E000E139F9FDE5D9C3022AE5F53A5EC4B7280E2A5FC423225FC42A91C43A93C477F1CA
```

```
:202A0000E1C9D9E5F53A5EC4B728162A5FC47DB428082B225FC47DB420072A91C43A94C481
:202A200077F1E1D9C97DEB1F300329B7C81F30042929B7C81F3004292929291FD0652E00AC
:202A4000C9FDE178CB1117B7C28B2AC3912AFDE1E1B7ED52EBE17CED424F2014087AB3CA0A
:202A60008B2A180DFDE1E1B7ED52EBE17CED424F0878B1FA842A08DA912A7CB5B2B3CA919A
:202A80002AC38B2A08DA8B2AC3912A210100B5FDE9210000A5FDE9FDE1E1B7ED52EBE17C19
:202AA000ED424F2014087AB3CA8B2A180DFDE1E1B7ED52EBE17CED424F0878B1FAC62A08ED
:202AC000DA8B2AC3912A7CB5B2B328C508DA912AC38B2A7CB5CA362BAFF5C3F02A7CB5CA79
:202AE000362B7AACF5ACEBF2ED2ACD2C2BEB7CB7FAF62ACD2C2B4D44210000783CC2072BE0
:202B00007A813E10DA0C2B6A535C3E0829EB29EBD2142B23E509E1D21C2B09133DC20C2B66
:202B2000EBF1F0EBCD2C2BEBC32C2BC976EBEBCC6CED5276EBC921F000E5CD051A2702CD27
:202B40007905ED76DDE5ED77CF542B00DDE1ED7EE12706E9ED67FDC40CC408FDF400FD46DF
:202B60006CB48281EFD360600CC6C39FDF404FD7CEBC40A19FDC406F9EB22F6C3FD7C23EA
:202B80002323E9CC6C39FDF404FDE402F9FD22F6C3ED45FD2AF6C3CC6C22F6C3FD3606028C
:202BA000FDE404F9ED452AF6C3CCC8ED76DDE5CFB82B00DDE1ED7EC9AF2AF6C3EBCC6C22EE
:202BC000F6C339EB2323732372237E23666FF9ED5DED45FD7DCC6C22F6C3EBFD360003FD11
:202BE000E4FEF9ED45FDE1E5235E2356E1D5C3AB2BCD562C7EE6FB77E6032006235E23568E
:202C0000181EE6012802AFC9CB8E23D17323723EDFBA300423ED7777AAAB2377EBF601E9DD
:202C20002346237EAAABA8200DE1EB7CFEE0380378ED67F601E921F300E5CD051A2702CD78
:202C400079057EE604C07EE6FCB0772306007023703702370C9E15E23562346237AB32893
:202C60001078EB7723060070237023702370EB18E6E9110000193E0677C34B2C11000019FD
:202C80003E0777C34B2C7EF60577C97EE6FE77C97EE6012805AF210000C9210100B5C97E9A
:202CA000E603FE032805AF210000C9210100B5C95E2356234E234623C9ED54CDB02CED54FC
:202CC00073237223712370C921E500E5CD051A2702CD790578B1B2B3CA4222780878B7F254
:202CE000EF2C210000ED52EB210000ED424D44FDE1C5D9D1210000D9E1C108A8F5E578B7EB
:202D0000F2172DE1D5EB210000B7ED52EB210000ED42444DEBD1E521000078CD252208792A
:202D2000CD2522C1D94F0847C5D978CD25220879CD2522C15F0857F1F24B2DE5210000B7F1
:202D4000ED52EB210000ED424D44E1FDE9FDE1E1B7ED52EBE1ED424D44FDE9D9E1D1C1D955
:202D6000C5D5D9E9CDCA26FDE1E1D9E1FDE5E5D9E5CDD42C5D54D9E5D9C1C9ED54CDB02CB3
:202D8000ED54ED76ED5673237223712370ED7EC9FDE1E119EBE1ED4A4D44FDE9ED76ED56F1
:202DA0005E2356234E234623ED7EC9D9C402EBC404D9E3EBE3ED49F7FD210000FD09D9ED18
:202DC00041444DF7FD09D9CB7A2802FD09CB78F7280119EBFD7C195059444DE12704E9CDE1
:202DE000FC2E00CFD6EFFECF53E9FE210002E5CFB1EDFE2702ED53EA67ED43EC67ED5BEA2C
:202E000067ED4BEC67CD3E2F00CCCA1F2E21F600E5CD051A270221F600E5CD79052702ED35
:202E20005BEA67ED4BEC67C5D5CD6C2E2704CF6CE7FBCF00E1F8CD812EED5BEA67ED4BEC31
:202E400067C5D5CFFDEEFE2704CC2BCCCA612E21F700E5CD051A270221F700E5CD790527F1
:202E60002C900010002000400080010FDE1E111FCFF19C179ED73A867F9D3321100FDE5EA
:202E8000C9E1ED7BA867E9FDE178B1B220197BFE203014D1E1B7CAAF2647CB2CCB1DCB1A46
:202EA000CB1B10F6C3AF26E1E17CB7F2A72601FFFF11FFFFFFDE9FFFF090000100000FFEFE1
:202EC00090000000000FFEF090000000000FFEF090000700000FF00080000010000C75369
:202EE000E0FFC7EBEFFEC764E0FFFDE1E17AB4577BB55FE178B44779B54FFDE93EC321326C
:202F00002F3220CE2221CE3270CE2271CE3280CE2281CE32A0CE22A1CE32B0CE22B1CE32DB
:202F2000D0CE22D1CE32E0CE22E1CE32F0CE22F1CEC921F100E5CD051A2702ED5DC92101A6
:202F400000CD2D1EC82DC9ED77F53EFBED67CF62E4FB3EFBED67CFC1E6FBCF2DE7FBCD56A6
:202F60002CBE6A02A66E028E7202000000F1ED67C9000000000000000000000000000000D5
:202F8000000000000000000000000000000000000000000000000000000000000000000031
:202FA000000000000000000000000000000000000000000000000000000000000000000011
:202FC0000000000000000000000000000000000000000000000000000000000000000000F1
:202FE0000000000000000000000000000000000000000000000000000000000000000000D1
:203000000000000000000000000000000000000000000000000000000000000000000000B0
:20302000000000000000000000000000000000000000000000000000000000000000000090
:20304000000000000000000000000000000000000000000000000000000000000000000070
:20306000000000000000000000000000000000000000000000000000000000000000000050
:20308000000000000000000000000000000000000000000000000000000000000000000030
:2030A000000000000000000000000000000000000000000000000000000000000000000010
:2030C0000000000000000000000000000000000000000000000000000000000000000000F0
:2030E0000000000000000000000000000000000000000000000000000000000000000000D0
:2031000000000000000000000000000000000000000000000000000000000000000000000AF
```

```
:20312000000000000000000000000000000000000000000000000000000000008F
:20314000000000000000000000000000000000000000000000000000000000006F
:20316000000000000000000000000000000000000000000000000000000000004F
:20318000000000000000000000000000000000000000000000000000000000002F
:2031A000000000000000000000000000000000000000000000000000000000000F
:2031C0000000000000000000000000000000000000000000000000000000000EF
:2031E0000000000000000000000000000000000000000000000000000000000CF
:20320000000000000000000000000000000000000000000000000000000000000AE
:20322000000000000000000000000000000000000000000000000000000000008E
:20324000000000000000000000000000000000000000000000000000000000006E
:20326000000000000000000000000000000000000000000000000000000000004E
:20328000000000000000000000000000000000000000000000000000000000002E
:2032A000000000000000000000000000000000000000000000000000000000000E
:2032C0000000000000000000000000000000000000000000000000000000000EE
:2032E0000000000000000000000000000000000000000000000000000000000CE
:20330000000000000000000000000000000000000000000000000000000000000AD
:20332000000000000000000000000000000000000000000000000000000000008D
:20334000000000000000000000000000000000000000000000000000000000006D
:20336000000000000000000000000000000000000000000000000000000000004D
:20338000000000000000000000000000000000000000000000000000000000002D
:2033A000000000000000000000000000000000000000000000000000000000000D
:2033C0000000000000000000000000000000000000000000000000000000000ED
:2033E0000000000000000000000000000000000000000000000000000000000CD
:20340000000000000000000000000000000000000000000000000000000000000AC
:20342000000000000000000000000000000000000000000000000000000000008C
:20344000000000000000000000000000000000000000000000000000000000006C
:20346000000000000000000000000000000000000000000000000000000000004C
:20348000000000000000000000000000000000000000000000000000000000002C
:2034A000000000000000000000000000000000000000000000000000000000000C
:2034C0000000000000000000000000000000000000000000000000000000000EC
:2034E0000000000000000000000000000000000000000000000000000000000CC
:20350000000000000000000000000000000000000000000000000000000000000AB
:20352000000000000000000000000000000000000000000000000000000000008B
:20354000000000000000000000000000000000000000000000000000000000006B
:20356000000000000000000000000000000000000000000000000000000000004B
:20358000000000000000000000000000000000000000000000000000000000002B
:2035A000000000000000000000000000000000000000000000000000000000000B
:2035C0000000000000000000000000000000000000000000000000000000000EB
:2035E0000000000000000000000000000000000000000000000000000000000CB
:20360000000000000000000000000000000000000000000000000000000000000AA
:20362000000000000000000000000000000000000000000000000000000000008A
:20364000000000000000000000000000000000000000000000000000000000006A
:20366000000000000000000000000000000000000000000000000000000000004A
:20368000000000000000000000000000000000000000000000000000000000002A
:2036A000000000000000000000000000000000000000000000000000000000000A
:2036C0000000000000000000000000000000000000000000000000000000000EA
:2036E0000000000000000000000000000000000000000000000000000000000CA
:20370000000000000000000000000000000000000000000000000000000000000A9
:203720000000000000000000000000000000000000000000000000000000000089
:203740000000000000000000000000000000000000000000000000000000000069
:203760000000000000000000000000000000000000000000000000000000000049
:203780000000000000000000000000000000000000000000000000000000000029
:2037A0000000000000000000000000000000000000000000000000000000000009
:2037C00000000000000000000000000000000000000000000000000000000000E9
:2037E00000000000000000000000000000000000000000000000000000000000C9
:2038000000000000000000000000000000000000000000000000000000000000A8
:203820000000000000000000000000000000000000000000000000000000000088
```

```
:20384000000000000000000000000000000000000000000000000000000000000068
:20386000000000000000000000000000000000000000000000000000000000000048
:20388000000000000000000000000000000000000000000000000000000000000028
:2038A000000000000000000000000000000000000000000000000000000000000008
:2038C0000000000000000000000000000000000000000000000000000000000000E8
:2038E00000000000000000000000000000000000000000000000000000G0000000C8
:203900000000000000000000000000000000000000000000000000000000000000A7
:20392000000000000000000000000000000000000000000000000000000000000087
:20394000000000000000000000000000000000000000000000000000000000000067
:20396000000000000000000000000000000000000000000000000000000000000047
:20398000000000000000000000000000000000000000000000000000000000000027
:2039A000000000000000000000000000000000000000000000000000000000000007
:2039C0000000000000000000000000000000000000000000000000000000000000E7
:2039E0000000000000000000000000000000000000000000000000000000000000C7
:203A0000000000000000000000000000000000000000000000000000000000000A6
:203A2000000000000000000000000000000000000000000000000000000000000086
:203A4000000000000000000000000000000000000000000000000000000000000066
:203A6000000000000000000000000000000000000000000000000000000000000046
:203A8000000000000000000000000000000000000000000000000000000000000026
:203AA000000000000000000000000000000000000000000000000000000000000006
:203AC0000000000000000000000000000000000000000000000000000000000000E6
:203AE0000000000000000000000000000000000000000000000000000000000000C6
:203B000000000000000000000000000000000000000000000000000000000000000A5
:203B2000000000000000000000000000000000000000000000000000000000000085
:203B4000000000000000000000000000000000000000000000000000000000000065
:203B6000000000000000000000000000000000000000000000000000000000000045
:203B8000000000000000000000000000000000000000000000000000000000000025
:203BA000000000000000000000000000000000000000000000000000000000000005
:203BC0000000000000000000000000000000000000000000000000000000000000E5
:203BE0000000000000000000000000000000000000000000000000000000000000C5
:203C0000000000000000000000000000000000000000000000000000000000000A4
:203C2000000000000000000000000000000000000000000000000000000000000084
:203C4000000000000000000000000000000000000000000000000000000000000064
:203C6000000000000000000000000000000000000000000000000000000000000044
:203C8000000000000000000000000000000000000000000000000000000000000024
:203CA000000000000000000000000000000000000000000000000000000000000004
:203CC0000000000000000000000000000000000000000000000000000000000000E4
:203CE0000000000000000000000000000000000000000000000000000000000000C4
:203D0000000000000000000000000000000000000000000000000000000000000A3
:203D2000000000000000000000000000000000000000000000000000000000000083
:203D4000000000000000000000000000000000000000000000000000000000000063
:203D6000000000000000000000000000000000000000000000000000000000000043
:203D8000000000000000000000000000000000000000000000000000000000000023
:203DA000000000000000000000000000000000000000000000000000000000000003
:203DC0000000000000000000000000000000000000000000000000000000000000E3
:203DE0000000000000000000000000000000000000000000000000000000000000C3
:203E0000000000000000000000000000000000000000000000000000000000000A2
:203E2000000000000000000000000000000000000000000000000000000000000082
:203E4000000000000000000000000000000000000000000000000000000000000062
:203E6000000000000000000000000000000000000000000000000000000000000042
:203E8000000000000000000000000000000000000000000000000000000000000022
:203EA000000000000000000000000000000000000000000000000000000000000002
:203EC0000000000000000000000000000000000000000000000000000000000000E2
:203EE0000000000000000000000000000000000000000000000000000000000000C2
:203F0000000000000000000000000000000000000000000000000000000000000A1
:203F2000000000000000000000000000000000000000000000000000000000000081
:203F4000000000000000000000000000000000000000000000000000000000000061
```

```
:203F60000000000000000000000000000000000000000000000000000000000000000041
:203F80000000000000000000000000000000000000000000000000000000000000000021
:203FA0000000000000000000000000000000000000000000000000000000000000000001
:203FC00000000000000000000000000000000000000000000000000000000000000000E1
:203FE00000000000000000000000000000000000000000000000000000000000000000C1
:2040000000000000000000000000000000000000000000000000000000000000000000A0
:204020000000000000000000000000000000000000000000000000000000000000000080
:204040000000000000000000000000000000000000000000000000000000000000000060
:204060000000000000000000000000000000000000000000000000000000000000000040
:204080000000000000000000000000000000000000000000000000000000000000000020
:2040A0000000000000000000000000000000000000000000000000000000000000000000
:2040C00000000000000000000000000000000000000000000000000000000000000000E0
:2040E00000000000000000000000000000000000000000000000000000000000000000C0
:20410000000000000000000000000000000000000000000000000000000000000000009F
:2041200000000000000000000000000000000000000000000000000000000000000000 7F
:20414000000000000000000000000000000000000000000000000000000000000000005F
:20416000000000000000000000000000000000000000000000000000000000000000003F
:20418000000000000000000000000000000000000000000000000000000000000000001F
:2041A00000000000000000000000000000000000000000000000000000000000000000FF
:2041C00000000000000000000000000000000000000000000000000000000000000000DF
:2041E00000000000000000000000000000000000000000000000000000000000000000BF
:20420000000000000000000000000000000000000000000000000000000000000000009E
:20422000000000000000000000000000000000000000000000000000000000000000007E
:20424000000000000000000000000000000000000000000000000000000000000000005E
:20426000000000000000000000000000000000000000000000000000000000000000003E
:20428000000000000000000000000000000000000000000000000000000000000000001E
:2042A00000000000000000000000000000000000000000000000000000000000000000FE
:2042C00000000000000000000000000000000000000000000000000000000000000000DE
:2042E00000000000000000000000000000000000000000000000000000000000000000BE
:20430000000000000000000000000000000000000000000000000000000000000000009D
:20432000000000000000000000000000000000000000000000000000000000000000007D
:20434000000000000000000000000000000000000000000000000000000000000000005D
:20436000000000000000000000000000000000000000000000000000000000000000003D
:20438000000000000000000000000000000000000000000000000000000000000000001D
:2043A00000000000000000000000000000000000000000000000000000000000000000FD
:2043C00000000000000000000000000000000000000000000000000000000000000000DD
:2043E00000000000000000000000000000000000000000000000000000000000000000BD
:20440000000000000000000000000000000000000000000000000000000000000000009C
:20442000000000000000000000000000000000000000000000000000000000000000007C
:20444000000000000000000000000000000000000000000000000000000000000000005C
:20446000000000000000000000000000000000000000000000000000000000000000003C
:20448000000000000000000000000000000000000000000000000000000000000000001C
:2044A00000000000000000000000000000000000000000000000000000000000000000FC
:2044C00000000000000000000000000000000000000000000000000000000000000000DC
:2044E00000000000000000000000000000000000000000000000000000000000000000BC
:20450000000000000000000000000000000000000000000000000000000000000000009B
:20452000000000000000000000000000000000000000000000000000000000000000007B
:20454000000000000000000000000000000000000000000000000000000000000000005B
:20456000000000000000000000000000000000000000000000000000000000000000003B
:20458000000000000000000000000000000000000000000000000000000000000000001B
:2045A00000000000000000000000000000000000000000000000000000000000000000FB
:2045C00000000000000000000000000000000000000000000000000000000000000000DB
:2045E00000000000000000000000000000000000000000000000000000000000000000BB
:20460000000000000000000000000000000000000000000000000000000000000000009A
:20462000000000000000000000000000000000000000000000000000000000000000007A
:20464000000000000000000000000000000000000000000000000000000000000000005A
:20466000000000000000000000000000000000000000000000000000000000000000003A
```

```
:20468000000000000000000000000000000000000000000000000000000000000001A
:2046A00000000000000000000000000000000000000000000000000000000000000FA
:2046C00000000000000000000000000000000000000000000000000000000000000DA
:2046E00000000000000000000000000000000000000000000000000000000000000BA
:204700000000000000000000000000000000000000000000000000000000000000099
:204720000000000000000000000000000000000000000000000000000000000000079
:204740000000000000000000000000000000000000000000000000000000000000059
:204760000000000000000000000000000000000000000000000000000000000000039
:204780000000000000000000000000000000000000000000000000000000000000019
:2047A0000000000000000000000000000000000000000000000000000000000000F9
:2047C0000000000000000000000000000000000000000000000000000000000000D9
:2047E0000000000000000000000000000000000000000000000000000000000000B9
:204800000000000000000000000000000000000000000000000000000000000000098
:204820000000000000000000000000000000000000000000000000000000000000078
:204840000000000000000000000000000000000000000000000000000000000000058
:204860000000000000000000000000000000000000000000000000000000000000038
:204880000000000000000000000000000000000000000000000000000000000000018
:2048A0000000000000000000000000000000000000000000000000000000000000F8
:2048C0000000000000000000000000000000000000000000000000000000000000D8
:2048E0000000000000000000000000000000000000000000000000000000000000B8
:204900000000000000000000000000000000000000000000000000000000000000097
:204920000000000000000000000000000000000000000000000000000000000000077
:204940000000000000000000000000000000000000000000000000000000000000057
:204960000000000000000000000000000000000000000000000000000000000000037
:204980000000000000000000000000000000000000000000000000000000000000017
:2049A0000000000000000000000000000000000000000000000000000000000000F7
:2049C0000000000000000000000000000000000000000000000000000000000000D7
:2049E0000000000000000000000000000000000000000000000000000000000000B7
:204A00000000000000000000000000000000000000000000000000000000000000096
:204A20000000000000000000000000000000000000000000000000000000000000076
:204A40000000000000000000000000000000000000000000000000000000000000056
:204A60000000000000000000000000000000000000000000000000000000000000036
:204A80000000000000000000000000000000000000000000000000000000000000016
:204AA0000000000000000000000000000000000000000000000000000000000000F6
:204AC0000000000000000000000000000000000000000000000000000000000000D6
:204AE0000000000000000000000000000000000000000000000000000000000000B6
:204B00000000000000000000000000000000000000000000000000000000000000095
:204B20000000000000000000000000000000000000000000000000000000000000075
:204B40000000000000000000000000000000000000000000000000000000000000055
:204B60000000000000000000000000000000000000000000000000000000000000035
:204B80000000000000000000000000000000000000000000000000000000000000015
:204BA0000000000000000000000000000000000000000000000000000000000000F5
:204BC0000000000000000000000000000000000000000000000000000000000000D5
:204BE0000000000000000000000000000000000000000000000000000000000000B5
:204C00000000000000000000000000000000000000000000000000000000000000094
:204C20000000000000000000000000000000000000000000000000000000000000074
:204C40000000000000000000000000000000000000000000000000000000000000054
:204C60000000000000000000000000000000000000000000000000000000000000034
:204C80000000000000000000000000000000000000000000000000000000000000014
:204CA0000000000000000000000000000000000000000000000000000000000000F4
:204CC0000000000000000000000000000000000000000000000000000000000000D4
:204CE0000000000000000000000000000000000000000000000000000000000000B4
:204D00000000000000000000000000000000000000000000000000000000000000093
:204D20000000000000000000000000000000000000000000000000000000000000073
:204D40000000000000000000000000000000000000000000000000000000000000053
:204D60000000000000000000000000000000000000000000000000000000000000033
:204D80000000000000000000000000000000000000000000000000000000000000013
```

A11

```
:204DA00000000000000000000000000000000000000000000000000000000000000000F3
:204DC00000000000000000000000000000000000000000000000000000000000000000D3
:204DE00000000000000000000000000000000000000000000000000000000000000000B3
:204E000000000000000000000000000000000000000000000000000000000000000000092
:204E2000000000000000000000000000000000000000000000000000000000000000000072
:204E4000000000000000000000000000000000000000000000000000000000000000000052
:204E6000000000000000000000000000000000000000000000000000000000000000000032
:204E8000000000000000000000000000000000000000000000000000000000000000000012
:204EA00000000000000000000000000000000000000000000000000000000000000000F2
:204EC00000000000000000000000000000000000000000000000000000000000000000D2
:204EE00000000000000000000000000000000000000000000000000000000000000000B2
:204F000000000000000000000000000000000000000000000000000000000000000000091
:204F2000000000000000000000000000000000000000000000000000000000000000000071
:204F4000000000000000000000000000000000000000000000000000000000000000000051
:204F6000000000000000000000000000000000000000000000000000000000000000000031
:204F8000000000000000000000000000000000000000000000000000000000000000000011
:204FA00000000000000000000000000000000000000000000000000000000000000000F1
:204FC00000000000000000000000000000000000000000000000000000000000000000D1
:204FE00000000000000000000000000000000000000000000000000000000000000000B1
:2050000000000000000000000000000000000000000000000000000000000000000000090
:2050200000000000000000000000000000000000000000000000000000000000000000070
:2050400000000000000000000000000000000000000000000000000000000000000000050
:2050600000000000000000000000000000000000000000000000000000000000000000030
:2050800000000000000000000000000000000000000000000000000000000000000000010
:2050A00000000000000000000000000000000000000000000000000000000000000000F0
:2050C00000000000000000000000000000000000000000000000000000000000000000D0
:2050E00000000000000000000000000000000000000000000000000000000000000000B0
:205100000000000000000000000000000000000000000000000000000000000000000008F
:205120000000000000000000000000000000000000000000000000000000000000000006F
:205140000000000000000000000000000000000000000000000000000000000000000004F
:205160000000000000000000000000000000000000000000000000000000000000000002F
:205180000000000000000000000000000000000000000000000000000000000000000000F
:2051A00000000000000000000000000000000000000000000000000000000000000000EF
:2051C00000000000000000000000000000000000000000000000000000000000000000CF
:2051E00000000000000000000000000000000000000000000000000000000000000000AF
:205200000000000000000000000000000000000000000000000000000000000000000008E
:205220000000000000000000000000000000000000000000000000000000000000000006E
:205240000000000000000000000000000000000000000000000000000000000000000004E
:205260000000000000000000000000000000000000000000000000000000000000000002E
:20528000000000000000000000000000000000000000000000000000000000000000000E
:2052A00000000000000000000000000000000000000000000000000000000000000000EE
:2052C00000000000000000000000000000000000000000000000000000000000000000CE
:2052E00000000000000000000000000000000000000000000000000000000000000000AE
:205300000000000000000000000000000000000000000000000000000000000000000008D
:205320000000000000000000000000000000000000000000000000000000000000000006D
:205340000000000000000000000000000000000000000000000000000000000000000004D
:205360000000000000000000000000000000000000000000000000000000000000000002D
:20538000000000000000000000000000000000000000000000000000000000000000000D
:2053A00000000000000000000000000000000000000000000000000000000000000000ED
:2053C00000000000000000000000000000000000000000000000000000000000000000CD
:2053E00000000000000000000000000000000000000000000000000000000000000000AD
:205400000000000000000000000000000000000000000000000000000000000000000008C
:205420000000000000000000000000000000000000000000000000000000000000000006C
:205440000000000000000000000000000000000000000000000000000000000000000004C
:205460000000000000000000000000000000000000000000000000000000000000000002C
:20548000000000000000000000000000000000000000000000000000000000000000000C
:2054A00000000000000000000000000000000000000000000000000000000000000000EC
```

```
:2054C0000000000000000000000000000000000000000000000000000000000000CC
:2054E0000000000000000000000000000000000000000000000000000000000000AC
:205500000000000000000000000000000000000000000000000000000000000008B
:205520000000000000000000000000000000000000000000000000000000000006B
:205540000000000000000000000000000000000000000000000000000000000004B
:20556000000000000000000000000000000000000000000000000G0000000000002B
:20558000000000000000000000000000000000000000000000000000000000000B
:2055A0000000000000000000000000000000000000000000000000000000000000EB
:2055C0000000000000000000000000000000000000000000000000000000000000CB
:2055E0000000000000000000000000000000000000000000000000000000000000AB
:205600000000000000000000000000000000000000000000000000000000000008A
:205620000000000000000000000000000000000000000000000000000000000006A
:205640000000000000000000000000000000000000000000000000000000000004A
:205660000000000000000000000000000000000000000000000000000000000002A
:20568000000000000000000000000000000000000000000000000000000000000A
:2056A0000000000000000000000000000000000000000000000000000000000000EA
:2056C0000000000000000000000000000000000000000000000000000000000000CA
:2056E0000000000000000000000000000000000000000000000000000000000000AA
:20570000000000000000000000000000000000000000000000000000000000000089
:20572000000000000000000000000000000000000000000000000000000000000069
:20574000000000000000000000000000000000000000000000000000000000000049
:20576000000000000000000000000000000000000000000000000000000000000029
:20578000000000000000000000000000000000000000000000000000000000000009
:2057A00000000000000000000000000000000000000000000000000000000000000E9
:2057C00000000000000000000000000000000000000000000000000000000000000C9
:2057E00000000000000000000000000000000000000000000000000000000000000A9
:20580000000000000000000000000000000000000000000000000000000000000088
:20582000000000000000000000000000000000000000000000000000000000000068
:20584000000000000000000000000000000000000000000000000000000000000048
:20586000000000000000000000000000000000000000000000000000000000000028
:20588000000000000000000000000000000000000000000000000000000000000008
:2058A00000000000000000000000000000000000000000000000000000000000000E8
:2058C00000000000000000000000000000000000000000000000000000000000000C8
:2058E00000000000000000000000000000000000000000000000000000000000000A8
:20590000000000000000000000000000000000000000000000000000000000000087
:20592000000000000000000000000000000000000000000000000000000000000067
:20594000000000000000000000000000000000000000000000000000000000000047
:20596000000000000000000000000000000000000000000000000000000000000027
:20598000000000000000000000000000000000000000000000000000000000000007
:2059A00000000000000000000000000000000000000000000000000000000000000E7
:2059C00000000000000000000000000000000000000000000000000000000000000C7
:2059E00000000000000000000000000000000000000000000000000000000000000A7
:205A0000000000000000000000000000000000000000000000000000000000000086
:205A2000000000000000000000000000000000000000000000000000000000000066
:205A4000000000000000000000000000000000000000000000000000000000000046
:205A6000000000000000000000000000000000000000000000000000000000000026
:205A8000000000000000000000000000000000000000000000000000000000000006
:205AA00000000000000000000000000000000000000000000000000000000000000E6
:205AC00000000000000000000000000000000000000000000000000000000000000C6
:205AE00000000000000000000000000000000000000000000000000000000000000A6
:205B0000000000000000000000000000000000000000000000000000000000000085
:205B2000000000000000000000000000000000000000000000000000000000000065
:205B4000000000000000000000000000000000000000000000000000000000000045
:205B6000000000000000000000000000000000000000000000000000000000000025
:205B8000000000000000000000000000000000000000000000000000000000000005
:205BA00000000000000000000000000000000000000000000000000000000000000E5
:205BC00000000000000000000000000000000000000000000000000000000000000C5
```

```
:205BE0000000000000000000000000000000000000000000000000000000000000A5
:205C000000000000000000000000000000000000000000000000000000000000084
:205C20000000000000000000000000000000000000000000000000000000000000064
:205C40000000000000000000000000000000000000000000000000000000000000044
:205C60000000000000000000000000000000000000000000000000000000000000024
:205C80000000000000000000000000000000000000000000000000000000000000004
:205CA00000000000000000000000000000000000000000000000000000000000000E4
:205CC00000000000000000000000000000000000000000000000000000000000000C4
:205CE00000000000000000000000000000000000000000000000000000000000000A4
:205D0000000000000000000000000000000000000000000000000000000000000083
:205D2000000000000000000000000000000000000000000000000000000000000063
:205D4000000000000000000000000000000000000000000000000000000000000043
:205D6000000000000000000000000000000000000000000000000000000000000023
:205D8000000000000000000000000000000000000000000000000000000000000003
:205DA0000000000000000000000000000000000000000000000000000000000000E3
:205DC0000000000000000000000000000000000000000000000000000000000000C3
:205DE0000000000000000000000000000000000000000000000000000000000000A3
:205E0000000000000000000000000000000000000000000000000000000000000082
:205E2000000000000000000000000000000000000000000000000000000000000062
:205E4000000000000000000000000000000000000000000000000000000000000042
:205E6000000000000000000000000000000000000000000000000000000000000022
:205E8000000000000000000000000000000000000000000000000000000000000002
:205EA0000000000000000000000000000000000000000000000000000000000000E2
:205EC0000000000000000000000000000000000000000000000000000000000000C2
:205EE0000000000000000000000000000000000000000000000000000000000000A2
:205F0000000000000000000000000000000000000000000000000000000000000081
:205F2000000000000000000000000000000000000000000000000000000000000061
:205F4000000000000000000000000000000000000000000000000000000000000041
:205F6000000000000000000000000000000000000000000000000000000000000021
:205F8000000000000000000000000000000000000000000000000000000000000001
:205FA0000000000000000000000000000000000000000000000000000000000000E1
:205FC0000000000000000000000000000000000000000000000000000000000000C1
:205FE0000000000000000000000000000000000000000000000000000000000000A1
:2060000000000000000000000000000000000000000000000000000000000000080
:2060200000000000000000000000000000000000000000000000000000000000060
:2060400000000000000000000000000000000000000000000000000000000000040
:206060000101010101010101010101010101010101010101010101010101010100
:2060800001010101010101010101010101010101010101010101010101010101E0
:2060A00001010101010101010101010101010101010101010101010101010101C0
:2060C000010101010101010101010100000000010101010101010101010101011A4
:2060E000000000000000000000000000000000000000000000000000000000000A0
:20610000D9210000CDD529EFCF18ECF9EFCFB9EEF9EFCF6CEEF9EFCFBEEDF926007D32B6A3
:2061200074EF3E0132FDC0EF3E0032FCC0EF3E0032FBC0EF3E0032F8C0EF3E0032FAC0EF7A
:206140003E0032F9C0EF3E00320175EF3E00320375EF3E00320275EFCF20E6FEEFCF5CE3D5
:20616000FE228174EF116400010000C5D5CFFEE2FA2704EF2AEB74E52EB22600E52E782623
:20618000000E5CFBBEFFD2706EF21000022E974EF21000022E774EF11B8FE018143ED53E3BD
:2061A00074ED43E574EF11E1FA018B43ED53DF74ED43E174EFCF7FE2FEEFED5BCBC1ED4B08
:2061C000CDC1C5D5CFFEE2FA2704EF210000E5CFCCE2FE2702EFCF7CE1FEEF2AB5C1E52A73
:2061E000B3C1E5CFDEE0FE2704ED53C7C1ED43C9C1EFCF7FE2FEEFCF09E2FEEFCF18E7F994
:20620000EF21FC1822B974EF2AB974E5210000E5C402E5FDE1E1E5111DE2D5FDE92704EFA6
:20622000118070010000C5D5CF19E1FB2704EF218D2922C174EF21AD2922BF74EF21CA2978
:2062400022BB74EF21F42822BD74EF217F0022B774EF210000221EC0EF210000221CC0EF85
:2062600011B8FE019543ED530475ED430675EFED5BF2C0ED4BF4C0C5D5210200EB7A17ED1F
:20628000062444DCDAB2DC5D5213F68CD9C2D00CD902D0021D374CD822D00EF21D374CD9C40
:2062A0002D00C5D5ED5BF2C0ED4BF4C0CD642DC5D521D374CD9C2D00C5B2D00CD4D2D009F
:2062C00021D374CD822D00EFED5BF2C0ED4BF4C0C5D5210200EB7A17ED62444DCDD42CC55A
:2062E000D521D374CD9C2D00CD902D0021CF74CD822D00EF210000228374EF110A802A8301
```

A14

```
:2063000074293FFCED52ED62CCCA3EE3C31AE3EF2A837423228374C3FAE2EFED5B83742166
:20632000F6FF19EB3003CDC82C002929EB2185741911000001000CDC02C00C30FE3EF2170
:206340003F68CD9C2D00ED538574ED438774EF00EF210100CCCA46EFEF218872E521F401CC
:20636000E5216400E5CD422BC318E4EF212FC1E5CF2FE7FD27022227C1CCCAE3E3EF212F40
:20638000C1E52A27C1E5CF39EEFD2704CCCAE3E3EF212FC1E5CF02E7FD2702EB210000B760
:2063A000ED52CC2BCCCABEE3212FC1E5CF19E7FD2702E5CFBEEDF9D1B7ED52CC2BCCC2D50C
:2063C000E3212FC1E5CF19E7FD2702EB218000B7ED52CC2BCCCAE3E3EF212FC1E5CF9DE9E0
:2063E000FD2702EF2ADBC1CF52EEFAC5D5110060016A47CD5B2D00CFA2E8FE2704CD4A1AF4
:20640000000EB7A17ED62444DED53F2C0ED43F4C0218E720602CD932BEF21A06EE521E80387
:20642000E5216400E5CD422BC3D5E6EF21CF74CD9C2D00C5D5CF8AE1FA2704CCCACDE6EF3B
:20644000213F68CD9C2D00C5D5ED5B8574ED4B8774CD4D2D00ED538974ED438B74EF21000D
:20646000000E5CFCCE2FE2702EF110200010000C5D5CFFEE2FA2704EFCF7CE1FEEFED5BB71B
:20648000C121FF00B7ED52CC2BCCC29AE4ED5BB7C1210000B7ED52CC2BCCCABBE4EFCF7CE5
:2064A000E1FEEFED5B8374210500B7ED52C2BBE4EF210000E5CFCCE2FE2702EF2AB5C1E545
:2064C0002AB3C1E5CFDEE0FE2704ED53C7C1ED43C9C1EFED5BB9C121FF00B7ED52CC2BCC77
:2064E000C2F0E4ED5BB9C1210000B7ED52CC2BCCCA02E5EF11B8FE018143ED53C7C1ED4346
:20650000C9C1EFED5BC7C1ED4BC9C1C5D5218000CF52EEFACDAD2A00CA30E5ED5BC7C1EDEC
:206520004BC9C1C5D52180FFCF52EEFACD642A00CC2BCCCA45E5EF11B8FE018143ED53C7AF
:20654000C1ED43C9C1EFED5BE374ED4BE574C5D5218000CF52EEFACDAD2A00CA73E5ED5B4F
:20656000E374ED4BE574C5D52180FFCF52EEFACD642A00CABFE5ED5BC7C1ED4BC9C1C5D5FB
:20658000ED5BE374ED4BE574CFCDEEFA2704C5D5216400CF52EEFACFC8E7FE2704CD4A1A1C
:2065A00000E5CD83292702E52AC414116400444DF76069D1F33FFB293FFCED52ED62CCCA21
:2065C000D1E5EF11B8FE018143ED53C7C1ED43C9C1EFED5BC7C1ED4BC9C1C5D511B8FE0125
:2065E0008143CDA61E00CAF7E5110A802AE974293FFCED52ED62CCCA17E6EF2AE97423223E
:20660000E9742BEFED5BE374ED4BE574ED53C7C1ED43C9C1C32FE6EF21000022E974EFED0E
:206620005BC7C1ED4BC9C1ED53E374ED43E574EF2AEB74E52EB22600E52E782600E5CFBB12
:20664000EFFD2706EFCF7FE2FEEFED5BCBC1ED4BCDC1C5D5ED5BF2C0ED4BF4C0CD061E000A
:20666000CA92E6EFED5BF2C0ED4BF4C0C5D5210200EB7A17ED62444DCDD42CC5D521D3741B
:20668000CD9C2D00CD902D0021CF74CD822D00C3AFE6EF21D374CD9C2D00C5D5ED5BCBC147
:2066A000ED4BCDC1CD902D0021CF74CD822D00EF213F68CD9C2D00C5D5ED5B8574ED4B87C3
:2066C00074CD4D2D00ED538D74ED438F7421A66E0602CD932BEF21B86AE521E803E5212C6E
:2066E00001E5CD422BC343EFEF21D374CD9C2D00C5D5CF8AE1FA2704CCCA3BEFEF213F6828
:20670000CD9C2D00C5D5ED5B8574ED4B8774CD4D2D00ED539174ED439374EF213F68CD9CF2
:206720002D00ED5318C0ED431AC0EF210100E5CF54E3FA27022225C1EF3A0CC1B7CA5FE726
:20674000EF210000E5CF4DE0FA2702EF210100E5CF9BE0FA2702EF3E00320CC1C37BE7EF82
:20676000210000E5CF9BE0FA2702EF210100E5CF4DE0FA2702EF3E01320CC1EF210200E56D
:20678000CF54E3FA27022223C1EF210000E5CF4DE0FA2702EF210000E5CF9BE0FA2702EF65
:2067A000213F68CD9C2D00C5D5ED5B8574ED4B8774CD4D2D00ED539574ED439774EF21BED4
:2067C0006ACDAB2BEF00EF2A25C1E5CF6EE5FA27022221C1EF2A23C1E5CF6EE5FA27022247
:2067E0001FC1EFED5B18C0ED4B1AC0CF59EEFAC5D5110000017A44CFA2E8FE2704ED530854
:2068000075ED430A75EF2A21C1E5CFA5E5FA2702ED530C75ED430E75EF2A1FC1E5CF60E691
:20682000FA2702ED531075ED431275EFED5B1EC02150FB19EB3003CDC82C0029292929EBB1
:2068400021187519E5D1210875D5011000EDB0E1EFED5B0C75ED4B0E75C5D5218000CF52EA
:20686000EEFACDAD2A00CA7EE8ED5B0C75ED4B0E75C5D52180FFCF52EEFACD642A00CC2B43
:20688000CCCA98E8ED5B0C75ED4B0E75C5D51129FC018B43CDC61E00CAAAE8EF11E1FA01D6
:2068A0008B43ED530C75ED430E75EFED5BDF74ED4BE174C5D5218000CF52EEFACDAD2A0097
:2068C000CAD8E8ED5BDF74ED4BE174C5D52180FFCF52EEFACD642A00CA24E9ED5B0C75EDDB
:2068E0004B0E75C5D5ED5BDF74ED4BE174CFCDEEFA2704C5D5216400CF52EEFACFC8E7FEB5
:206900002704CD4A1A00E5CD83292702E52AC414116400444DF76069D1F33FFB293FFCED98
:2069200052ED62CCCA36E9EF11E1FA018B43ED530C75ED430E75EFED5B0C75ED4B0E75C5AB
:20694000D511E1FA018B43CDA61E00C262E9ED5B0C75ED4B0E75C5D51129FC018B43CDA673
:206960001E00CA73E91101802AE774293FFCED52ED62CCCA93E9EF2AE7742322E7742BEF8A
:20698000ED5BDF74ED4BE174ED530C75ED430E75C3ABE9EF21000022E774EFED5B0C75EDD2
:2069A0004B0E75ED53DF74ED43E174EF213F68CD9C2D00C5D5ED5B8574ED4B8774CD4D2D4F
:2069C00000ED539974ED439B74EF3AFAC0B7CA6CEAEFED5B1EC0210000B7ED52C202EAEFA8
:2069E000210100E5CF37EFF92702EF210000221CC0EFED5BC7C1ED4BC9C1ED53ED74ED4319
:206A00000EF74EF3A0375B7CA0FEAEFCFBEE6F9EFCF50EFF8EFCFD1E5F9EF3A0175B7CA5DBE
```

```
:206A2000EAEF1106002A1EC0B7ED52EB2150FB19EB3003CDC82C0029292929EB21187519C3
:206A4000110400195E2356234E2346ED530475ED430675EF21FFFF221EC0C36CEAEF11B814
:206A6000FE019543ED530475ED430675EF3AF9C0B7CA44ECEFED5B1EC0210000B7ED52C25A
:206A80009AEAEFED5BC7C1ED4BC9C1ED53ED74ED43EF74EF210000221CC0EF2A1EC0CF5297
:206AA000EEFA2ADBC1C5D5CF52EEFACFA2E8FE27042AD7C1C5D5CF52EEFAC5D5210200CF12
:206AC00052EEFACFA2E8FE2704CDAD2A00CA1EEBEF2AD9C1CF52EEFAC5D511000001C84211
:206AE000CFA2E8FE2704C5D5ED5BED74ED4BEF74CD5B2D00CFCDEEFA2704C5D5ED5B0C75CF
:206B0000ED4B0E75CD972A00CA13EBEFCFBEE6F9C31EEBEF210000E5CF37EFF92702EF2A18
:206B20001EC0CF52EEFAC5D52ADBC1CF52EEFACFA2E8FE27042AD7C1C5D5CF52EEFAC5D584
:206B4000210200CF52EEFACFA2E8FE2704CD642A00CA94EB2A1EC0CF52EEFAC5D511000027
:206B6000018040CFCDEEFA27042ADBC1C5D5CF52EEFACFA2E8FE27042AD7C1C5D5CF52EE4F
:206B8000FAC5D5210200CF52EEFACFA2E8FE2704CDAD2A00CAA2EBEF210000E5CF37EFF9D5
:206BA0002702EF2A1EC0CF52EEFAC5D5110000018040CFCDEEFA27042ADBC1C5D5CF52EE22
:206BC000FACFA2E8FE27042AD7C1C5D5CF52EEFAC5D5210200CF52EEFACFA2E8FE2704CDBF
:206BE000642A00CA19ECEFED5B0C75ED4B0E75C5D5ED5BED74ED4BEF74CD972A00CA0EEC95
:206C0000EF210100E5CFC0EFF92702C319ECEF210000E5CFC0EFF92702EFCF07E7F9EF2AC3
:206C2000C774CF52EEFAC5D5ED5B1075ED4B1275CD972A00CA44ECEF3E0132FBC0EF21FF38
:206C4000FF221EC0EF213F68CD9C2D00C5D5ED5B8574ED4B8774CD4D2D00ED53A174ED430E
:206C6000A374EFED5BDBC1210000B7ED52C27BECEFCFB9EEF9EF3E0132FDC0EFED5B1EC05A
:206C80002ADBC1CDDD2A00ED5BD7C1F33FFB293FFCED523FED62CCCAB0ECEF1171FD016F0C
:206CA00043ED530475ED430675EF21FFFF221EC0EF2AD5C1CF52EEFAC5D511000001C842B1
:206CC000CFA2E8FE2704C5D5ED5B0C75ED4B0E75CD4E2A00CA0BEDEF3AFAC0B7C2E3EC3AA8
:206CE000F9C0B7CA04EDEF2AD5C1CF52EEFAC5D511000001C842CFA2E8FE2704ED530475C0
:206D0000ED430675EF21FFFF221EC0EF2AC974CF52EEFAC5D511000001C842CFA2E8FE2727
:206D200004C5D5ED5B0C75ED4B0E75CD972A00CA57EDEF3AFAC0B7C23EED3AF9C0B7CA504A
:206D4000EDEF1171FD018B43ED530C75ED430E75EF21FFFF221EC0EFED5B0C75ED4B0E7514
:206D6000C5D51129FC018B43CDA61E00CA76EDEF21FFFF221EC0EF3AF8C0B7CA8BEDEF21BE
:206D8000FFFF221EC0EF3E0032F8C0EFED5B1EC021FFFFB7ED52C2D1EDEF210000E5CF3739
:206DA000EFF92702EF3E0032FAC0EF3E0032F9C0EF3E0132FCC0EF3E00320175EF3E003241
:206DC0000375EF3E00320275EF2A1EC023221EC02BEF213F68CD9C2D00C5D5ED5B8574ED0B
:206DE0004B8774CD4D2D00ED539D74ED439F74EF21BE6ACDAB2BEF00EFCFB8E9F9EFED5B19
:206E0000C7C1ED4BC9C1C5D511000001C842CFC8E7FE2704C5D5110AD701A33BCFD1EEFAD8
:206E20002704CD4A1A0022DDC1EFED5B0C75ED4B0E75C5D511000001C842CFC8E7FE270466
:206E4000C5D5110AD701A33BCFD1EEFA2704CD4A1A0022DFC1EFED5B1075ED4B1275C5D50C
:206E6000110000001003FCFD1EEFA2704CD4A1A0022E1C1EFED5B0475ED4B0675C5D5216497
:206E800000CF52EEFACFC8E7FE2704C5D5110AD701A33BCFD1EEFA2704CD4A1A0022E3C12D
:206EA000EF2AFCC02600EB210100CD252A00EB2AFDC0260019E52AFBC02600EB210200CDD2
:206EC000252A00EBE1197D32E5C1EF21E6C1E5D121DDC1D5010900EDB0E1EFCF6CEEF9EFA0
:206EE00021D374CD9C2D00C5D5ED5BF2C0ED4BF4C0CD902D0021D374CD822D00EF3AFAC0C3
:206F0000B7C208EF3AF9C0B7CA1DEFEF2A1EC023221EC02BEF2A1CC023221CC02BEF213FAC
:206F200068CD9C2D00C5D5ED5B8574ED4B8774CD4D2D00ED53A574ED43A77421BE6A060209
:206F4000CD932BC350E3EFD9210000CDDF29ED45D9210000CDD529EF110000010000ED53BA
:206F6000A46AED43A66AEF110000010000ED53A86AED43AA6AEF110000010000ED53AC6AD5
:206F8000ED43AE6AEF110000010000ED53B46AED43B66AEF110000010000ED53B06AED436F
:206FA000B26AEF110000010000ED53FD74ED43FF74EF110000010000ED53F974ED43FB7413
:206FC000EF110000010000ED53F174ED43F374EF110000010000ED53F574ED43F774EF112F
:206FE0006802A1EC0293FFCED52DACE14EF21000022A26AEF1106802AA26A293FFCED5207
:207000000ED62CCCACA14C314F0EF2AA26A2322A26AC3F4EFC718E0F9EFED5BA26A2A1EC0C7
:20702000B7ED52EB2150FB19EB3003CDC82C0029292929EB211875195E2356234E2346C53F
:207040000D511000001C040CFA2E8FE2704C5D5ED5BA86AED4BAA6ACFD1EEFA2704ED53A8EC
:207060006AED43AA6AEFED5BA26A2A1EC0B7ED52EB2150FB19EB3003CDC82C00292929292E
:20708000EB21187519110400195E2356234E2346C5D511000001C040CFA2E8FE2704C5D597
:2070A000ED5BA46AED4BA66ACFD1EEFA2704ED53A46AED43A66AC3C614EF21000022A26A16
:2070C000EF1106802AA26A293FFCED52ED62CCCA01E2C3E0E0EF2AA26A2322A26AC3C0E02D
:2070E000EFED5BA26A2A1EC0B7ED52EB2150FB19EB3003CDC82C0029292929EB21187519AA
:207100005E2356234E2346C5D5ED5BA86AED4BAA6ACFCDEEFA2704C5D5ED5BA26A2A1EC0D9
:20712000B7ED52EB2150FB19EB3003CDC82C0029292929EB211875191104000195E2356238C
```

```
:207140004E2346C5D5ED5BA46AED4BA66ACFCDEEFA2704CFC8E7FE2704C5D5ED5BB46AEDFD
:207160004BB66ACFD1EEFA2704ED53B46AED43B66AEFED5BA26A2A1EC0B7ED52EB2150FBAB
:2071800019EB3003CDC82C0029292929EB211875195E2356234E2346C5D5ED5BA86AED4BC4
:2071A000AA6ACFCDEEFA2704C5D5ED5BA26A2A1EC0B7ED52EB2150FB19EB3003CDC82C00D1
:2071C00029292929EB211875195E2356234E2346C5D5ED5BA86AED4BAA6ACFCDEEFA2704B9
:2071E000CFC8E7FE2704C5D5ED5BB06AED4BB26ACFD1EEFA2704ED53B06AED43B26AC3D5A7
:20720000E0EFED5BB46AED4BB66AC5D5ED5BB06AED4BB26ACFA2E8FE2704ED53FD74ED432E
:20722000FF74EFED5B1EC02150FB19EB3003CDC82C0029292929EB21187519110C0019EDE9
:207240005BFD74ED4BFF74CDC02C00EFED5BFD74ED4BFF74C5D5ED5BA86AED4BAA6ACFC8D4
:20726000E7FE2704C5D5ED5BA46AED4BA66ACD5B2D00CFCDEEFA2704ED53F974ED43FB7476
:20728000EF21000022A26AEF1106802AA26A293FFCED52ED62CCCA25E4C3A7E2EF2AA26AF2
:2072A0002322A26AC387E2EFED5BA26A2A1EC0B7ED52EB2150FB19EB3003CDC82C0029296F
:2072C0002929EB2118751911040019 5E2356234E2346C5D5ED5BA26A2A1EC0B7ED52EB21D3
:2072E00050FB19EB3003CDC82C0029292929EB211875191104001 95E2356234E2346CFC87F
:20730000E7FE2704C5D5110000018040CFA2E8FE2704C5D5ED5BF574ED4BF774CFD1EEFAF9
:207320002704ED53F574ED43F774EFED5BA26A2A1EC0B7ED52EB2150FB19EB3003CDC82C4E
:2073400000029292929EB211875191104001 95E2356234E2346C5D5ED5BF974ED4BFB74CF33
:20736000C8E7FE2704C5D5110000018040CFA2E8FE2704C5D5ED5BF574ED4BF774CD5B2D04
:207380000 0CFCDEEFA2704ED53F574ED43F774EFED5BA26A2A1EC0B7ED52EB2150FB19EB5E
:2073A0003003CDC82C0029292929EB211875191104001 95E2356234E2346C5D5ED5BFD7451
:2073C000ED4BFF74CFC8E7FE2704C5D5ED5BA26A2A1EC0B7ED52EB2150FB19EB3003CDC84C
:2073E0002C0029292929EB211875195E2356234E2346CFC8E7FE2704C5D511000001804047
:20740000CFA2E8FE2704C5D5ED5BF574ED4BF774CD5B2D00CFCDEEFA2704ED53F574ED431F
:20742000F774C39CE2EFED5BF574ED4BF774C5D5CD24272704C5D5CD91272704C5D511008B
:2074400000012041CFC8E7FE2704ED53F574ED43F774EF110C802A1EC0293FFCED52DAC707
:20746000E5EF21000022A26AEF1106802AA26A293FFCED52ED62CCCADCE4C388E4EF2AA2FB
:207480006A2322A26AC368E4EFED5BA26A2A1EC0B7ED52EB2150FB19EB3003CDC82C002969
:2074A000292929EB21187519110C0019 5E2356234E2346C5D511000001C040CFA2E8FE278E
:2074C00004C5D5ED5BAC6AED4BAE6ACFD1EEFA2704ED53AC6AED43AE6AC37DE4EF110000EB
:2074E00001 0000ED53B46AED43B66AEF21000022A26AEF1106802AA26A293FFCED52ED62F1
:20750000CCCAA6E5C312E5EF2AA26A2322A26AC3F2E4EFED5BA26A2A1EC0B7ED52EB2150E4
:20752000FB19EB3003CDC82C0029292929EB211875195E2356234E2346C5D5ED5BA86AED70
:207540004BAA6ACFCDEEFA2704C5D5ED5BA26A2A1EC0B7ED52EB2150FB19EB3003CDC82CE2
:2075600000029292929EB21187519110C0019 5E2356234E2346C5D5ED5BAC6AED4BAE6ACFB7
:20758000CDEEFA2704CFC8E7FE2704C5D5ED5BB46AED4BB66ACFD1EEFA2704ED53B46AED0E
:2075A00043B66AC307E5EFED5BB46AED4BB66AC5D5ED5BB06AED4BB26ACFA2E8FE2704ED4D
:2075C00053F174ED43F374EFD9210000CDDF29ED45D9210000CDD529EF1115802A1EC029E1
:2075E0003FFCED52DA05E6EFED5BFD74ED4BFF74C5D511000001003FCD642A00CA05E6EF0F
:2076000003E01320375EF1115802A1EC0293FFCED52DA32E6EFED5BFD74ED4BFF74C5D51151
:20762000CDCC01CCBDCDAD2A00CA32E6EF3E01320275EF3A0275B7CA58E6EFED5BF174EDE2
:207640004BF374C5D511CDCC014C3DCD642A00CA58E6EF3E01320375EF3A0375B7CAB4E6B3
:20766000EFED5BF574ED4BF774C5D5CD24272704C5D511000001003FCDAD2A00CAB4E6EF08
:20768000ED5BFD74ED4BFF74C5D511000001 0000CD972A00CAABE6ED5BFD74ED4BFF74C5C8
:2076A000D5118FC201F5BDCD642A00CAB4E6EF3E01320175EFD9210000CDDF29ED45D92161
:2076C0000000CDD529EF1101802A11C1293FFCED52DAE9E6EF210100E5CF37EFF92702EF1A
:2076E0002100002211C1C3FDE6EF2A11C1232211C12BEF210000E5CF37EFF92702EFD921AD
:2077000000000CDDF29ED45D9210000CDD529EFD9210000CDDF29ED45D9210000CDD529EFF9
:207720000000EF21D214E5CFF6E7FB2702EF210515E5CFF6E7FB2702EF2AB6742600E5211739
:2077400015E5CFF6E7FB2704EF212D15E5CFF6E7FB2702EF21070022A06AEF1101802AA0C8
:207760006A293FFCED523FED62CCCA31E8C37CE7EF2AA06A2B2B22A06AC35AE7EFED5BA019
:207780006A21F6FF19EB3003CDC82C0029EB21B3C119DDE400EB210000B7ED52CC2BCCCA5F
:2077A000B0E7EF213E15E5CFF6E7FB2702C3D4E7EFED5BA06A21F6FF19EB3003CDC82C004D
:2077C00029EB21B3C119DDE400E5214115E5CFF6E7FB2704EF2AA06A2BEB21F6FF19EB3090
:2077E00003CDC82C0029EB21B3C119DDE400EB210000B7ED52CC2BCCCA09E8EF214415E574
:20780000CFF6E7FB2702C32EE8EF2AA06A2BEB21F6FF19EB3003CDC82C0029EB21B3C119B6
:20782000DDE400E5214815E5CFF6E7FB2704C370E7EFED5BC7C1ED4BC9C1C5D5214C15E5D1
:20784000CFF6E7FB2706EF215D15E5CFF6E7FB2702EFCF8FE6FD7D329F6AEF2A9F6A2600ED
```

A17

```
:20786000EB2E6D2600B7ED52CC2BCCC27EE82A9F6A2600EB2E4D2600B7ED52CC2BCCCA967D
:20788000E8EF3E0032FAC0EF3E0032F9C0EFCFB9EEF9EFC312E9EF2A9F6A2600EB2E6626D7
:2078A00000B7ED52CC2BCCC2BAE82A9F6A2600EB2E462600B7ED52CC2BCCCAD2E8EF3E0162
:2078C00032FAC0EF3E0032F9C0EFCFB9EEF9EFC312E9EF2A9F6A2600EB2E642600B7ED52B8
:2078E000CC2BCCC2F6E82A9F6A2600EB2E442600B7ED52CC2BCCCA0EE9EF3E0032FAC0EFC7
:207900003E0132F9C0EFCFB9EEF9EFC312E9EFC31FE7EF90EF219C15E5CFF6E7FB2702EF26
:207920002AD5C1CF52EEFAC5D511000001C842CFA2E8FE2704C5D521B815E5CFF6E7FB270B
:2079400006EF2AD7C1E521E815E5CFF6E7FB2704EF2AD9C1CF52EEFAC5D511000001C84244
:20796000CFA2E8FE2704C5D5211716E5CFF6E7FB2706EF2ADBC1E52147l6E5CFF6E7FB2719
:2079800004EF2AC974CF52EEFAC5D511000001C842CFA2E8FE2704C5D5217216E5CFF6E778
:2079A000FB2706EF21A216E5CFF6E7FB2702EFD9210000CDDF29ED45D9210000CDD529EF7E
:2079C0002AFAC02600CC2BCCCAD3E92AF9C02600CC2BCCCAF0EAEF2AFCC02600CC2BCCCA5C
:2079E00022EAEFED5B0475ED4B0675C5D5ED5BC7C1ED4BC9C1C5D5ED5B1075ED4B1275C501
:207A0000D5ED5B0C75ED4B0E75C5D5ED5B0875ED4B0A75C5D521EF16E5CFF6E7FB2716C3AB
:207A2000F0EAEF210000229D6AEF3A0175B7CA38EAEF210200229D6AEFED5B0475ED4B06C8
:207A400075C5D51171FD016F43CDA61E00CA57EAEF210300229D6AEF2AD5C1CF52EEFAC590
:207A6000D511000001C842CFA2E8FE2704C5D5ED5B0475ED4B0675CDA61E00CA85EAEF21AB
:207A80000400229D6AEF2AFBC02600EB210100B7ED52C29CEAEF210500229D6AEFED5B9D62
:207AA0006A21FAFF19EB3003CDC82C002929EB21A21419E5ED5B0475ED4B0675C5D5ED5BE2
:207AC000C7C1ED4BC9C1C5D5ED5B1075ED4B1275C5D5ED5B0C75ED4B0E75C5D5ED5B0875B9
:207AE000ED4B0A75C5D5210E17E5CFF6E7FB2718EF3AFAC0B7CA6CEBEF2AFEC12600EB215F
:207B0000FEFF19EB3003CDC82C002929EB219A1419E5ED5BF174ED4BF374C5D5ED5BF574CF
:207B2000ED4BF774C5D5ED5BFD74ED4BFF74C5D5ED5B0475ED4B0675C5D5ED5BC7C1ED4BF4
:207B4000C9C1C5D5ED5B1075ED4B1275C5D5ED5B0C75ED4B0E75C5D5ED5B0875ED4B0A7541
:207B6000C5D5214D17E5CFF6E7FB2724EF3AF9C0B7CACAEBEF2AFEC12600EB21FAFF19EBF0
:207B80003003CDC82C002929EB21A21419E5ED5B0475ED4B0675C5D5ED5BC7C1ED4BC9C13F
:207BA000C5D5ED5B1075ED4B1275C5D5ED5B0C75ED4B0E75C5D5ED5B0875ED4B0A75C5D5D1
:207BC000218317E5CFF6E7FB2718EFD9210000CDDF29ED45D9210000CDD529EF210100E574
:207BE000CF37EFF92702EF213F68CD9C2D00C5D521E803EB010000CDF021C5D5C407EB0160
:207C000000000CD902D00ED530DC1ED430FC1EFD9210000CDDF29ED45D9210000CDD529EF28
:207C2000215100E5210000E5210900E5CDCC212706EF215400E5210000E5210900E5CDCCFA
:207C4000212706EF214368CD9C2D00ED5302C1ED4304C1EF218000E5210000E5212400E5E8
:207C6000CDCC212706EF210C00E521FBC3E521D400E5CDCC212706EF211F00E5210000E57D
:207C800021AB00E5CDCC212706EF21C217E5210D00E5CFC2E7FB2704EF215500E52122C47C
:207CA000E5215500E5CDCC212706EF3E003221C0EF214000E5210000E5216600E5CDCC21FC
:207CC0002706EF21BE00E52106C1E5216700E5CDCC212706EF21FF00E5210000E521770011
:207CE000E5CDCC212706EF210000E5CF37EFF92702EF21000022llC1EF210000E5CFE9E01B
:207D0000FA2702EF210000E5CFA7E4FA2702EFCF69E1FA7D32F2C1EF210100E5CFA7E4FA20
:207D20002702EFCF6CEEF9EF218214E5218EC0E5CDF51F2704EF218214E5CDBD212702E5DA
:207D4000CFDAEDF92702EF00EF3A21C0B7CA54EDEFC348EDEF110200010000C5D5CFFEE27D
:207D6000FA2704EF00EFCF2BE5FAEB210100B7ED52C278EDEFC365EDEF218714E5218EC0FA
:207D8000E5CDF51F2704EF218714E5CDBD212702E5CFDAEDF92702EF00EF3A21C0B7CAA5D2
:207DA000EDEFC399EDEF110200010000C5D5CFFEE2FA2704EFD9210000CDDF29ED45D92143
:207DC0000000CDD529EFCF69E1FAEB210F00B7ED52D9210000CDDF29ED45D9210000CDD528
:207DE00029EFC4032228C0EF2101002226C0EF2A28C0CCCA32EEEF3E013221C0EF2A28C088
:207E00002B2228C023EF2A8EC02600E5CF29E7FA2702E5210000E521D000E5CDCC212706EE
:207E2000EF218D00E5210000E521D400E5CDCC212706EFD9210000CDDF29ED45D92100000F
:207E4000CDD529EFC4032224C0EF2100002222C0EF214D00E5210000E521D400E5CDCC21AB
:207E60002706EFD9210000CDDF29ED45D9210000CDD529EF219414E5218EC0E5CDF51F2727
:207E800004EF219414E5CDBD212702E5CFDAEDF92702EF00EF3A21C0B7CAA0EEEFC394EE94
:207EA000EF110200010000C5D5CFFEE2FA2704EFD9210000CDDF29ED45D9210000CDD5299C
:207EC000EF110000010000ED53D1C1ED43D3C1EF2124FA22D5C1EF21030022D7C1EF21F454
:207EE0000001229C1EF21780022DBC1EF21A00F22C974EF21280022C774EF210B0022EB7430
:207F0000EF2ADBC1CF52EEFAC5D5110060016A47CD5B2D00CFA2E8FE2704CD4A1A00EB7A79
:207F200017ED62444DED53F2C0ED43F4C0EFD9210000CDDF29ED45D9210000CDD529EFC40C
:207F4000003EB210100DCD403EFC403CCCA94EFEF210700E5210000E52107C1E5217000E549
:207F6000CD281F2708EF210600E5210100E52107C1E5217000E5CD281F2708EF214368CDAD
```

```
:207F80009C2D00ED53FAC1ED43FCC1EF3E0132FEC1C3B6EFEF210600E5210000E52107C1BF
:207FA000E5217000E5CD281F2708EF2100007D32FEC17D32F9C1EFD9210000CDDF29ED454C
:207FC000D9210000CDD529EFC403EB210100DCD403EFC403CCCAF818EF210700E5210100EC
:207FE000E52107C1E5217000E5CD281F2708EF210600E5210100E52107C1E5217000E5CD02
:020000020800F4
:20000000281F2708C708E0FAEF214368CD9C2D00ED53F5C1ED43F7C1EF3E0132F9C1C34372
:20002000E0EF210600E5210000E52107C1E5217000E5CD281F2708EF2100007D32FEC17D5D
:2000400032F9C1EFD9210000CDDF29ED45D9210000CDD529EFC4037D32F4C1EFC403CCCA99
:200060007BE0EF210000E5210100E52107C1E5217000E5CD281F2708C391E0EF210000E579
:20008000210000E52107C1E5217000E5CD281F2708EFD9210000CDDF29ED45D9210000CD1C
:2000A000D529EFC4037D32F3C1EFC403CCCAC9E0EF210100E5210100E52107C1E5217000D8
:2000C000E5CD281F2708C3DFE0EF210100E5210000E52107C1E5217000E5CD281F2708EF04
:2000E000D9210000CDDF29ED45D9210000CDD529EFC403CCCA49E1EFCFD9E6FBC5D51100A1
:200100000012041CFC8E7FE2704CD4A1A00EB210100DCCCCA30E1EF210100E5CF4DE0FA29
:20012000702EF210000E5CF9BE0FA2702C346E1EF210000E5CF4DE0FA2702EF210100E540
:20014000CF9BE0FA2702C35FE1EF210000E5CF4DE0FA2702EF210000E5CF9BE0FA2702EFCA
:20016000D9210000CDDF29ED45D9210000CDD529EF213000E5CDF1182702EB210F00DC2678
:2001800000D9210000CDDF29ED45D9210000CDD529EF213F68CD9C2D00ED53966AED439844
:2001A0006AEF210300395E2356234E2346C5D5118096019800CD0E1F00CAD0E1ED5B966AC1
:2001C000ED4B986AC5D5118096019800CDFE1E00CAEAE1210300395E2356234E2346C5D565
:2001E00011C0E101E400CDDE1E00CA01E2ED5B966AED4B986AC5D511C0E101E400CDCB1E89
:20020000CA0BE2EF21000022F6C0EF2AF6C0CCCA50E2EF210300395E2356234E2346C5E6
:20022000D511C0BD01F0FFCDCB1E00CA50E2EF21030039E5210500395E2356234E2346C5B3
:20024000D5118084011E00CD902D00E1CDC02C00EF2AF6C0CC2BCCCAC9E2EF210300395EC0
:200260002356234E2346C5D511C0BD01F0FFCDCB1E00CAC9E2EF213F68CD9C2D00C5D511F0
:200280008084011E00CD902D00213F68CD822D00EF213F68CD9C2D00ED53966AED43986AAE
:2002A000EF21030039E5210500395E2356234E2346C5D5118084011E00CD902D00E1CDC037
:2002C0002C00EF21010022F6C0EF210300395E2356234E2346C5D5ED5B966AED4B986ACD23
:2002E000E1F00CAF3E2EF210100D9210000CDDF29ED45EF210000C3EAE2EFC3EAE2D92109
:20030000000CDD529EF21030039E55E2356234E2346C5D5213F68CD9C2D00CD902D00E1CD
:20032000CDC02C00EF00EF210300395E2356234E2346C5D5213F68CD9C2D00CDC61E00CAA5
:200340004AE3EFCD9F1E00C326E3EFD9210000CDDF29ED45D9210000CDD529EFC403EB21B4
:200360000100B7ED52C2F9E3EF218C14E5218EC0E5CDF51F2704EF218C14E5CDBD2127028A
:20038000E5CFDAEDF92702EF00EF3A21C0B7CA95E3EFC389E3EF110200010000C5D5CFFE46
:2003A000E2FA2704EF00EFCF2BE5FAEB210000B7ED52C2B9E3EFC3A6E3EF00EFCF2BE5FA2D
:2003C000EB210100B7ED52C2CEE3EFC3BBE3EF210200E5CF3CEEF92702EF00EF2A24C0CC8D
:2003E000CAE7E3EFC3DBE3EF110200010000C5D5CFFEE2FA2704C387E4EF218E14E5218E14
:20040000C0E5CDF51F2704EF218E14E5CDBD212702E5CFDAEDF92702EF00EF3A21C0B7CAA9
:2004200026E4EFC31AE4EF110200010000C5D5CFFEE2FA2704EF00EFCF2BE5FAEB210000CE
:20044000B7ED52C24AE4EFC337E4EF00EFCF2BE5FAEB210100B7ED52C25FE4EFC34CE4EF59
:200460000210200E5CF3CEEF92702EF00EF2A24C0CCCA78E4EFC36CE4EF110200010000C5B1
:20048000D5CFFEE2FA2704EF2A2AC02600110001444DF76069E52A2BC02600EBE119D92128
:2004A0000000CDDF29ED45D9210000CDD529EFC403CCCACEE4EF210700E5210000E5210A45
:2004C000C1E5214000E5CD281F2708C3E4E4EF210700E5210100E5210AC1E5214000E5CD7B
:2004E000281F2708EFD9210000CDDF29ED45D9210000CDD529EF210100E5C405E52108C143
:20050000E5216000E5CD281F2708EFC403CC2BCCCA21E5EF217F00E521066AE5CD8B1E277D
:2005200004EFD9210000CDDF29ED45D9210000CDD529EF210000E5216000E5CD151B27047F
:20054000D9210000CDDF29ED45D9210000CDD529EFC403CF75EEFAC5D511A470019D37CF90
:20056000C8E7FE2704D9210000CDDF29ED45D9210000CDD529EFC403CF75EEFAC5D5110050
:2005800040019C3ECFC8E7FE2704C5D511000001003FCFD1EEFA2704CD4A1A00D9210000D0
:2005A000CDDF29ED45D9210000CDD529EFC403EB211B01B7ED52D252E6EFC403CF75EEFAAF
:2005C000C5D5CF2BEBFA2704ED53926AED43946AEFED5B0B19ED4B0D19C5D5ED5B926AED89
:2005E0004B946ACFC8E7FE2704C5D5ED5B0719ED4B0919CFD1EEFA2704C5D5110000014010
:2006000040C5D5ED5B926AED4B946AC5D5CF4EEBFA2708C5D5ED5B0F19ED4B1119CFC8E7D1
:20062000FE2704CFD1EEFA2704C5D511000001803FCD5B2D00CFA2E8FE2704C5D51133932B
:20064000018843CFCDEEFA2704D9210000CDDF29ED45EF1129FC018B43C349E6EFC349E657
:20066000D9210000CDD529EFC403CF75EEFAC5D5119A9901993ECFCDEEFA2704C5D51100C3
```

A19

```
:2006800000001803FCD5B2D00CFA2E8FE2704C5D51117B7015138CFCDEEFA2704C5D5CFF8B0
:2006A000E7FA2704CD291A00ED538E6AED43906AEFED5B8E6AED4B906AC5D5ED5B1719ED5C
:2006C0004B1919CD4E2A00CA1AE7EFED5B1319ED4B1519C5D5ED5B8E6AED4B906ACFCDEE2E
:2006E000FA2704C5D511000001C842CFC8E7FE2704C5D5ED5B1319ED4B1519C5D5ED5B170B
:2007000019ED4B1919CFCDEEFA2704CFA2E8FE2704D9210000CDDF29ED45EF217769CF5213
:20072000EEFAC311E7EFC311E7D9210000CDD529EF210300396E2600EB218000DCEB21074C
:200740000CD1B1900E5210500396E2600EB214000DCEB210500CD1B1900EBE119E5210596
:20076000000396E2600EB212000DCEB210300CD1B1900EBE119E5210500396E2600EB2110BB
:200780000DCEB210100CD1B1900EBE119E5210500396E2600EB210800DCEB210100CD25C3
:2007A0002A00EBE119E5210500396E2600EB210400DCEB210300CD252A00EBE119E521054B
:2007C00000396E2600EB210200DCEB210500CD252A00EBE119E5210500396E2600EB21016B
:2007E0000DCEB210700CD252A00EBE1192600D9210000CDDF29ED45210300395E2356238B
:200800004E2346C5D5CF1BE8FA2704C5D5119B20019A3ECFC8E7FE2704ED4527F61100004A
:200820003E00C40D373FED5A20023E01C40FED5A2004E6012003293015E5210A0039232346
:200840000DDE400E521EA00E5CD051A2704E1CB1F5C160062B7CB1D083E35BD3E7F30021373
:200860003DC40FCB15CB1467CB1CCB1DD40FEBD40821040039E5210F00395E2356234E23B2
:2008800046C5D511000001803FCFCDEEFA2704C5D5211300395E2356234E2346C5D5110095
:2008A0000000001803FCFD1EEFA2704CFA2E8FE2704C5D5CD75192704E1CDC02C00C406EBC410
:2008C0000000429F329F3D400EBD402210400395E2356234E2346C5D5210800395E2356234EF4
:2008E0002346C5D5CF41E9FA2708C5D5216519E52E042600E5CFACE9FA2708C5D52104002C
:20090000395E2356234E2346C5D5CF41E9FA270869607B085A556CCB149F6708D9C408FC3C
:20092000652E00CB1D11803FB7ED52B7EBED41D909444DCF5CEAFA21000409444D270AED47
:2009400045C405E3C407EBED41C409EBC403444D78D9A8F270E9A8F265E9F7D9F71976EB45
:200960000B7ED5A1822F719D9F776EBB7ED5A1817A8FA7DE9F7D9F776EBED5A180AF719D94F
:20098000F71976EBB7ED5AD9444DF7ED59D9EA97E97CD9EB1718057CD9EB173FED62D919B3
:2009A000D9ED5A76EBF3ED6A444DED45DDE5DD210000DD39C4057D3D08DDC407FDC409C412
:2009C000BE3FD7C444DE402EBE400EBED41EB78D9A8F2EFE9A8F2E4E9F7D9F71976EBB744
:2009E000ED5A1822F719D9F776EBB7ED5A1817A8FAFCE9F7D9F776EBED5A180AF719D9F710
:200A000001976EBB7ED5AD9444DF7ED59D9EA17EA7CD9444D1718067CD9444D173FED62D974
:200A2000019D9ED4AD929D9ED6A010400DD09444DE402D9EBE40019D9ED4A083D280D08E3C3
:200A4000D9444DED49FD7C444D1884EBED41D9EBDD210000DD39DDF9DDE1ED45780878B7EA
:200A6000F270EA210000ED52EB210000ED42444DAFB0200DB1201EB2202FB3C2C0EAC32977
:200A8000EBE28EEA7B5A516826000E7F184960690E78AF1866E29FEA6069AF0E77183861DA
:200AA0006A531E000E70AF1852E2B7EA6A5326001E00AF0E6F1820EB110000AF0E68183B68
:200AC000E2CCEAEB110000AF0E67180B632E001100000E60AF1824CB7D201917F3ED6A0D51
:200AE000CB7D201017F3ED6A0DCB7D200717F3ED6A0D1826B72802CBC3181FB7FCFB1F245E
:200B0000252817B7FCFB1F0C2425280EB7FCFB1F0C24252805B7FCFB1F0CB72802CBC3BB7
:200B2000150817CB19CB1D414DED45210300395E2356234E2346C5D5CF1BE8FA2704C5D5BC
:200B400011187201313FCFC8E7FE2704ED45210300395E2356234E2346C5D51100000100F6
:200B60000000CDA61E00C27FEB210300395E2356234E2346C5D5110000010080CDA61E00CA23
:200B800099EB210700395E2356234E2346C5D5110000010000CDA61E00CAA4EB1100000117
:200BA000803FED45210300395E2356234E2346C5D5110000010000CDA61E00C2D5EB210353
:200BC00000395E2356234E2346C5D5110000010080CDA61E00CAEFEB210700395E2356236F
:200BE0004E2346C5D511000001803FCDA61E00CAFBEB110000010000C3A2EB210300395E75
:200C00002356234E2346C5D5210000CF52EEFACDAD2A00CA3AEC210700395E2356234E235D
:200C200046CD4A1A00CF52EEFAC5D5210B00395E2356234E2346CDA61E00CACDEC21070048
:200C4000395E2356234E2346CD4A1A00EB210200CDDD2A00EBEB210000B7ED52CC2BCCCA1D
:200C600096EC210300395E2356234E2346CD291AC5D5CF1BE8FA2704C5D5210B00395E23C3
:200C800056234E2346CFC8E7FE2704C5D5CFFEECFA2704C3A2EB210300395E2356234E23ED
:200CA0004CD291AC5D5CF1BE8FA2704C5D5210B00395E2356234E2346CFC8E7FE2704C531
:200CC000D5CFFEECFA2704CD291AC3A2EB210300395E2356234E2346C5D5CF1BE8FA270462
:200CE000C5D5210B00395E2356234E2346CFC8E7FE2704C5D5CFFEECFA2704C3A2EB27F4BA
:200D0000CB78201F210043B7ED423017E5210C00392323DDE400E521EB00E5CD051A270481
:200D2000E1180B21FDC2B7ED423003C339EE7817ED62D400CBB86069ED6A7C37CB1D2600B6
:200D4000FE87D228EEFE7E303D656A531E00FE673006CCFC545C182AD67F3D1F3802FCFBC6
:200D60001F3804FCFBFCFB1F3808FCFBFCFBFCFBFCFB1F38055A556C26001F38055D542124
:200D800000003E001814D67E280847B7F3ED6A10FB7C656A531E00B7FCFBF5444DD406EB5D
```

A20

```
:200DA000D40421040039E5210600395E2356234E2346C5D5212E1AE52E072600E5CFACE97B
:200DC000FA2708E1CDC02C00210400395E2356234E2346C5D5CF5CEAFA2704F1C602B7609D
:200DE0006929CB1884CB101FCB1D474DEBD4086960D40AC400CC2BCCCA0CEE210800395E0B
:200E00002356234E2346D9270CD9ED4511000001803FC5D5210C00395E2356234E2346CF17
:200E2000A2E8FE2704C306EEC400CC2BCCCA39EE11E6B101617FC306EE110000010000C3BB
:200E400006EE11000001803FC306EED9210000CDB529EB7A17ED62444DCB78281CCCFCB7EF
:200E6000ED52EB210000ED42E27BEE0100CF110000ED452600EB01000060690E967CB720C8
:200E80000408C3C6EFE295EEFCFBB7FCFBB7FCFBB7FCFB0E9A7CB72818FCFB0C7CB72811DE
:200EA000FCFB0C7CB7280AFCFB0C7CB72803FCFB0C2979CB101FCB1D474DED45EFD9210033
:200EC00000CDDF29ED45D9210000CDD5293E80A8476069294C7CB7280137CB1D78D9C403C8
:200EE000EBC40544294CA8087CB7280137CB1DAF67D96779D9B9CAA6EF300279D991FE0186
:200F0000CA9AEFFE183803D9186BB71F30033FFCFB1F30053FFCFBFCFB1F30093FFCFBFC87
:200F2000FBFCFBFCFB1F300D7B5A552E0065B72819CBC318151F300B5D6A1600CCEBECEB37
:200F4000FC1807B4260028O2CBC308F261EFE3ED52D9ED5276EBCB7D201BB7F3ED6A0D1856
:200F6000014E319D9ED5A76EBAFB42809FCFB3002CBC30C280C2961CB10CB1CCB1D444DEDA3
:200F80004578E680F67F470EFF11FFFF21EC00E5CD051A2702CD7905ED45FCFB3002CBC31B
:200FA0008FAAAEF18BB08F261EFE3ED52D9ED523010D97819D9ED5AD9EBB7ED52D9EBED0A
:200FC000524776EB3708AFB52805E206F01812B22806E27CF0C3B3F0B3286DE250F0C3E3A1
:200FE000F0F317380DF317380FF31738126F3EFD18461FFB6F7918431FFB6F3EFF18391F72
:20100000FB6F3EFE1832F317F317F3CB17E21FF0F317F3173816F31738196F3EFA1819F37E
:2010200017F317F317F3176F3EF9180C1FFB6F3EFC18051FFB6F3EFB81300DCB15CB101F77
:20104000CB1D67444D08ED45CCFCEB424B08ED45171 7CB17E272F01717380917380D6F5A14
:201060003EEA18D41F6F5A3EEC18CD1F6F5A3EEB18C61717 17176F5A3EE918BCF3F3F3E29B
:20108000A6F0F3FA94F0F3FA9DF0F33EF26A531E00C338F03EF46A531E00C338F03EF36A53
:2010A000531E00C338F0F3F3F36A531E003EF1C338F0F33811FAD1F0F3FADAF0F36A53B5
:2010C0001E003EF5C338F0FB6A533EF81E00C338F06A533EF71E00C338F06A533EF61E00D3
:2010E000C338F017380D1738121738176F5A3EEDC338F01F6F3EF05AC338F01F6F5A3EEFED
:20110000C338F01F6F3EEE5AC338F0C70FE1FBEFD9210000CDDF29ED45110000010000ED44
:20112000536F69ED4371692A27C42600CF75EEFAC5D5110000019646CFC8E7FE2704C5D54A
:20114000210700395E2356234E2346CF59EEFACFA2E8FE2704C5D511000001003FCFD1EE72
:20116000FA2704CD4F1AC5D5110100010000CD4D2D00ED537369ED437569ED5B6F69ED4B9E
:201180007169C5D5110100010000CD902D00C5D5ED5B7369ED4B7569CD5B2D00CDD42CC583
:2011A000D511FF00010000CD0C1E00CAC2E1ED5B6F69ED4B7169C5D511FF00010000CD0635
:2011C0001E00CAE8E1ED5B6F69ED4B7169C5D5210100EB7A17ED62444DCD902D00ED536FDB
:2011E00069ED437169C37AE1ED5B6F69ED4B71696069ECCCCA58E2ED5B6F69ED4B7169C5B0
:20120000D5110100010000CD902D00C5D5ED5B7369ED4B7569CD5B2D00CDD42CED5373694A
:20122000ED437569ED5B6F69ED4B7169EB2600E52104C4E521A300E5CDCC2127062A05C427
:201240002600EB214000ECE52105C4E521A400E5CDCC212706C370E22A05C42600EB21BFF2
:20126000FFDCE52105C4E521A400E5CDCC2127063E0032C7C33E0032C4C33E0032C6C33E26
:20128000000032C5C33E0032C3C33E003279693E003277693E0032786921321B22C1C3213244
:2012A0001B22BFC321321B22BDC3ED5B7369ED4B7569EB2600E52101C4E521AD00E5CDCC18
:2012C000212706217F00E521066AE5CD8B1E2704217F00E5217E69E5CD8B1E2704CD331BF6
:2012E000213F68CD9C2D00ED536769ED436969213F68CD9C2D00C5D5ED5B6769ED4B696964
:20130000CD4D2D00C5D5210700395E2356234E2346C5D5210A00EB7A17ED62444DCDD42CEC
:2013200021E803C5D5EB7A17ED62444DCD5B2D00CDD42CCDFE1E00CA3DE3C3EFE221066A91
:20134000E5CDCA1D270221066AE5CDCA1D27022A27C42600CF75EEFAC5D511000001164906
:20136000CFC8E7FE2704C5D5ED5B7369ED4B7569C5D521FF00EB7A17ED62444DCDF41D00FE
:20138000C5D5210100EB7A17ED62444DCD902D00C5D5212000EB7A17ED62444DCDAB2DCF00
:2013A00059EEFAC5D511000001003FCFD1EEFA2704CFA2E8FE2704C5D5ED5B6F69ED4B7169
:2013C00069C5D5210100EB7A17ED62444DCD902D00C5D5210B00395E2356234E2346CDABDA
:2013E0002DCF59EEFACFA2E8FE2704ED536B69ED436D69ED5B6B69ED4B6D69C5D5113333D9
:201400000001733FCD642A00CA1EE4ED5B6B69ED4B6D69C5D511666601863FCDAD2A00ED45B5
:2014200003E003266693A7869B7CA3FE42A66692600EB210200EC7D3266693E003278693A8C
:201440007769B7CA59E42A66692600EB210100EC7D3266693E003277692A666926002600C3
:20146000ED452100022646811008 12A6468293FFCED52ED62CCCA07E52100022260682103
:2014800000002262681108802A6268293FFCED52ED62CCCAC5E41101002A6268CD252A0080
:2014A000ED5B6468DCCCCAB1E42A6068232260682B2A62682322266811088 0293FFCED52A8
```

```
:2014C000ED62CC20D1ED5B6068210200CDDD2A00EBEB210000B7ED52C2E8E4ED5B64682149
:2014E00006668193680C3F2E4ED5B64682166681936002A64682322646811008l293FFCED7A
:2015000052ED62CCC279E4ED45ED4521030039E5210500396E2600EB217F00DC7DE1772149
:201520000500396E2600EB2E4F2600B7ED52C24FE5210300396E2600EB216668196E2600E7
:20154000E5210500396E2600EBE1EC2600ED45210500396E2600EB2E452600B7ED52C28CE8
:20156000E5210300396E2600EB218000ECE5210500396E2600EB216668196E2600EBCCFC0B
:2015800037ED522600D1DC2600C34DE52100002600C34DE5C34DE5210300396E2600EB21B9
:2015A0008000DCE5210500396E2600EB217F00DCEB216668196E2600D17DAB6F7CAA67CC48
:2015C000CAE3E5210500396E2600EB2E452600B7ED52C2DAE5210100ED45210000C3D8E596
:2015E000C301E6210500396E2600EB2E4F2600B7ED52C2FBE5210100C3D8E5210000C3D8CA
:20160000E5C3D8E5D9210000CDD529D92100001100003E10D9ED5B5A682A5868CBC529F3CE
:2016200029F3ED4B586809EBED4B5A68ED4A225A68ED535868FCFBFCFBFCFBFCBCB1C26A4
:20164000000444D300EB7210000ED52EB210000ED42444DED41D9EB09EBD9ED49D9ED4AD9FA
:201660003D20B2D9444DCF59EEFA78E6806F78D60CE67FB547ED535468ED435668EFED5BB8
:201680005468ED4B5668D9210000CDDF29ED45D921FCFFCDD529CFD9E6FB2A5A687C1717B8
:2016A00017E680B047EBD4006960D402EF210000395E2356234E2346D9210400CDDF29ED9E
:2016C0004511214 3016583ED535C68ED435E68ED535868ED435A68ED45D9210000CDD52984
:2016E000ED5B5A682A5868CBC529F329F3ED4B586809EBED4B5A68ED4A225A68ED5358682D
:20170000FCFBFCFBFCFBFCFB4D0600CF79EEFA78D60C47ED535068ED435268EFED5B5068F8
:20172000ED4B5268D9210000CDDF29ED4527FE3E00323 7 68210000D400110A80C400293FC6
:20174000FCED52ED62CCCA68E7C40029EB21236 8193600233600C40023D400110A80293F30
:20176000FCED52ED62CC20E12702ED45ED76ED5ECD472F00CD0E20ED7EED45DDE5DD21026C
:2017800003E00D3DD7700D3DD4E00D3DD4601D3DD5E02D3DD5603D3DD6E04D3DD6605D3C6
:2017A000DD7700D3DD7E00B920D7297CE67F60474D3E80A228010CF33E80A428011CDDE10C
:2017C000ED45DDE5DD210000DD3911F0FFDC2806210000E51819111000E405444DF7ED5FE2
:2017E00059571936C3E523E5FDE1E407FDF400E1DDF9DDE1ED452A5DC42600EB210800DC78
:20180000CCCA14E8210300392323E5C405E5CF4AE8FB2704ED45C407DDE400117F80293FA3
:20182000FCED52D240E8C407E5DDE40023FDE1FDF4002BEBC40519E5C4057DE177C348E8A2
:20184000117F00C405193600ED45278027FE210000D48021800039E521020039E52100004C
:20186000E5C48D00E5C48D00E5214E22E5CF9BE8FB270C210000E521820039E521040039FC
:20188000E5210000E5CF16E8FB270821000039E5CD2E052702277F2703ED4527DEC429D436
:2018A00020C427D408210A0039E52100007DE1776F2600D414D41A21FFFFD416C40823D4CB
:2018C000082B6E2600D412EB2E252600B7ED52CCCADDE8C412EB210000B7ED52CCCA01E94E
:2018E000C425E5C42DE5C433E5C433E5C41AE5C408E5FDE1E1E511FCE8D5FDE9270AC3BC14
:20190000E8C412CC2BCCCA0DE92722ED45C4086E2600EB2E2D2600B7ED52CC2BCCC230E9AB
:20192000C4086E2600EB2E302600B7ED52CC2BCCCA46E9210A0039E5C40A7EE177C408234A
:20194000D4082B6E2600C4086E2600EB2E2A2600B7ED52C26BE9C40823D408C4202323D44E
:20196000202B2BDDE400D418C37FE9210A00E5210A0039E5C40CE5CD40232706EBD418C413
:20198000086E2600EB2E2E2600B7ED52C2DAE9C40823D408C4086E2600EB2E2A2600B7ED8B
:2019A00052C2BEE9C40823D408C4202323D4202B2BDDE400D4162101000D414C3D7E9210ACA
:2019C00000E5210A0039E5C40CE5CD40232706EBD416210100D414C3DFE921FFFFD4162133
:2019E000B0039E5C40A23D40A2B7EE177210B00396E2600E5CD3D262702EB2E6C2600B755
:201A0000ED52C221EA210100D41A210B0039E5C40A23D40A2B6E2600E5CD3D2627027DE136
:201A200077210B00396E2600C3DEEDC425E5C42DE5C433E5C433E52E252600E5C408E5FD40
:201A4000E1E1E51149EAD5FDE9270AC3A5E8C4202323D4202B2BDDE400D406C406E5CDBD17
:201A6000212702D40C110180C416293FFCED523FED62CCCA86EAC40CEBC416F33FFB293F6F
:201A8000FCED52ED62CCCA8DEAC416D40CC418EBC40CF33FFB293FFCED52D2AAEAC40CEB6D
:201AA000C418B7ED52D412C3AFEA210000D412210A00396E2600EB2E2D2600B7ED52CCCA1B
:201AC000D0EA110180C412293FFCED523FED62CCCAECEAC42FE5C42FE5C42FE5C42BE5C427
:201AE0001AE52E202600E5CD7D22270C210000D410C40CEBC410F33FFB293FFCED52ED623C
:201B0000CCCA40EBC425E5C42DE5C433E5C433E5C40E23D40E2B6E2600E5C408E5FDE1E1BD
:201B2000E51127EBD5FDE9270AC41023D410C40CEBC410F33FFB293FFCED52ED62CC20C478
:201B4000210A00396E2600EB2E2D2600B7ED52CC2BCCCA63EB110180C412293FFCED523F06
:201B6000ED62CCCA7FEBC42FE5C42FE5C42FE5C42BE5C41AE52E202600E5CD7D22270CC33C
:201B8000A5E8110080C416293FFCED52D294EB210100D416C418CCCAAAEBC416EBC418F3B2
:201BA0003FFB293FFCED52ED62CCCAB1EBC416D418C41ACC2BCCCAEDEBC42FE5C42FE5C44A
:201BC0002FE5C4262323D4262B2BDDE400E5C42DE5C422E5211700396E2600E521180039CE
```

A22

```
:201BE0006E2600E5CF63E2FC2710C329ECC42FE5C42FE5C42FE5110400C42619D42611049E
:201C000000B7ED525E2356234E2346C5D5C42FE5C424E5211900396E2600E5211A00396E10
:201C20002600E5CF66E4FC2712C3A5E8110080C416293FFCED52D23EEC210600D4162100BF
:201C40000039110400E5C42219D422110400B7ED525E2356234E2346E1CDC02C00C42FE52E
:201C6000C42FE5C42FE5C41AE5210800395E2356234E2346C5D5C431E5C424E5C428E521AB
:201C80001D00396E2600E5211E00396E2600E5CF1AE9FC2716C3A5E8110080C416293FFC5A
:201CA000ED52D2AAEC210600D416210000391104000E5C42219D422110400B7ED525E235641
:201CC000234E2346E1CDC02C00C42FE5C42FE5C42FE5C41AE5210800395E2356234E234632
:201CE000C5D5C431E5C424E5C428E5211D00396E2600E5211E00396E2600E5CF1AE9FC27FC
:201D000016C3A5E8110080C416293FFCED52D216ED210100D416C418CCCA2CEDC416EBC45A
:201D200018F33FFB293FFCED52ED62CCCA33EDC416D418C41ACC2BCCCA6FED210B00396E56
:201D40002600E5C431E5C431E5C431E5C4282323D4282B2BDDE400E5C42FE5C424E52118E2
:201D600000396E2600E5CF1CEEFB2710C3ABED210B00396E2600E5C431E5C431E5C431E5DF
:201D8000110400C42819D428110400B7ED525E2356234E2346C5D5C431E5C426E5211A00F3
:201DA000396E2600E5CF65E0FC2712C3A5E8C425E5C42DE5C433E5C433E5C4282323D4284E
:201DC0002B2BDDE400E5C408E5FDE1E1E511D3EDD5FDE9270AC3A5E8C3A5E8C319EE010A80
:201DE00000CDFF2625002BEAFB73004EEAFB640082EBFB750082EBFB66002CECFB67002C61
:201E0000ECFB650098ECFB580004EDFB780004EDFB6300AEEDFBC3D8EDC309E9DDE5DD2159
:201E20000000DD3927F91111000E40BB7ED52ED62CCCA3AEE210100C365EE110001E40BB769
:201E4000ED52ED62CCCA4EEE210200C365EE110010E40BB7ED52ED62CCCA62EE210300C3C7
:201E600065EE210400EBE407B7ED52F4FE21000039E5E40BE5CDD3222704DD6E132600EBBD
:201E80002E782600B7ED52C21AEF210000222168210000039E5CBD212702EB2A2168F33F06
:201EA000FB293FFCED52ED62CCCA1AEFED5B216821000039196E2600114180293FFCED5249
:201EC0003FED62CCCADEEEED5B216821000039196E2600114780293FFCED52ED62CCCAF8E2
:201EE000EEED5B216821000003919E56E2600260001E201600197DE1772A216823222168212D
:201F0000000039E5CBD212702EB2A2168F33FFB293FFCED52ED62CC2092DD5E07DD560817
:201F2000210000B7ED52C22EEF210000F4FE110080E4FE293FFCED52D257EFE411E5E40F9D
:201F4000E5E40DE5E409E5E407E52E2A2600E5CD7D22270CC3CCEFDD6E052600EB2E2D26C2
:201F600000000B7ED52C29AEFE411E5E40FE5E40DE5E409E521080039E5CFD2EFFB270AE411CE
:201F8000E5E40FE5E40DE5E409E5E4FEE52E202600E5CD7D22270CC3CCEFE411E5E40FE5ED
:201FA000E40DE5E409E5E4FEE5DD6E052600E5CF22E0FC270CE411E5E40FE5E40DE5E409E2
:201FC000E521080039E5CFD2EFFB270ADDF9DDE1ED4527FEC405D400210000395E23561A46
:201FE000B7283313722B73210900395E2356D5210F00395E2356D5210F00395E2356D55F14
:202000001600D51110F0D5211100397E23666FE9C1C1C1C118C2C71AE0FCC405D92702D9E6
:20202000ED4527FF210400396E2600EB2E302600B7ED52C23FE0210000393630C345E02147
:2020400000000393620C40EE5C40EE5C40EE5C40EE5C40EE5210A00396E2600E5CD7D2227EE
:202060000C2701ED45DDE5DD210000DD3927F1211A0039F4F3210300F4F1110080E4F12919
:2020800003FFCED523FED62CCCAB9E0E4F1CC2BCCC29EE0DD5EF1DD56F2E4F3197EB7CAA44D
:2020A000E0C3B9E0E4F12BF4F1110080E4F1293FFCED523FED62CC20D2DD5EF1DD56F2E475
:2020C000F3196E2600EB21100037ED52ED62CCCAE0E0E4F12923F4F1E4F123F4F1C3E6E0BD
:2020E000E4F12923F4F1DD5EF1DD56F2E407B7ED52F4FE21040039E5211C00395E23562303
:20210000 4E2346C5D5CD1F232706DD6E152600EB2E782600B7ED52C2ABE1210000F4F1218A
:2021200040039E5CBD212702EBE4F1F33FFB293FFCED52ED62CCCAABE1DD5EF1DD56F257
:2021400021040039196E2600114180293FFCED523FED62CCCA70E1DD5EF1DD56F221040014
:2021600039196E2600114780293FFCED52ED62CCCA8CE1DD5EF1DD56F22104003919E56E91
:20218000260026001E201600197DE177E4F123F4F121040039E5CBD212702EBE4F1F33FCB
:2021A000FB293FFCED52ED62CC208FDD5E07DD5608210000B7ED52C2BFE1210000F4FE119D
:2021C00000080E4FE293FFCED52D2E8E1E413E5E411E5E40FE5E409E5E407E52E2A2600E5CC
:2021E000CD7D22270CC35DE2DD6E052600EB2E2D2600B7ED52C22BE2E413E5E411E5E40FEE
:20220000E5E409E5210C0039E5CFD2EFFB270AE413E5E411E5E40FE5E409E5E4FEE52E208B
:202220002600E5CD7D22270CC35DE2E413E5E411E5E40FE5E409E5E4FEE5DD6E052600E570
:20224000CF22E0FC270CE413E5E411E5E40FE5E409E5210C0039E5CFD2EFFB270ADDF9DD64
:20226000E1ED45DDE5DD210000DD3927F6DD6E072600EB212000ECEB2E642600B7ED52CC63
:202280002BCCDD75F6CAE3E2E40DE5CD83292702E5CDA9252702EBE409B7ED52110080E50B
:2022A000E40D293FFCED52ED62CCCABAE2DD5E0DDD560E210080B7ED52CCCAC3E22101008C
:2022C000C3C6E2210000EBE1B7ED52F4FE21010039E5E40DE5CD83292702E5CDB925270 44B
:2022E000C300E3E40DE5CD8B252702EBE409B7ED52F4FE21010039E5E40DE5CD4225270487
```

```
:20230000DD5E09DD560A210000B7ED52C214E3210000F4FE110080E4FE293FFCED52D23D34
:20232000E3E413E5E411E5E40FE5E40BE5E409E52E2A2600E5CD7D22270CC360E4DD6E052D
:202340002600EB2E2D2600B7ED52C2B1E3110080E40D293FFCED52ED62CCCA61E3DD7EF600
:20236000B7CA7EE3E413E5E411E5E40FE5E40BE5210100E52E2D2600E5CD7D22270CE41316
:20238000E5E411E5E40FE5E40BE521090039E5CFD2EFFB270AE413E5E411E5E40FE5E40B51
:2023A000E5E4FEE52E202600E5CD7D22270CC360E4DD6E052600EB2E302600B7ED52CADCF1
:2023C000E3E413E5E411E5E40FE5E40BE5E4FEE5DD6E052600E5CF22E0FC270C110080E421
:2023E000D293FFCED52ED62CCCAF0E3DD7EF6B7CA01E4DD6EF72600EB2E2D2600B7ED52F4
:20240000CCCA1EE4E413E5E411E5E40FE5E40BE5210100E52E2D2600E5CD7D22270CDD6E6B
:202420002600EB2E302600B7ED52C249E4E413E5E411E5E40FE5E40BE5E4FEE5DD6E05A4
:202440002600E5CF22E0FC270CE413E5E411E5E40FE5E40BE521090039E5CFD2EFFB270A0B
:20246000DDF9DDE1ED45DDE5DD210000DD3927EFDD6E072600EB212000ECEB2E642600B7C0
:20248000ED52CC2BCCDD75EFCA3CE5211E00395E2356234E2346C5D5CFEFE6FC2704C5D5E6
:2024A000CF00E9FC2704EBE409B7ED52E5212000395E2356234E2346C5D5210000EB7A1728
:2024C000ED62444DCD061ECAE0E4212000395E2356234E2346C5D5110000010080CDC61E95
:2024E000CAE9E4210100C3ECE4210000EBE1B7ED52F4FE21010039E5212000395E23562307
:202500004E2346C5D5210000EB7A17ED62444DCD061ECA26E5212000395E2356234E2346FC
:20252000CD061BC331E5212000395E2356234E2346C5D5CFC9E8FC2706C36FE5211E0039D7
:202540005E2356234E2346C5D5CFE6E8FC2704EBE409B7ED52F4FE21010039E521200039F2
:202560005E2356234E2346C5D5CFACE8FC2706DD5E09DD560A210000B7ED52C283E52100A1
:2025800000F4FE110080E4FE293FFCED52D2ACE5E415E5E413E5E411E5E40BE5E409E52E68
:2025A0002A2600E5CD7D22270CC3E9E6DD6E052600EB2E2D2600B7ED52C22DE6211E003990
:2025C0005E2356234E2346C5D5210000EB7A17ED62444DCD061ECADDE5DD7EEFB7CAFAE50C
:2025E000E415E5E413E5E411E5E40BE5210100E52E2D2600E5CD7D22270CE415E5E413E5AD
:20260000E411E5E40BE521090039E5CFD2EFFB270AE415E5E413E5E411E5E40BE5E4FEE5D9
:202620002E202600E5CD7D22270CC3E9E6DD6E052600EB2E302600B7ED52CA58E6E415E54F
:20264000E413E5E411E5E40BE5E4FEE5DD6E052600E5CF22E0FC270C211E00395E2356235C
:202660004E2346C5D5210000EB7A17ED62444DCD061ECA79E6DD7EEFB7CA8AE6DD6EF026D6
:2026800000EB2E2D2600B7ED52CCCAA7E6E415E5E413E5E411E5E40BE5210100E52E2D26C5
:2026A00000E5CD7D22270CDD6E052600EB2E302600B7ED52C2D2E6E415E5E413E5E411E5AD
:2026C000E40BE5E4FEE5DD6E052600E5CF22E0FC270CE415E5E413E5E411E5E40BE5210972
:2026E0000039E5CFD2EFFB270ADDF9DDE1ED45210300395E2356234E2346C5D5210000EB86
:202700007A17ED62444DCD381ECA1AE7210300395E2356234E2346C328E7210300395E239C
:2027200056234E2346CD061BED4527FAC40DD400210F00397EB72845210900397E23B6239B
:20274000B64723B6CB7E2835CBBFB028302B2B2B7E2FB7C60177237E2FCE0077237E2FCE95
:20276000000077237E2FCE0077210D0039E5462366683E2D7723EBE1732372D51809210D004D
:2027800000397E23666FE5210E0039E521090039D10E041AB720070D28211B2B18F5D5E5C5F2
:2027A000CD102621150039E546236668C6307723EBE1732372C1D1E118D8210F00397E23BA
:2027C000666FD1E5AFED52E12804E52B18063E3077231814E5B7ED52E1280C380A461AEB94
:2027E0001270EB2B1318EDE13E0077C400D92706D9ED4527FC210A00D402210B00397EB700
:20280000CA1DE8210700395E2356234E2346C5D5210000EB7A17ED62444DCD061ECA4BE8D2
:2028200021070039E5210900395E2356234E2346CD032600C5D5210100EB010000CD902D16
:2028400000E1CDC02C00210B00D402210000D400110A80C400293FFCED52ED62CCCA9EE87A
:20286000C4002929EB21D725195E2356234E2346C5D5210B00395E2356234E2346CD0E1FC6
:20288000CA86E8C3A4E8C4022BD40223C40023D400110A80293FFCED52ED62CC20C2C4020B
:2028A00023D4022BC402D92704D9ED452E002600E5C409E5210700395E2356234E2346C55D
:2028C000D5CF2AE7FC2708ED452E012600E5C409E5210700395E2356234E2346C5D5CF2A55
:2028E000E7FC2708ED452E002600E5210500395E2356234E2346C5D5CFF3E7FC2706ED45AD
:202900002E012600E5210500395E2356234E2346C5D5CFF3E7FC2706ED4527BA210000D4F9
:2029200004C457CCCA2EE9C44FD414C333E9210600D41421000039E5215500395E235623FA
:202940004E2346C5D5CF72E1FD2706D416214B00396E2600EB212000ECD412210000395E01
:202960002356234E2346C5D5210000EB7A17ED62444DCD0C1ECA86E9210000395E23562369
:202980004E2346C394E9210000395E2356234E2346CD061BC5D5CF00E9FC2704D408C4121C
:2029A000EB2E672600B7ED52C2F7E9C414EB210000B7ED52C2BCE9210100D414C408EBCC0B
:2029C0006CED522B2B2BEBC416F33FFB293FFCED52ED62CCC2EFE9C408EBC416192BE5C403
:2029E00016EBE1F33FFB293FFCED523FED62CCCAF7E9216500D412C412C339EA110900C41B
:202A00001419E5C40AEBE1B7ED52D406C347EAC416EBCC6CED52E5C416EBE1B7ED52EBC4DA
```

```
:202A200008B7ED52E5C40AEB210800B7ED52EBE119D406C347EAC347EA010100CDFF2665DB
:202A400000FCE9FCC30FEA110080C406293FFCED523FED62CCCA65EA110880C406293FFCA1
:202A6000ED52ED62CCCAD6EA210000395E2356234E2346C5D5210000EB7A17ED62444DCD83
:202A80000C1ECAAFEA21000039E55E2356234E2346C5D5C40C2929EB214826195E23562370
:202AA0004E2346CD902D00E1CDC02C00C3D6EA21000039E55E2356234E2346C5D5C40C2935
:202AC00029EB214826195E2356234E2346CD4D2D00E1CDC02C002E012600E5211E0039E511
:202AE000210400395E2356234E2346C5D5CF2AE7FC2708211C00396E2600EB2E2D2600B7F5
:202B0000ED52CC2BCCCA10EB210100D41AC315EB210000D41A211C0039E5CDBD212702E5F8
:202B2000C41CEBE1B7ED52D418C416EBC41819D40A110080293FFCED523FED62CCCA63EBC9
:202B4000C40AEBC41A19E5C416EBE119110180E5C416293FFCED523FED62CCEBE119D4100A
:202B6000C36CEBC414EBC41A1923D410C41AEBC4141911060019D40EC418EBC416192BD4F5
:202B80000C110A80C40C293FFCED52ED62CCCA9FEB11F77FC40C293FFCED523FED62CCCA8E
:202BA000A7EBC40E2BD40E210000D408C412EB2E652600B7ED52C2BCEBC39CEEC410D40ECB
:202BC000C44DCCCAC0ECC410EBC44DF33FFB293FFCED52D2F3EBC45DE5C45DE5C45DE5C47C
:202BE00057E5C455E52E2A2600E5CD7D22270C2746ED45214900396E2600EB2E2D2600B7A0
:202C0000ED52CAC0EC214900396E2600EB2E302600B7ED52C27FECC41ACCCA4DECC451E58F
:202C2000C45BE5C461E5C461E5C41023D4102BEB21240039196E2600E5C408E5FDE1E1E526
:202C40001146ECD5FDE9270A210000D41AC44DEBC40EF33FFB293FFCED52D27CECC45DE558
:202C6000C45DE5C45DE5C457E5C416EBC455B7ED52E52E302600E5CD7D22270CC3C0EC1107
:202C80000180C40A293FFCED52D291ECC44D2BD44DC44DEBC40EF33FFB293FFCED52D2C066
:202CA000ECC45DE5C45DE5C45DE5C457E5C416EBC455B7ED52E52E202600E5CD7D22270C65
:202CC000C41ACCCAF1ECC451E5C45BE5C461E5C461E5C41023D4102BEB21240039196E2675
:202CE00000E5C408E5FDE1E1E511EFECD5FDE9270A110180C40A293FFCED52ED62CCCA11C9
:202D0000ED214900396E2600EB2E302600B7ED52CCCA37EDC451E5C45BE5C461E5C461E55E
:202D20002E302600E5C408E5FDE1E1E51132EDD5FDE9270AC33CED210100D404110180C47D
:202D40000A293FFCED52DAADEDC408EB211C0039197EB7CA84EDC451E5C45BE5C461E5C4D0
:202D600061E5C41023D4102BEB21240039196E2600E5C408E5FDE1E1E5117FEDD5FDE92758
:202D80000AC3A4EDC451E5C45BE5C461E5C461E52E302600E5C408E5FDE1E1E511A2EDD590
:202DA000FDE9270AC40A2BD40A23C33CED110180C414293FFCED52DADAEDC451E5C45BE56A
:202DC000C461E5C461E52E2E2600E5C408E5FDE1E1E511D8EDD5FDE9270A110080C40A29D9
:202DE0003FFCED52D226EEC451E5C45BE5C461E5C461E52E302600E5C408E5FDE1E1E51192
:202E000005EED5FDE9270AC4142BD41423C40A23D40A2B110180C414293FFCED52D223EEDB
:202E2000C326EEC3DAEDC4142BD414231101803FFFCED52DA95EEC408EB211C0039197ECD
:202E4000B7CA72EEC451E5C45BE5C461E5C461E5C41023D4102BEB21240039196E2600E57E
:202E6000C408E5FDE1E1E5116DEED5FDE9270AC392EEC451E5C45BE5C461E5C461E52E30F2
:202E80002600E5C408E5FDE1E1E51190EED5FDE9270AC326EEC410D40EC37426C44DCCCAC6
:202EA00053EFC40EEBC44DF33FFB293FFCED52D2CEEEC45DE5C45DE5C45DE5C457E5C45579
:202EC000E52E2A2600E5CD7D22270CC3EFEB214900396E2600EB2E2D2600B7ED52CA53EFC9
:202EE000214900396E2600EB2E302600B7ED52C253EFC44DEBC40EF33FFB293FFCED52D2C2
:202F000024EFC45DE5C45DE5C45DE5C457E5C416EBC455B7ED52E52E302600E5CD7D2227D7
:202F2000CC353EFC44DEBC40EF33FFB293FFCED52D253EFC45DE5C45DE5C45DE5C457E5BC
:202F4000C416EBC455B7ED52E52E202600E5CD7D22270CC41A23D406C4062BD406231101E1
:202F600080293FFCED52DA97EFC451E5C45BE5C461E5C461E5C41023D4102BEB212400394D
:202F80000196E2600E5C408E5FDE1E1E51192EFD5FDE9270AC358EF110180C414293FFCED07
:202FA00052DAC4EFC451E5C45BE5C461E5C461E52E2E2600E5C408E5FDE1E1E511C2EFD5CD
:202FC000FDE9270AC4142BD41423110180293FFCED52DA7026C408EB211C0039196E26004D
:202FE000EB210000B7ED52CCCA6826C451E5C45BE5C461E5C461E5C41023D4102BEB212463
:2030000000039196E2600E5C408E5FDE1E1E51114F0D5FDE9270AC71AE0FDC33DE0C451E5F7
:20302000C45BE5C461E5C461E52E302600E5C408E5FDE1E1E5113BE0D5FDE9270AC36C264D
:20304000C45DE5C45DE5C45DE5C457E5217C26E5CFD2EFFB270A110080C40C293FFCED52F6
:20306000DA83E0C451E5C45BE5C461E5C461E52E2B2600E5C408E5FDE1E1E51181E0D5FD04
:20308000E9270A211C0039E5C40EE5CDB9252704110A80C40C293FFCED52ED62CCCAAEE0AD
:2030A000110080C40C293FFCED523FED62CCCAC9E0211D0039E5211E00397EE177211C0058
:2030C000393630211E0039360011F77FC40C293FFCED523FED62CCCAE7E0110080C40C2934
:2030E0003FFCED52ED62CCCA02E1211E0039E5211F00397EE177211D00393630211F00398C
:20310000003600C45DE5C45DE5C45DE5C457E521240039E5CFD2EFFB270A214900396E260011
:20312000EB2E2D2600B7ED52CC2BCCCA31E1C44DCCCA6FE1C44DEBC40EF33FFB293FFCED4B
```

```
:2031400052D26FE1C45DE5C45DE5C45DE5C457E5C416EBC455B7ED52E5C41EEBE119E5C4C0
:203160000EEBE119E52E202600E5CD7D22270CC3782627E0210000D416D40E212300395E4F
:20318000235E234E2346C5D5110000010000CDAD2A00CAB2E121230039E5212500395E23CD
:2031A00056234E2346CD291AE1CDC02C00210100D416212300395E2356234E2346C5D51150
:2031C0000000010000CDA61ECAE6E1210000D40E210000D416210800391100000010000CD7D
:2031E000C02C00C33DE6212300395E2356234E2346CB11CB102110003970233600117F0055
:20320000C410B7ED52111C00B7ED52D410C410CF52EEFAC5D5ED5B7E26ED4B8026CFA2E843
:20322000FE2704CD4A1AD40E21180039E5212500395E2356234E2346E1CDC02C00211800F8
:20324000395E2356234E2346CBF9211B0039364B2B7121080039E5211A00395E2356234E2B
:203260002346CD4F1AE1CDC02C0021080039E55E2356234E2346C5D5210400EB010000CDA5
:20328000DC2600E1CDC02C00210400391100000010000CDC02C00110180C410293FFCED5260
:2032A000DA67E4C40ED414210000D40CC410EBC40CF33FFB293FFCED52ED62CCCA09E421DC
:2032C0000800395E2356234E2346C5D511CCCC01CC0CCDCB1ECA54E3C4142BD414232104F6
:2032E0000039E55E2356234E2346C5D5210A00EB010000CDF021E1CDC02C0021040039E593
:203300005E2356234E2346C5D5210E00395E2356234E2346C5D5210A00EB010000CDB326F2
:20332000C5D5114042010F00CDAB2DCD902D00E1CDC02C0021080039E55E2356234E23468F
:20334000C5D5210A00EB010000CDF021E1CDC02C00C3BFE221080039E55E2356234E2346E8
:20336000C5D5210100EB010000CDDC2600E1CDC02C0021040039E55E2356234E2346C5D5AE
:20338000210100EB010000CDDC2600E1CDC02C00210400395E2356234E2346C5D5118096E6
:2033A000019800CDCB1ECAF1E321080039E55E2356234E2346C5D5210100EB010000CD9023
:2033C0002D00E1CDC02C00C5D5210100EB010000CD4D2D0021040039E55E2356234E234643
:2033E000C5D5118096019800CD4D2D00E1CDC02C00C40C23D40CC410EBC40CF33FFB293F9B
:20340000FCED52ED62CCC2BFE2110180C414293FFCED52DA5AE4C4142BD414232108003595E
:20342000E55E2356234E2346C5D5210500EB010000CD902D00E1CDC02C0021080039E55E81
:203440002356234E2346C5D5210A00EB010000CDF021E1CDC02C00C309E4C414EBC40EB7F4
:20346000ED52D40EC3FDE5212300395E2356234E2346C410D414C40ED40C110080C40C2960
:203480003FFCED52ED62CCCAC9E5210800395E2356234E2346C5D511285C018F02CDCB1E95
:2034A000CAB0E4110080C414293FFCED52ED62CCCA33E5C41423D4142B21040039E55E23D3
:2034C00056234E2346C5D5210100EB010000CD822600E1CDC02C00210800395E2356234E5B
:2034E0002346C5D5210100EB010000CDF41D6069ECCCCA12E521040039E55E2356234E23ED
:2035000046C5D511404B014C00CD902D00E1CDC02C0021080039E55E2356234E2346C5D52C
:20352000210100EB010000CD822600E1CDC02C00C38AE421080039E55E2356234E2346C580
:20354000D5210A00EB010000CDAB2DE1CDC02C0021040039E55E2356234E2346C5D5210A87
:2035600000EB010000CDAB2DE1CDC02C0021080039E55E2356234E2346C5D5210A00395ECC
:203580002356234E2346C5D5118096019800CDF021CD902D00E1CDC02C0021040039E55EDB
:2035A0002356234E2346C5D5118096019800CDB326E1CDC02C00C40C23D40C110080293F52
:2035C000FCED52ED62CCC28AE4110080C414293FFCED52D2FDE5C41423D4142B2108003935
:2035E000E55E2356234E2346C5D5210100EB010000CD822600E1CDC02C00C3C9E5110000FC
:20360000010080C5D5210C00395E2356234E2346CDF41D6069ECCCCA3DE621080039E55E87
:203620002356234E2346C5D5210A00EB010000CDF021E1CDC02C00C40E23D40E2BC427EB36
:203640000210000B7ED52CA7EE6C416CCCA68E6C427E5210A00395E2356234E2346CD061B94
:2036600E1CDC02C00C37BE6C427E5210A00395E2356234E2346E1CDC02C00C387E6C427F2
:203680005E2356234E2346C40ED92720D9ED45DDE5DD210000DD3927FD210300DDE400118C
:2036A000290019DDE400110E0019F4FECFD8E6FDCC2BCCCABCE6CD9F1EC3ACE6E4FE7EDD08
:2036C00077FDE4FE3600E4FE2B36FFDD6EFD26002600DDF9DDE1ED45210300DDE4001129A3
:2036E0000000019DDE400110D00196E2600CC2BCCED45D9210000CDD529EFD9210000CDDF29AD
:20370000ED45D9210000CDD529EFC403236E2600D9210000CDDF29ED45D9210000CDD5297F
:20372000EFC4036E2600D9210000CDDF29ED45D9210000CDD529EF2ABB74E52141E7ED54C2
:20374000E9221F68EFED5B1F6821FFFFB7ED52CA4AE8EFED5B1F682EFF2600B7ED52CC2B0A
:20376000CCCA40E8EF111400010000C5D5CFFEE2FA2704EF2ABB74E5217EE7ED54E97D327C
:203780001E68CCCA36E8EF2A1E682600EB010000C5D5110200010000CDAB2DED531A68ED3C
:2037A000431C68EF2ABD74E5ED5B1A68ED4B1C68C5D52A1E682600E5C40BE5C408E5FDE1F5
:2037C000E1E511C8E7D5FDE9270AEB2A1E682600B7ED52CC2BCCCA2CE8EF2A1E6826002B2F
:2037E000EBC403196E2600EB2EFE2600B7ED52CC2BCCCA22E8EF2A1E6826002BEBC40319E5
:20380000EB26606AAFED6CFCEB3803CDE828003600EF2A1E6826002B2BD9210000CDDF29A6
:20382000ED45EF210000C319E8C333E8EF210000C319E8C33DE8EF210000C319E8C347E822
:20384000EF210000C319E8C351E8EF210000C319E8EFC319E8D9210000CDD529EF2ABF7400
```

```
:20386000E52EFF2600E5C402E5FDE1E1E51173E8D5FDE92704EF2ABF74E511050021090019
:20388000396E260019E5C402E5FDE1E1E51193E8D5FDE92704EF2ABF74E5210700396E2676
:2038A00000E5C402E5FDE1E1E511AFE8D5FDE92704EF2ABF74E52AB6742600E5C402E5FD0E
:2038C000E1E1E511C9E8D5FDE92704EF2ABF74E5210500396E2600E5C402E5FDE1E1E51130
:2038E000E5E8D5FDE92704EF210300396E2600EB2AB67426007DAB6F7CAA67EB2105003962
:203900006E26007DAB6F7CAA677D321868EF210700396E2600221668EF00EF2A16682B2269
:20392000166823CCCA60E9EF2ABF74E5C40B6E2600E5C402E5FDE1E1E5113FE9D5FDE92724
:2039400004EFC40923D4092B6E2600E52A18682600EBE17DAB6F7CAA677D321868C31AE94E
:20396000EF2ABF74E52A18682600E5C402E5FDE1E1E51178E9D5FDE92704EF2ABF74E52E5B
:20398000FE2600E5C402E5FDE1E1E51191E9D5FDE92704EFD9210000CDDF29ED45D9210074
:2039A00000CDD529EF110400010000C5D5CFFEE2FA2704EFC40323236E2600C3EDEDEF00AD
:2039C000EF2AFCC02600CC2BCCCAD2E9EF3E0132F9C0EF2AB974E5210100E5C402E5FDE1D0
:2039E000E1E511E8E9D5FDE92704EF110200010000C5D5CFFEE2FA2704EF21E6C1E52E09F5
:203A00002600E5C407236E2600E52E642600E5CF55E8FD2708EF00EF2AC174E52122EAED23
:203A2000054E9EB2AB774B7ED52CA30EAEFC317EAEF110200010000C5D5CFFEE2FA2704EF1C
:203A40002AB974E5210000E5C402E5FDE1E1E51155EAD5FDE92704EFC32FEEEF00EF2AFCCC
:203A6000C02600CC2BCCCA6FEAEF3E0132FAC0EF2AB974E5210100E5C402E5FDE1E1E511CE
:203A800085EAD5FDE92704EF110200010000C5D5CFFEE2FA2704EF21E6C1E52E092600E582
:203AA000C407236E2600E52E662600E5CF55E8FD2708EF00EF2AC174E521BFEAED54E9EBC7
:203AC0002AB774B7ED52CACDEAEFC3B4EAEF110200010000C5D5CFFEE2FA2704EF2AB97413
:203AE000E5210000E5C402E5FDE1E1E511F2EAD5FDE92704EFC32FEEEF00EF2AB974E521AF
:203B00000100E5C402E5FDE1E1E51110EBD5FDE92704EF110200010000C5D5CFFEE2FA2711
:203B200004EF21D1C1E5C405232323D1D5010C00EDB0E1EF210000E52E002600E5C407237B
:203B40006E2600E52E6C2600E5CF55E8FD2708EF00EF2AC174E5215CEBED54E9EB2AB7741B
:203B6000B7ED52CA6AEBEFC351EBEF110200010000C5D5CFFEE2FA2704EF2AB974E5210085
:203B800000E5C402E5FDE1E1E5118FEBD5FDE92704EF3E0032FDC0EFC32FEEEF00EF2AB9D4
:203BA00074E5210100E5C402E5FDE1E1E511B3EBD5FDE92704EF110200010000C5D5CFFE57
:203BC000E2FA2704EF210000E52E002600E5C407236E2600E52E702600E5CF55E8FD270868
:203BE000EF00EF2AC174E521EDEBED54E9EB2AB774B7ED52CAFBEBEFC3E2EBEF1102000118
:203C00000000C5D5CFFEE2FA2704EF2AB974E5210000E5C402E5FDE1E1E51120ECD5FDE9DE
:203C20002704EFC32FEEEF00EF3AFCC0B7CA37ECEF212F7522ECC1EF2AB974E5210100E55D
:203C4000C402E5FDE1E1E5114DECD5FDE92704EF110200010000C5D5CFFEE2FA2704EF2164
:203C6000E6C1E52E092600E5C407236E2600E52E722600E5CF55E8FD2708EF00EF2AC174EF
:203C8000E52187ECED54E9EB2AB774B7ED52CA95ECEFC37CECEF110200010000C5D5CFFE7C
:203CA000E2FA2704EF2AB974E5210000E5C402E5FDE1E1E511BAECD5FDE92704EF3E003281
:203CC000FCC0EF3E0032FBC0EF11B8FE019543ED530475ED430675EFC32FEEEF00EF3E012F
:203CE00032F8C0EF2AB974E5210100E5C402E5FDE1E1E511F9ECD5FDE92704EF110200017A
:203D000000000C5D5CFFEE2FA2704EF210000E52E002600E5C407236E2600E52E742600E5F3
:203D2000CF55E8FD2708EF00EF2AC174E52133EDED54E9EB2AB774B7ED52CA41EDEFC328B6
:203D4000EDEF110200010000C5D5CFFEE2FA2704EF2AB974E5210000E5C402E5FDE1E1E585
:203D60001166EDD5FDE92704EFC32FEEEF00EF3E0132EFC1EF21E6C1E5C405232323D1D5B7
:203D8000010900EDB0E1EFC32FEEEF00EF3E0132EFC1EF21E6C1E5C405232323D1D501094F
:203DA0000EDB0E1EFC32FEEEF00EF3E0132EFC1EFC32FEEEF00EF3E0132EFC1EFC32FEE1A
:203DC000EF00EF3E0132EFC1EF21E6C1E5C405232323D1D5010900EDB0E1EFC32FEEEF002A
:203DE000EF3E0132EFC1EFC32FEEC32FEE010C00CDFF264400BEE9FD46005BEAFD4C00F851
:203E0000EAFD50009BEBFD520026ECFD5400DBECFD64006CEDFD66008AEDFD6C00A8EDFDDD
:203E20007000B4EDFD7200C0EDFD7400DEEDFDEFD9210000CDDF29ED45D9210000CDD52967
:203E4000EF3E00321568EFC40323D4032BEF00EFC4032BD40323CCCA79EEEFC40523D40530
:203E60002B6E2600E52A15682600EBE17DAB6F7CAA677D321568C34FEEEFC4052BD405EB0E
:203E800026606AAFED6CFCEB3803CDE828003600EF3A1568B7CAA5EEEF210000D921000031
:203EA000CDDF29ED45EF210100C39CEEEFC39CEEC403220D68210000220F68221168210687
:203EC0006AE5CDFF282702CCCAB6EF213F68CD9C2D00ED530968ED430B68C405EB2A116832
:203EE000F33FFB293FFCED52ED62CCCAF4EE2A0F68CC2BCCCAADEFED5B1168C405B7ED52E1
:203F0000E5ED5B11682A0D6819E521066AE5CD0C29270622136811018 0293FFCED523FEDBB
:203F200062CCCA6FEF3AC7C3B7CA45EF21066AE5CD081D2702EB2A7C69F33FFB293FFCEDA9
:203F4000523FED62CCCA52EF2ABDC3E52152EFED54E9213F68CD9C2D00ED530968ED430B45
:203F600068ED5B13682A116819221168C3AAEF2A1168CCCAA7EF213F68CD9C2D00C5D5EDAF
```

```
:203F80005B0968ED4B0B68CD4D2D00C5D5210B00395E2356234E2346CDDE1ECAA4EF21016B
:203FA00000220F68C3AAEFC3ADEFC3DAEE21066AE5CD5C2927022A1168ED45D9210000CD95
:203FC000D529EFC407EB210900B7ED52C2ECEFEF115E002A612919EB7A17ED62444DED53BA
:203FE000CBC1ED43CDC1EF3E1F320868EFC407EB210A00B7ED52C26329EF11BC002A612905
:2040000019EB7A17ED62444DED53CBC1ED43CDC1C714E0FEEF3E3F320868EFC407EB210B09
:204020000B7ED52C244E0EF117012A612919EB7A17ED62444DED53CBC1ED43CDC1EF3E4C
:204040005F320868EFC407EB210C00B7ED52C26EE0EF11EE022A612919EB7A17ED62444D6E
:20406000ED53CBC1ED43CDC1EF3E7F320868EFCF5CE3FEEFCFA2E5FEEF2ECC2600E5CF3B2C
:20408000E4FE2702EFCFA2E5FEEF2E4E2600E5CF3BE4FE2702EFCFA2E5FEEF210300396E4A
:2040A0002600E5CF3BE4FE2702EFCFA2E5FEEF210500396E2600E5CF3BE4FE2702EFCFA261
:2040C000E5FEEF2A08682600E5CF3BE4FE2702EFCFA2E5FEEFD9210000CDDF29ED45D92127
:2040E0000000CDD529EFC405EB210800CD252A00EBC40319220668EF2A0668EB010000C57A
:20410000D511FFFF010000CDA61EC21AE1ED5B0668215005B7ED52CC2BCCCA2DE1EF11B8F7
:20412000FE018143D9210000CDDF29ED45EF1100082A0668B7ED52ED62CCCA56E1EF2A06EA
:2041400068CF75EEFAC5D5110000018041CFA2E8FE2704C324E1EF1100F82A0668B7ED528E
:20416000CF75EEFACD291AC5D5110000018041CFA2E8FE2704C324E1EFC324E1D92100009B
:20418000CDD529EFCF5CE3FE220268EFCFA2E5FEEF2ECC2600E5CF3BE4FE2702EFCFA2E53C
:2041A000FEEF2EBE2600E5CF3BE4FE2702EF210000220468EF1109802A0468293FFCED52A6
:2041C000ED62CCCAFCE1C3D4E1EF2A046823220468C3B4E1EFCFA2E5FEEFED5B046821F61A
:2041E000FF19EB3003CDC82C0029EB21B3C119E5CFA3E4FEFDE1FDF400C3C9E1EF2A02680E
:20420000D9210000CDDF29ED45D9210000CDD529EFCF5CE3FEEFCFA2E5FEEF2E332600E53F
:20422000CF3BE4FE2702EF210000220068EF1109802A0068293FFCED52ED62CCCA75E2C312
:204240004DE2EF2A006823220068C32DE2EFCFA2E5FEEFED5B006821F6FF19EB3003CDC86B
:204260002C0029EB21B3C119E5CFA3E4FEFDE1FDF400C342E2EFD9210000CDDF29ED45D998
:20428000210000CDD529EFCFA2E5FEEFCF5CE3FEEFCFA2E5FEEF2ECC2600E5CF3BE4FE27AA
:2042A00002EFCFA2E5FEEF2E442600E5CF3BE4FE2702EFCFA2E5FEEF210100E5CFCCE2FE84
:2042C0002702EFD9210000CDDF29ED45D9210000CDD529EFC403CCCAE6E2EF2E012600E5C3
:2042E000CF05E3FE2702EF210500E5C405E52108C1E5216000E5CD281F2708EFD9210000D7
:20430000CDDF29ED45210300396E2600EB210100B7ED52CC2BCCC22AE3210300396E26001F
:20432000EB210100B7ED52CC2BCCCA45E3210600E5210000E52106C1E5216700E5CD281F65
:204340002708C35AE3210600E5210100E52106C1E5216700E5CD281F2708ED45D921000072
:20436000CDD529EF2E012600E5CF05E3FE2702EF210600E5210000E52108C1E5216000E535
:20438000CD281F2708EF210000E5CFCCE2FE2702EF2E012600E5CF05E3FE2702EF11020038
:2043A000010000C5D5CFFEE2FA2704EF2E002600E5CF05E3FE2702EF110200010000C5D5EB
:2043C000CFFEE2FA2704EF2E012600E5CF05E3FE2702EF213F68CD9C2D00C5D5210200EB0D
:2043E000010000CD902D00ED53FA67ED43FC67EF21000022FE67EF00EFED5BFA67ED4BFCAC
:2044000067C5D5213F68CD9C2D00CDCB1ECA2EE4EF210600E5216000E5CD151B2704CC2B2B
:20442000CCCA2BE4EF21010022FE67C3F8E3EF2AFE67D9210000CDDF29ED45D9210000CD5B
:20444000D529EF21000022F867EF1108802AF867293FFCED52ED62CCCA99E4C369E4EF2A8E
:204460000F8672322F867C349E4EF210300396E2600EB210100DC2600E5CF26E5FE2702EF85
:2044800021030039E5210500396E2600EB210100CD1B197DE177C35EE4EFD9210000CDDF6A
:2044A00029ED452A06C12600EB2EBF2600DC7D32D0C12A06C12600EB2E402600EC7D32CF70
:2044C000C1CFA2E5FECF6AE5FE7D32F56721000022F66711078 02AF667293FFCED52ED62EF
:2044E000CCCA1DE5CFA2E5FE2AF5672600EB210100CD1B197D32F567CF6AE5FEEB2AF5677E
:2045000026002600197D32F5672AF66722F66711078 0293FFCED52ED62CC20C72AF5673F
:204520002600 2600ED452E002600E5CF05E3FE2702210300397EB7CA45E52E012600E5CF57
:204540005E3FE2702CFC4E5FECFC4E5FECFC4E5FECFC4E5FECFC4E5FE2E012633
:204560000 00E5CF05E3FE2702ED45ED5E3ACFC1D3326700CF02E6FE3AD0C1D3326700CF0208
:20458000E6FECF02E6FED33A6000E64032F467ED5D2AF4672600EB210100CD252A0026001E
:2045A000ED45ED5ECFC4E5FECFC4E5FECFC4E5FECFC4E5FECFC4E5FECFC4E5FECFC4E5FE44
:2045C000ED5DED45ED5ED33ABF00D33ABF00D33ABF00D33ABF00D33ABF00D33ABF00D33A3F
:2045E000BF00D33ABF00D33ABF00D33ABF00D33ABF00D33ABF00D33ABF00D33ABF00ED5D1E
:20460000ED45ED5ED33ABF00D33ABF00D33ABF00D33ABF00D33ABF00D33ABF00ED5DED45D9
:20462000D9210000CDD529EF21000022B1C1EFCFBAE6FEEF210900E521FEC3E521B100E539
:20464000CDCC212706EF210000E5210000E521B300E5CDCC212706EF210000E5210000E5DD
:20466000021B200E5CDCC212706EF210300E521FFC3E521B000E5CDCC212706EFD921000055
:20468000CDDF29ED45D33ABF004FD32ABE00E6F8FEF8C2A9E6D33ABF00E6F8FEF8CAA9E61F
```

```
:2046A000D33ABF004FD32ABE00B7CB15CB15CB15656922F2672AF267ED45D9210000CDD533
:2046C00029ED5F672EB0FD7D216729FD3600C3FDF401EFD9210000CDDF29ED45CF85E6FEE5
:2046E000CF75EEFAC5D5113F3501DE3FCFC8E7FE2704C5D52AB1C1CF75EEFAC5D511DD3888
:2047000001DE44CFC8E7FE2704CFD1EEFA2704CD4F1AED4521000022B1C1ED45217E69E5E0
:20472000CD98292702ED45217E69E5CDBD292702CCCA59E7C403E5217E69E5CD9E1D2704A5
:2047400022F0672AF067CCCA4DE7CD671B217E69E5CDB8292702C35FE721000022F0672AB5
:20476000F067ED4521066AE5CDFF282702CCCAB6E721066AE5CDCA1D270222EE673AC7C35C
:20478000B7CA9DE721066AE5CD081D2702EB2A7C69F33FFB293FFCED523FED62CCCAAAE704
:2047A0002ABDC3E521AAE7ED54E921066AE5CD5C292702C3BCE721FFFF22EE672AEE67ED35
:2047C00045D9210000CDD52960697C2937CB1DD9C403EBC40576AC2937CB1D7CB72876456E
:2047E0004AD67F3806D98438731804D9843066767F656AE378B7285DD9ED49FD210000FD40
:2048000009F7FD19EBFD19D9E31600F719D9ED59444D1600F7195855D96568AF19CE00EBF5
:20482000E319CE00EBFD7C856F30012408F231E8370600CB18CB7C2005F3ED6A18033C3889
:204840001B087BB72802CBC2085A554C1F3802CBB9B047ED45060048505818F708E67F478A
:20486000E8011000018ECEFD9210000CDDF29ED45D9210000CDD5297F7B7874716E6B6848
:204880006663615E5C5A5856555351504E4D4B4A484746454443414001800FF110000CB181D
:2048A000ED456069297C087CB728ED37CB1D7D656AD91F1FE61F0178E8CC6F0946500E0038
:2048C00059F729E37DD9444DED49F719EBE3ED5229EB424BF729E3D9ED49F719EBE3ED5272
:2048E00029EB424BF7CB11CB10ED6AD5E36069D9ED49D9EBF719D9ED49F719D9CB7A280148
:20490000009E3EB470E00CB78F7280119D9EB09D213E91376EB19D9300123D9EBCC6CED525F
:20492000D9EBE1ED52E3D929F329F37DB72802CBC408CB18D67FED44C67ECB101F474A531F
:204940005C3802CBB9C7C8E7FEEFD9210000CDDF29ED4527EC210300D404210300D40621AB
:20496000200D408210200D40A210200D40C210C00D400110000010000ED53AE67ED43B00D
:2049800067110000010000ED53AA67ED43AC67210000D402210000D40E110580C40E293F40
:2049A000FCED52ED62CCCAF6E9C40E29EB2104003919DDE400E5C41029EB21622E19DDE482
:2049C00000EB010000D9D1CCFCE5D5D9CDAB2DC5D5ED5BAE67ED4BB067CD902DED53AE671C
:2049E000ED43B067C40E23D40E110580293FFCED52ED62CC20B321100039E5ED5BAE67EDD9
:204A00004BB067C5D5CFA0E2FF2704E1CDC02C21100039E55E2356234E2346C5D5ED5BAEF5
:204A200067ED4BB067C5D5210100EB010000CD4D2DCD902DE1CDC02C211000395E23562349
:204A40004E2346C5D5ED5BAE67ED4BB067CD4D2DC5D5210100EB010000CD902DED53B66783
:204A6000ED43B867211000395E2356234E2346C5D521FF0FEB7A17ED62444DCDF41DC5D52F
:204A800021FF0FEB7A17ED62444DCDC61ECA39EB211000395E2356234E2346C5D521010015
:204AA000EB7A17ED62444DCD902DC5D521FF0FEB7A17ED62444DCDF41DC5D5CFA0E2FF27FC
:204AC00004ED53B267ED43B467211000395E2356234E2346C5D5210100EB7A17ED62444DFB
:204AE000CD902DC5D521FF0FEB7A17ED62444DCDF41DED53AA67ED43AC6721100039E55EE8
:204B00002356234E2346C5D5210010EB7A17ED62444DCD4D2DE1CDC02C211000039E55E236A
:204B200056234E2346C5D521FF0FEB7A17ED62444DCDEA2E00E1CDC02CC400CCCA71EC21C9
:204B4000400D40E110080C40E293FFCED523FED62CCCA22ECC40E29EB2104003919DDE419
:204B600000CCCA90EB211000395E2356234E2346C5D511FF0F010000CDF41DC40EC5D529DC
:204B8000EB21622E19DDE4002BEB010000CD381ECA0EECC40E29EB2104003919E5DDE4009E
:204BA0002BFDE1FDF40023C4002BD40023C40223D4022B2929EB21BA6719E5C410EB7A173B
:204BC000ED62444DC5D5211800EB7A17ED62444DCDDC26C5D5211600395E2356234E23463C
:204BE000CD902DE1CDC02C211000039E55E2356234E2346C5D5C41429EB21622E19DDE40080
:204C0000EB010000CD4D2DE1CDC02CC355EBC40E2BD40E110080293FFCED523FED62CCC295
:204C200055EB110080C40E293FFCED52D26EEC211000039E55E2356234E2346C5D521001037
:204C4000EB7A17ED62444DCD4D2DE1CDC02C211000039E55E2356234E2346C5D521FF0FEB63
:204C60007A17ED62444DCDEA2E00E1CDC02CC339EB2714ED4527FEC405EBC407AF435A57A9
:204C8000292929291955586C67D407EBD4052101000D400110C80C400293FFCED52ED62CC23
:204CA000CA49EDC4002929EB21BA67195E2356234E2346C5D511FFFF010F00CDF41DC5D5B6
:204CC000210900395E2356234E2346CD061ECAFDECC4002B2929EB21BA67195E2356234E4D
:204CE0002346C5D511FFFF010F00CDF41DC5D5210900395E2356234E2346CD381ECA36EDF6
:204D0000C4002B2929EB21BA67195E2356234E2346C5D5211800EB7A17ED62444DCD872EAA
:204D200000EBEB217F00DC29EB21622E19DDE400D92702D9ED45C40023D400110C80293FB5
:204D4000FCED52ED62CCC2A3ECC4002B2929EB21BA67195E2356234E2346C5D511FFFF01CA
:204D6000F00CDF41DC5D5210900395E2356234E2346CD381ECAABEDC4002B2929EB21BA0C
:204D800067195E2356234E2346C5D5211800EB7A17ED62444DCD872E00EBEB217F00DC29B6
:204DA000EB21622E19DDE400C330ED210000C330ED27FC210000D402110580C402293FFCC2
```

```
:204DC000ED52ED62CCCAF8EDC40229EB21622E19DDE400EBC40737ED52ED62CCCAE6EDC4BD
:204DE00002D407C3F8EDC40223D402110580293FFCED52ED62CC20D0C402EB210500B7EDB0
:204E000052C214EE210000EB7A17ED62444DD92704D9ED4521BA6722A267210B00D4021170
:204E20000080C402293FFCED523FED62CCCA8FEEC40229291104D0192BD400C400EB2AA228
:204E400067196E2600EB218000DCCC2BCCCA7CEEC400EB2AA267196E2600EBC40737ED5224
:204E6000ED62CCCA7CEEC400EB2AA26719E56E2600EB218000EC7DE177C38FEEC4022BD41D
:204E8000021100080293FFCED523FED62CC20A1110080C402293FFCED52D2A9EE210000EB52
:204EA0007A17ED62444DC30EEEC4022929EB21BA67195E2356234E2346C5D511FFFF010FFA
:204EC0000CDF41DED53A467ED43A667ED4BA667ED5BA46769292929297DCC6AFCFCFCFC24
:204EE000B5D60D4F7AE60FF6D057ED43A667ED53A467ED5BA467ED4BA667C30EEE27FCC479
:204F000007EBC409AF435A57292929291955586C67D409EBD40721BA6722A067210B00D4E4
:204F200002110080C402293FFCED523FED62CCCA9AEFC4022929EB21BA67195E2356234E22
:204F40002346C5D511FFFF010F00CDF41DC5D5210B00395E2356234E2346CDA61ECA87EFD0
:204F6000C4022929110400192BD400C400EB2AA06719E56E2600EB217F00DC7DE17721011C
:204F800000D92704D9ED45C4022BD402110080293FFCED523FED62CC2098210000C381EFA1
:204FA000D9210000CDD529EFED5B5867ED4B5A67C5D5ED5B6067ED4B6267CD4D2DC5D5EDC5
:204FC0005B5C67ED4B5E67CD5B2DCD4D2DD9210000CDDF29ED4527FE210100D400110500E8
:204FE000C400B7ED52ED62CCCAE62EC4002B292929EB21B62E195E2356234E2346C5D5C47C
:2050000042B292929EB21B62E19110400195E2356234E2346CD4D2DC400C5D5292929EBF3
:2050200021B62E195E2356234E2346CDFE1ECADE2EC735E0FFE5210200392323DDE400E5DA
:2050400021F900E5CD051A2704E121F900E5CD79052702C40023D400110500B7ED52ED62D0
:20506000CCC2E22E210000D400C400292929EB21B62E195E2356234E2346C5D511FFFF01FA
:205080000900CDFE1ECAEFE0C4002929E529D119EB2158671911080019E5C4022929E52956
:2050A000D119EB2158671911FFFF010900CDC02CE1CDC02CC4002929E529D119EB215867DD
:2050C0001911040019E5C402292929EB21B62E195E2356234E2346C5D511FFFF010900CD29
:2050E0005B2DCD4D2DE1CDC02CC40023D4002B110500C400B7ED52ED62CCCA39E2C40029A4
:205100002929EB21B62E195E2356234E2346C5D5C404292929EB21B62E19110400195E23EE
:2051200056234E2346CD4D2DC5D5210100EB010000CD902DC5D5110000010800CD0E1FCA4E
:205140045E1C339E2C4002929E529D119EB2158671911080019E5C4022929E529D119EB47
:2051600021586719E5C404292929EB21B62E195E2356234E2346C5D5C408292929EB21B6B1
:205180002E19110400195E2356234E2346CD4D2DE1CDC02CE1CDC02CC40023110500B7EDCD
:2051A00052D2E8E1C4002929E529D119EB2158671911040019E5C4022929E529D119EB21E1
:2051C0005867195E2356234E2346C5D5C406232929EB21B62E195E2356234E2346CD4D70
:2051E0002DE1CDC02CC328E2C4002929E529D119EB2158671911040019E5C4022929E529F0
:20520000D119EB2158671915E2356234E2346C5D5110000010800CD4D2DC5D5110100010067
:2052200000CD902DE1CDC02CC40023D400110500B7ED52ED62CCC2FDE0110600C400B7ED4A
:2052400052ED62CCCA9CE2C4002929E529D119EB21586719E5C4022929E529D119EB21584E
:20526000671911080019E5C4042929E529D119EB2158671911040019E5210000EB01000081
:20528000E1CDC02CE1CDC02CE1CDC02CC40023D400110600B7ED52ED62CC20AB2702ED4537
:2052A00027FE210500395E2356234E2346C5D511FFFF01FFFFCDC61ECAE9E221050039E587
:2052C000210700395E2356234E2346C5D5210100EB7A17ED62444DCD902DC5D511FEFF0171
:2052E000FFFFCDF41DE1CDC02C210400D400110080C400293FFCED523FED62CCCAC7E3C4B5
:2053000002929E529D119EB2158671911040195E2356234E2346C5D5C4042929E529D1ED
:2053200019EB2158671915E2356234E2346C5D5C4082929E529D119EB2158671911080019F9
:205340005E2356234E2346CD4D2DCD4D2DC5D5210900395E2356234E2346CDDE1ECA80E36A
:20536000C4002929E529D119EB2158671915E2356234E2346C5D5210000EB010000CDC61E32
:20538000CAB3E3C4002929E529D119EB2158671911080019E55E2356234E2346C5D5210B2D
:2053A000000395E2356234E2346CD4D2DE1CDC02CC3C7E3C4002BD400110080293FFCED52BE
:2053C0003FED62CCC2FFE2C400EB21FFFFB7ED52C2F1E3E5210200392323DDE400E521F533
:2053E00000E5CD051A2704E121F500E5CD79052702C4002929E529D119EB21586719110856
:20540000000195E2356234E2346C5D5210100EB010000CD902DD92702D9ED4527F4210000 47
:2054200039110000010000CDC02C210400D40A110080C40A293FFCED523FED62CCCAE1E47A
:2054400021040039E5C40C2929E529D119EB2158671911040195E2356234E2346C5D5C4CE
:2054600010292E529D119EB2158671915E2356234E2346C5D5C4142929E529D119EB21581D
:20548000671910800195E2356234E2346CD4D2DCD4D2DE1CDC02C210400395E2356234EDB
:2054A0002346C5D5210400395E2356234E2346CD0C1ECACDE4C40AD40821000039E5210658
:2054C00000000395E2356234E2346E1CDC02CC40A2BD40A110080293FFCED523FED62CCC240E1
```

```
:2054E000E421000039E55E2356234E2346C5D511FEFF01FFFFCDF41DE1CDC02CC40FCCCA50
:205500001CE5210000395E2356234E2346C5D5210000EB7A17ED62444DCD0C1ECA77E5C487
:20552000082929E529D119EB2158671911080019E55E2356234E2346C5D5210600395E23F2
:2055400056234E2346CD4D2DE1CDC02CC40FE5C40A2929E529D119EB215867191108001954
:205560005E2356234E2346C5D5210100EB010000CD902DE1CDC02C210000395E2356234E0C
:205580002346D9270CD9ED4527FE21090039E5210B00395E2356234E2346C5D5210100EB61
:2055A0007A17ED62444DCD902DC5D511FEFF01FFFFCDF41DE1CDC02C21050039E55E2356B6
:2055C000234E2346C5D5210100EB7A17ED62444DCD4D2DE1CDC02C210400D400110080C4AA
:2055E00000293FFCED523FED62CCCA5CE6C4002929E529D119EB21586719110800195E23FD
:2056000056234E2346C5D5210900395E2356234E2346CDA61ECA49E6C4002929E529D11914
:20562000EB2158671911080019E55E2356234E2346C5D5210F00395E2356234E2346CD90AD
:205640002DE1CDC02C2702ED45C4002BD400110080293FFCED523FED62CC209121F500E52B
:20566000CD051A270221F500E5CD79052702C345E6000000000000000000000000000000B8
:2056800000000000000000000000000000000000000000000000000000000000000000000A
:2056A0000000000000000000000000000000000000000000000000000000000000000000EA
:2056C0000000000000000000000000000000000000000000000000000000000000000000CA
:2056E0000000000000000000000000000000000000000000000000000000000000000000AA
:20570000000000000000000000000000000000000000000000000000000000000000000089
:20572000000000000000000000000000000000000000000000000000000000000000000069
:20574000000000000000000000000000000000000000000000000000000000000000000049
:20576000000000000000000000000000000000000000000000000000000000000000000029
:20578000000000000000000000000000000000000000000000000000000000000000000009
:2057A0000000000000000000000000000000000000000000000000000000000000000000E9
:2057C0000000000000000000000000000000000000000000000000000000000000000000C9
:2057E0000000000000000000000000000000000000000000000000000000000000000000A9
:20580000000000000000000000000000000000000000000000000000000000000000000088
:20582000000000000000000000000000000000000000000000000000000000000000000068
:20584000000000000000000000000000000000000000000000000000000000000000000048
:20586000000000000000000000000000000000000000000000000000000000000000000028
:20588000000000000000000000000000000000000000000000000000000000000000000008
:2058A0000000000000000000000000000000000000000000000000000000000000000000E8
:2058C0000000000000000000000000000000000000000000000000000000000000000000C8
:2058E0000000000000000000000000000000000000000000000000000000000000000000A8
:20590000000000000000000000000000000000000000000000000000000000000000000087
:20592000000000000000000000000000000000000000000000000000000000000000000067
:20594000000000000000000000000000000000000000000000000000000000000000000047
:20596000000000000000000000000000000000000000000000000000000000000000000027
:20598000000000000000000000000000000000000000000000000000000000000000000007
:2059A0000000000000000000000000000000000000000000000000000000000000000000E7
:2059C0000000000000000000000000000000000000000000000000000000000000000000C7
:2059E0000000000000000000000000000000000000000000000000000000000000000000A7
:205A0000000000000000000000000000000000000000000000000000000000000000000086
:205A2000000000000000000000000000000000000000000000000000000000000000000066
:205A4000000000000000000000000000000000000000000000000000000000000000000046
:205A6000000000000000000000000000000000000000000000000000000000000000000026
:205A8000000000000000000000000000000000000000000000000000000000000000000006
:205AA0000000000000000000000000000000000000000000000000000000000000000000E6
:205AC0000000000000000000000000000000000000000000000000000000000000000000C6
:205AE0000000000000000000000000000000000000000000000000000000000000000000A6
:205B0000000000000000000000000000000000000000000000000000000000000000000085
:205B2000000000000000000000000000000000000000000000000000000000000000000065
:205B4000000000000000000000000000000000000000000000000000000000000000000045
:205B6000000000000000000000000000000000000000000000000000000000000000000025
:205B8000000000000000000000000000000000000000000000000000000000000000000005
:205BA0000000000000000000000000000000000000000000000000000000000000000000E5
:205BC0000000000000000000000000000000000000000000000000000000000000000000C5
:205BE0000000000000000000000000000000000000000000000000000000000000000000A5
```

```
:205C000000000000000000000000000000000000000000000000000000000000000084
:205C200000000000000000000000000000000000000000000000000000000000000064
:205C400000000000000000000000000000000000000000000000000000000000000044
:205C600000000000000000000000000000000000000000000000000000000000000024
:205C800000000000000000000000000000000000000000000000000000000000000004
:205CA0000000000000000000000000000000000000000000000000000000000000E4
:205CC0000000000000000000000000000000000000000000000000000000000000C4
:205CE0000000000000000000000000000000000000000000000000000000000000A4
:205D000000000000000000000000000000000000000000000000000000000000000083
:205D200000000000000000000000000000000000000000000000000000000000000063
:205D400000000000000000000000000000000000000000000000000000000000000043
:205D600000000000000000000000000000000000000000000000000000000000000023
:205D800000000000000000000000000000000000000000000000000000000000000003
:205DA0000000000000000000000000000000000000000000000000000000000000E3
:205DC0000000000000000000000000000000000000000000000000000000000000C3
:205DE0000000000000000000000000000000000000000000000000000000000000A3
:205E000000000000000000000000000000000000000000000000000000000000000082
:205E200000000000000000000000000000000000000000000000000000000000000062
:205E400000000000000000000000000000000000000000000000000000000000000042
:205E600000000000000000000000000000000000000000000000000000000000000022
:205E800000000000000000000000000000000000000000000000000000000000000002
:205EA0000000000000000000000000000000000000000000000000000000000000E2
:205EC0000000000000000000000000000000000000000000000000000000000000C2
:205EE0000000000000000000000000000000000000000000000000000000000000A2
:205F000000000000000000000000000000000000000000000000000000000000000081
:205F200000000000000000000000000000000000000000000000000000000000000061
:205F400000000000000000000000000000000000000000000000000000000000000041
:205F600000000000000000000000000000000000000000000000000000000000000021
:205F800000000000000000000000000000000000000000000000000000000000000001
:205FA0000000000000000000000000000000000000000000000000000000000000E1
:205FC0000000000000000000000000000000000000000000000000000000000000C1
:205FE0000000000000000000000000000000000000000000000000000000000000A1
:00000001FF
```

The invention claimed is:

1. A method for measuring a liquid freezing point on a roadway, said method comprising:
   (a) providing a sensor module embedded in a roadway, said sensor module comprising a measurement zone on an upper surface thereof, a temperature sensor in good thermal contact with the measurement zone, a pair of conductivity probes in good electrical contact with the measurement zone, and an active cooler thermally coupled to the measurement zone;
   (b) progressively cooling the measurement zone with the active cooler;
   (c) recording temperature measurements of the measurement zone with the temperature sensor repeatedly during (b);
   (d) recording conductivity measurements of the measurement zone with the conductivity probes repeatedly during (b);
   (e) determining a freezing point of a liquid in the measuring zone based on both variations in time of the temperature measurements of (c) and the conductivity measurements of (d).

2. The method of claim 1 wherein the measurement zone of (a) comprises a sample well having a first surface in good thermal contact with the temperature sensor and a second surface in good thermal contact with the active cooler.

3. The method of claim 1 wherein (e) comprises:
   (e1) determining the freezing point based on variations in time of the temperature measurements of (c); and
   (e2) checking whether the conductivity measurements of (d) indicate a substantial decrease in conductivity substantially coincident with the freezing point determined in (e1).

4. The method of claim 3 wherein (e1) comprises:
   (e1a) determining a second time derivative of the temperature measurements of(c);
   (e1b) comparing the second time derivative of(e1a) with a positive threshold value; and
   (e1c) determining the freezing point based on detection of a leveling off of the temperature measurements of (c) after the second time derivative of (e1a) has exceeded the threshold value of (e1b).

5. A method for measuring a liquid freezing point on a roadway, said method comprising:
   (a) providing a sensor module embedded in a roadway, said sensor module comprising a measurement zone on an upper surface thereof, a temperature sensor in good thermal contact with the measurement zone, and an active cooler thermally coupled to the measurement zone;
   (b) progressively cooling the measurement zone with the active cooler;
   (c) recording temperature measurements of the measurement zone with the temperature sensor repeatedly during (b);
   (d) determining a first time derivative of the temperature measurements of (c);
   (e) determining when the first time derivative rises above a first, positive threshold value; and then
   (f) determining when the first time derivative falls to within a range of values bounded above by zero and below by a second, negative threshold value;
   (g) associating a temperature measurement with a first time derivative determined in (f) as the liquid freezing point.

6. The method of claim 5 wherein (d) comprises:
   (d1) fitting a plurality of lines to the temperature measurements of (c); and
   (d2) determining a first time derivative of the lines of (d1).

7. The method of claim 6 further comprising:
   (g) associating the earliest temperature measurement included in the line associated with a first time derivative determined in (f) as the liquid freezing point.

8. A method for measuring a liquid freezing point on a roadway, said method comprising:
   (a) providing a sensor module embedded in a roadway, said sensor module comprising a measurement zone on an upper surface thereof, a temperature sensor in good thermal contact with the measurement zone, and an active cooler thermally coupled to the measurement zone;
   (b) progressively cooling the measurement zone with the active cooler;
   (c) recording temperature measurements of the measurement zone with the temperature sensor repeatedly during (b);
   (d) determining a second time derivative of the temperature measurements of (c);
   (e) determining when the second time derivative of (d) exceeds a positive threshold value; and
   (f) determining the freezing point based at least in part on a leveling off of the temperature measurements of (c) after the second time derivative of (d) has exceeded the threshold value of (e).

9. The method of claim 8 wherein (d) comprises:
   (d1) determining a plurality of first slopes of the temperature measurements of (c) versus time, each first slope associated with a respective measurement time; and
   (d2) determining a plurality of second slopes of the first slopes of (d1) versus time.

10. A method for measuring a liquid freezing point on a roadway, said method comprising:
    (a) providing a sensor module embedded in a roadway, said sensor module comprising a measurement zone on an upper surface thereof, a temperature sensor in good thermal contact with the measurement zone, and an active cooler thermally coupled to the measurement zone;
    (b) progressively cooling the measurement zone with the active cooler;
    (c) recording temperature measurements of the measurement zone with the temperature sensor repeatedly during (b);
    (d) determining a first time derivative and a second time derivative of the temperature measurements of (c);
    (e) determining when the second time derivative rises above a first, positive threshold value; and then
    (f) determining when the first time derivative falls to within a range of values bounded above by zero and below by a second, negative threshold value;
    (g) associating a temperature measurement with a first time derivative determined in (f) as the liquid freezing point.

11. The method of claim 10 wherein (d) comprises:
    (d1) fitting a plurality of lines to the temperature measurements of (c); and
    (d2) determining a first time derivative of the lines of (d1).

12. The method of claim 11 further comprising:
    (g) associating the earliest temperature measurement included in the line associated with a first time derivative determined in (f) as the liquid freezing point.

* * * * *

UNITED STATES PATENT AND TRADEMARK OFFICE
CERTIFICATE OF CORRECTION

| | | |
|---|---|---|
| PATENT NO. | : 7,090,392 B2 | Page 1 of 1 |
| APPLICATION NO. | : 10/701906 | |
| DATED | : August 15, 2006 | |
| INVENTOR(S) | : Patrick A. Leonhardt | |

It is certified that error appears in the above-identified patent and that said Letters Patent is hereby corrected as shown below:

On the Title Page

In column 1, line 7, under "U.S. PATENT DOCUMENTS" item [56], after "3,582,728 A" delete "6/1971" and substitute --3/1969-- in its place.

In column 2, line 1, after "3,613,063 A" delete "10/1971" and substitute --9/1968-- in its place.

Page 2, in column 2, line 7, under "OTHER PUBLICATIONS", delete "*Cransfield*" and substitute --*Cranfield*-- in its place.

Page 2, in column 2, line 34, under "OTHER PUBLICATIONS", immediately before "Building" insert --"-- (quotation mark).

Signed and Sealed this

Twenty-seventh Day of March, 2007

JON W. DUDAS
*Director of the United States Patent and Trademark Office*